(12) United States Patent
Ambhaikar et al.

(10) Patent No.: US 8,884,018 B2
(45) Date of Patent: Nov. 11, 2014

(54) PROCESS FOR PREPARING MODULATORS OF CYSTIC FIBROSIS TRANSMEMBRANE CONDUCTANCE REGULATOR

(71) Applicant: Vertex Pharmaceuticals Incorporated, Boston, MA (US)

(72) Inventors: Narendra Bhalchandra Ambhaikar, Hyderabad (IN); Robert Hughes, San Diego, CA (US); Dennis James Hurley, San Marcos, CA (US); Elaine Chungmin Lee, Arlington, MA (US); Benjamin Littler, Carlsbad, CA (US); Mehdi Numa, San Diego, CA (US); Stefanie Roeper, Medford, MA (US); Urvi Sheth, San Diego, CA (US)

(73) Assignee: Vertex Pharmaceuticals Incorporated, Boston, MA (US)

( * ) Notice: Subject to any disclaimer, the term of this patent is extended or adjusted under 35 U.S.C. 154(b) by 0 days.

(21) Appl. No.: 14/200,656

(22) Filed: Mar. 7, 2014

(65) Prior Publication Data

US 2014/0187787 A1   Jul. 3, 2014

Related U.S. Application Data

(62) Division of application No. 13/678,840, filed on Nov. 16, 2012, which is a division of application No. 12/909,750, filed on Oct. 21, 2010, now Pat. No. 8,344,147.

(60) Provisional application No. 61/254,634, filed on Oct. 23, 2009.

(51) Int. Cl.
*C07D 487/08* (2006.01)

(52) U.S. Cl.
USPC ............................................ 546/156; 548/453

(58) Field of Classification Search
None
See application file for complete search history.

(56) References Cited

U.S. PATENT DOCUMENTS

2010/0113508 A1   5/2010   Binch et al.

FOREIGN PATENT DOCUMENTS

| WO | 2006002421 A2 | 1/2006 |
|----|---------------|--------|
| WO | 2010048526 A2 | 4/2010 |
| WO | 2010048573 A1 | 4/2010 |

OTHER PUBLICATIONS

Cheng, Jie, et al., "Synthesis of N-Heteroaryl-7-azabicyclo[2.2.1]heptane Derivatives via Palladium-Bisimidazol-2-ylidene Complex Catalyzed Amination Reactions," Org Letters, 2001, vol. 3. No. 9, pp. 1371-1374.
International Search Report for PCT/US2010/053628, dated Feb. 22, 2011.

*Primary Examiner* — Janet L Andres
*Assistant Examiner* — Timothy R Rozof
(74) *Attorney, Agent, or Firm* — Honigman Miller Schwartz and Cohn LLP; Christopher C. Forbes; Jonathan P. O'Brien

(57) ABSTRACT

The present invention relates to processes for preparing solid state forms of N-(4-(7-azabicyclo[2.2.1]heptan-7-yl)-2-(trifluoromethyl)phenyl)-4-oxo-5-(trifluoromethyl)-1,4-dihydroquinoline-3-carboxamide, including Compound 1 Form A, Compound 1 Form A-HCl, Compound 1 Form B, and Compound 1 Form B-HCl, any combination of these forms, pharmaceutical compositions thereof, and methods of treatment therewith.

7 Claims, 22 Drawing Sheets

DSC

TGA

DSC

TGA

PROCESS FOR PREPARING MODULATORS OF CYSTIC FIBROSIS TRANSMEMBRANE CONDUCTANCE REGULATOR

CLAIM OF PRIORITY

This application is a division of U.S. Ser. No. 13/678,840, filed Nov. 16, 2012, which is a division of Ser. No. 12/909,750, filed Oct. 21, 2010 (now U.S. Pat. No. 8,344,147, issued Jan. 1, 2013), which claims priority to provisional application U.S. Ser. No. 61/254,634, filed on Oct. 23, 2009. The contents of the aforementioned applications are incorporated herein by reference in their entirety.

TECHNICAL FIELD OF THE INVENTION

The present invention relates to a process for making modulators of cystic fibrosis transmembrane conductance regulator ("CFTR").

BACKGROUND

Cystic fibrosis (CF) is a recessive genetic disease that affects approximately 30,000 children and adults in the United States and approximately 30,000 children and adults in Europe. Despite progress in the treatment of CF, there is no cure.

CF is caused by mutations in the cystic fibrosis transmembrane conductance regulator (CFTR) gene that encodes an epithelial chloride ion channel responsible for aiding in the regulation of salt and water absorption and secretion in various tissues. Small molecule drugs, known as potentiators that increase the probability of CFTR channel opening represent one potential therapeutic strategy to treat CF.

Specifically, CFTR is a cAMP/ATP-mediated anion channel that is expressed in a variety of cell types, including absorptive and secretory epithelia cells, where it regulates anion flux across the membrane, as well as the activity of other ion channels and proteins. In epithelia cells, normal functioning of CFTR is critical for the maintenance of electrolyte transport throughout the body, including respiratory and digestive tissue. CFTR is composed of approximately 1480 amino acids that encode a protein made up of a tandem repeat of transmembrane domains, each containing six transmembrane helices and a nucleotide binding domain. The two transmembrane domains are linked by a large, polar, regulatory (R)-domain with multiple phosphorylation sites that regulate channel activity and cellular trafficking.

The gene encoding CFTR has been identified and sequenced (See Gregory, R. J. et al. (1990) Nature 347:382-386; Rich, D. P. et al. (1990) Nature 347:358-362), (Riordan, J. R. et al. (1989) Science 245:1066-1073). A defect in this gene causes mutations in CFTR resulting in cystic fibrosis ("CF"), the most common fatal genetic disease in humans. Cystic fibrosis affects approximately one in every 2,500 infants in the United States. Within the general United States population, up to 10 million people carry a single copy of the defective gene without apparent ill effects. In contrast, individuals with two copies of the CF associated gene suffer from the debilitating and fatal effects of CF, including chronic lung disease.

In patients with CF, mutations in CFTR endogenously expressed in respiratory epithelia leads to reduced apical anion secretion causing an imbalance in ion and fluid transport. The resulting decrease in anion transport contributes to enhanced mucus accumulation in the lung and the accompanying microbial infections that ultimately cause death in CF patients. In addition to respiratory disease, CF patients typically suffer from gastrointestinal problems and pancreatic insufficiency that, if left untreated, results in death. In addition, the majority of males with cystic fibrosis are infertile and fertility is decreased among females with cystic fibrosis. In contrast to the severe effects of two copies of the CF associated gene, individuals with a single copy of the CF associated gene exhibit increased resistance to cholera and to dehydration resulting from diarrhea—perhaps explaining the relatively high frequency of the CF gene within the population.

Sequence analysis of the CFTR gene of CF chromosomes has revealed a variety of disease causing mutations (Cutting, G. R. et al. (1990) Nature 346:366-369; Dean, M. et al. (1990) Cell 61:863:870; and Kerem, B-S. et al. (1989) Science 245: 1073-1080; Kerem, B-S et al. (1990) Proc. Natl. Acad. Sci. USA 87:8447-8451). To date, >1000 disease causing mutations in the CF gene have been identified (http://www.genet.sickkids.on.ca/cftr/app). The most prevalent mutation is a deletion of phenylalanine at position 508 of the CFTR amino acid sequence, and is commonly referred to as ΔF508-CFTR. This mutation occurs in approximately 70% of the cases of cystic fibrosis and is associated with a severe disease.

The deletion of residue 508 in ΔF508-CFTR prevents the nascent protein from folding correctly. This results in the inability of the mutant protein to exit the ER, and traffic to the plasma membrane. As a result, the number of channels present in the membrane is far less than observed in cells expressing wild-type CFTR. In addition to impaired trafficking, the mutation results in defective channel gating. Together, the reduced number of channels in the membrane and the defective gating lead to reduced anion transport across epithelia leading to defective ion and fluid transport. (Quinton, P. M. (1990), FASEB J. 4: 2709-2727). Studies have shown, however, that the reduced numbers of ΔF508-CFTR in the membrane are functional, albeit less than wild-type CFTR. (Dalemans et al. (1991), Nature Lond. 354: 526-528; Denning et al., supra; Pasyk and Foskett (1995), J. Cell. Biochem. 270: 12347-50). In addition to ΔF508-CFTR, other disease causing mutations in CFTR that result in defective trafficking, synthesis, and/or channel gating could be up- or down-regulated to alter anion secretion and modify disease progression and/or severity.

Although CFTR transports a variety of molecules in addition to anions, it is clear that this role (the transport of anions) represents one element in an important mechanism of transporting ions and water across the epithelium. The other elements include the epithelial $Na^+$ channel, ENaC, $Na^+/2Cl^-/K^+$ co-transporter, $Na^+$-$K^+$-ATPase pump and the basolateral membrane $K^+$ channels, that are responsible for the uptake of chloride into the cell.

These elements work together to achieve directional transport across the epithelium via their selective expression and localization within the cell. Chloride absorption takes place by the coordinated activity of ENaC and CFTR present on the apical membrane and the $Na^+$-$K^+$-ATPase pump and $Cl^-$ ion channels expressed on the basolateral surface of the cell. Secondary active transport of chloride from the luminal side leads to the accumulation of intracellular chloride, which can then passively leave the cell via CF channels, resulting in a vectorial transport. Arrangement of $Na^+/2Cl^-/K^+$ co-transporter, $Na^+$-$K^+$-ATPase pump and the basolateral membrane $K^+$ channels on the basolateral surface and CFTR on the luminal side coordinate the secretion of chloride via CFTR on the luminal side. Because water is probably never actively transported itself, its flow across epithelia depends on tiny transepithelial osmotic gradients generated by the bulk flow of sodium and chloride.

As discussed above, it is believed that the deletion of residue 508 in ΔF508-CFTR prevents the nascent protein from folding correctly, resulting in the inability of this mutant protein to exit the ER, and traffic to the plasma membrane. As a result, insufficient amounts of the mature protein are present at the plasma membrane and chloride transport within epithelial tissues is significantly reduced. In fact, this cellular phenomenon of defective ER processing of ABC transporters by the ER machinery has been shown to be the underlying basis not only for CF disease, but for a wide range of other isolated and inherited diseases.

Accordingly, there is a need for potent and selective CFTR potentiators of wild-type and mutant forms of human CFTR. These mutant CFTR forms include, but are not limited to, ΔF508del, G551D, R117H, 2789+5G→A.

There is also a need for modulators of CFTR activity, and compositions thereof, which can be used to modulate the activity of the CFTR in the cell membrane of a mammal.

There is a need for methods of treating diseases caused by mutation in CFTR using such modulators of CFTR activity.

There is a need for methods of modulating CFTR activity in an ex vivo cell membrane of a mammal.

In addition, there is a need for stable solid forms of said compound that can be used readily in pharmaceutical compositions suitable for use as therapeutics.

SUMMARY OF THE INVENTION

The present invention relates to processes for the synthesis of compounds useful as modulators of CFTR.

In one aspect, the invention provides A process for making a crystalline form of Compound 1:

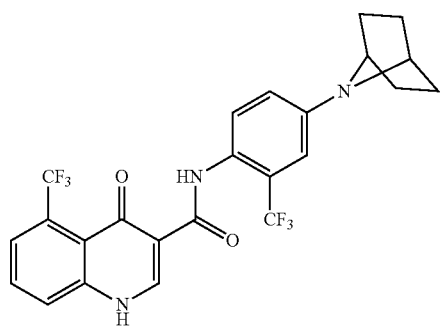

comprising:

(a) reacting Compound 2 with Compound 3 in the presence of a coupling agent:

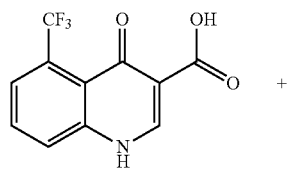

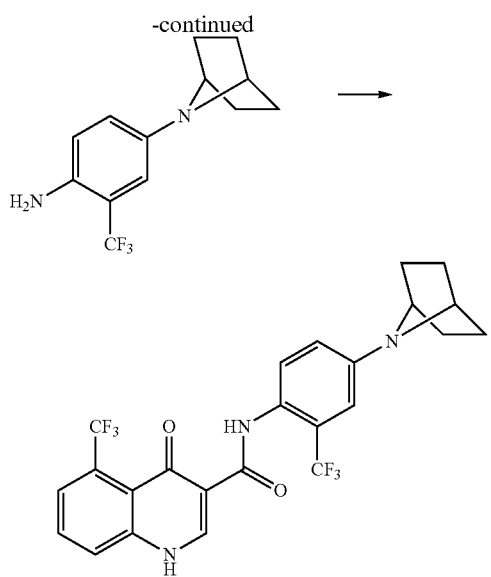

wherein the coupling agent is selected from the group consisting of 2-chloro-1,3-dimethyl-2-imidazolium tetrafluoroborate, HBTU, HCTU, 2-chloro-4,6-dimethoxy-1,3,5-triazine, HATU, HOBT/EDC, and T3P®.

Compounds of Formula I and pharmaceutically acceptable compositions thereof are useful for treating or lessening the severity of a variety of diseases, disorders, or conditions, including, but not limited to, cystic fibrosis, asthma, smoke induced COPD, chronic bronchitis, rhinosinusitis, constipation, pancreatitis, pancreatic insufficiency, male infertility caused by congenital bilateral absence of the vas deferens (CBAVD), mild pulmonary disease, idiopathic pancreatitis, allergic bronchopulmonary aspergillosis (ABPA), liver disease, hereditary emphysema, hereditary hemochromatosis, coagulation-fibrinolysis deficiencies, such as protein C deficiency, Type 1 hereditary angioedema, lipid processing deficiencies, such as familial hypercholesterolemia, Type 1 chylomicronemia, abetalipoproteinemia, lysosomal storage diseases, such as I-cell disease/pseudo-Hurler, mucopolysaccharidoses, Sandhof/Tay-Sachs, Crigler-Najjar type II, polyendocrinopathy/hyperinsulemia, Diabetes mellitus, Laron dwarfism, myleoperoxidase deficiency, primary hypoparathyroidism, melanoma, glycanosis CDG type 1, congenital hyperthyroidism, osteogenesis imperfecta, hereditary hypofibrinogenemia, ACT deficiency, Diabetes insipidus (DI), neurophyseal DI, neprogenic DI, Charcot-Marie Tooth syndrome, Perlizaeus-Merzbacher disease, neurodegenerative diseases such as Alzheimer's disease, Parkinson's disease, amyotrophic lateral sclerosis, progressive supranuclear plasy, Pick's disease, several polyglutamine neurological disorders such as Huntington's, spinocerebullar ataxia type I, spinal and bulbar muscular atrophy, dentatorubal pallidoluysian, and myotonic dystrophy, as well as spongiform encephalopathies, such as hereditary Creutzfeldt-Jakob disease (due to prion protein processing defect), Fabry disease, Straussler-Scheinker syndrome, COPD, dry-eye disease, or Sjogren's disease, Osteoporosis, Osteopenia, bone healing and bone growth (including bone repair, bone regeneration, reducing bone resorption and increasing bone deposition), Gorham's Syndrome, chloride channelopathies such as myotonia congenita (Thomson and Becker forms), Bartter's syndrome type III, Dent's disease, hyperekplexia, epilepsy, hyperekplexia, lysosomal storage disease, Angelman syndrome, and Primary Ciliary Dyskinesia (PCD), a term for inherited disorders of the structure and/or function of cilia, including PCD with situs inversus (also known as Kartagener syndrome), PCD without situs inversus and ciliary aplasia.

In one aspect, Compound 1 is in a crystalline form referred to as Form A.

In another aspect, Compound 1 is in a crystalline form referred to as Form B.

In a further aspect, Compound 1 is in a crystalline form referred to as Form A-HCl.

In an additional aspect, Compound 1 is in a crystalline form referred to as Form B-HCl.

Processes described herein can be used to prepare the compositions of this invention comprising Form A, Form A-HCl, Form B, Form B-HCl, or any combination of these forms.

DETAILED DESCRIPTION OF THE INVENTION

Definitions

Figure 1:
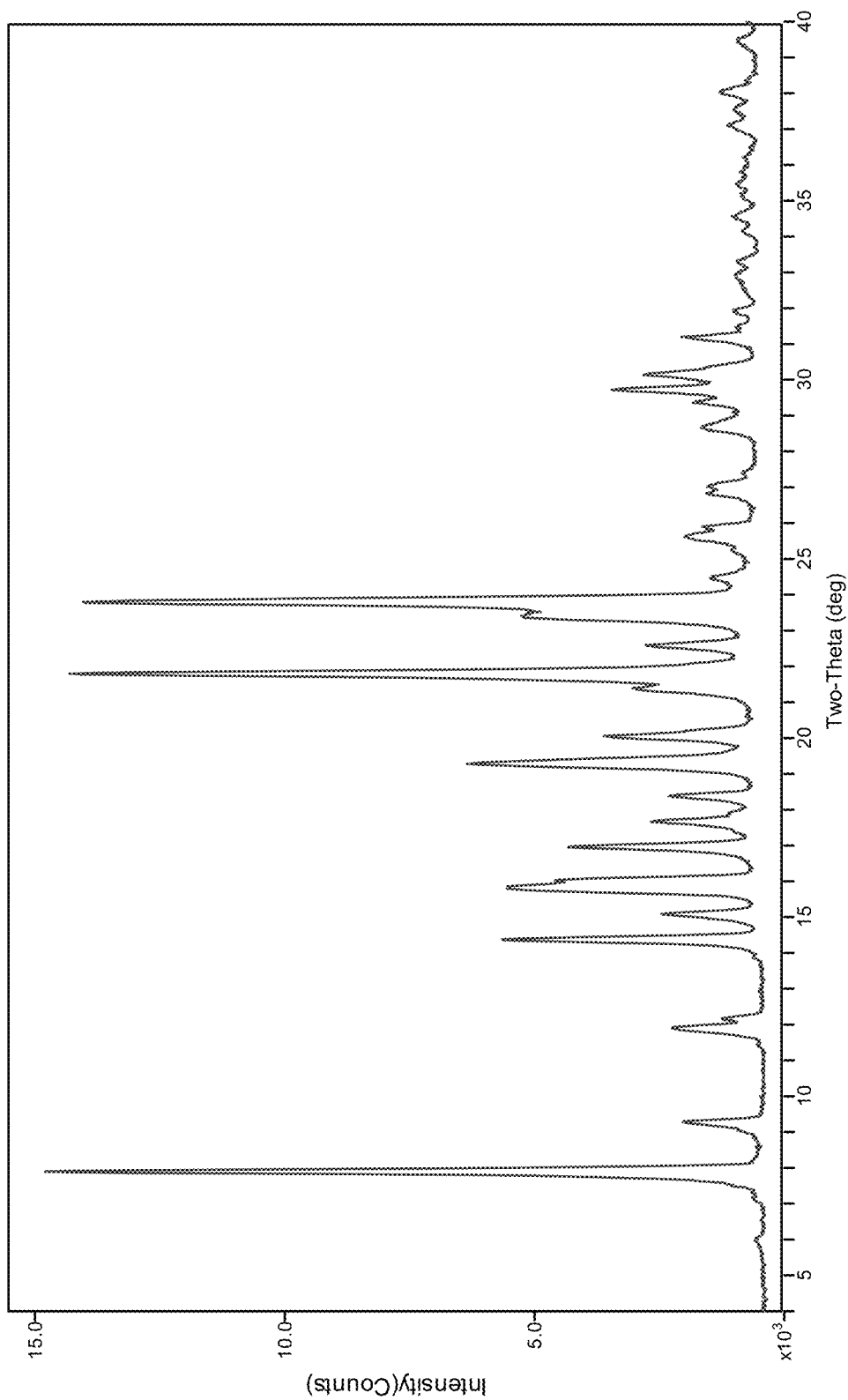
FIG. 1 is an X-ray powder diffraction pattern of a representative sample of Compound 1 Form A.

As used herein, the following definitions shall apply unless otherwise indicated.

The term "ABC-transporter" as used herein means an ABC-transporter protein or a fragment thereof comprising at least one binding domain, wherein said protein or fragment thereof is present in vivo or in vitro. The term "binding domain" as used herein means a domain on the ABC-transporter that can bind to a modulator. See, e.g., Hwang, T. C. et al., J. Gen. Physiol. (1998): 111(3), 477-90.

The term "CFTR" as used herein means cystic fibrosis transmembrane conductance regulator or a mutation thereof capable of regulator activity, including, but not limited to, ΔF508 CFTR, R117H CFTR, and G551D CFTR (see, e.g., http://www.genet.sickkids.on.ca/cftr/app, for CFTR mutations).

The term "modulating" as used herein means increasing or decreasing by a measurable amount.

The term "normal CFTR" or "normal CFTR function" as used herein means wild-type like CFTR without any impairment due to environmental factors such as smoking, pollution, or anything that produces inflammation in the lungs.

The term "reduced CFTR" or "reduced CFTR function" as used herein means less than normal CFTR or less than normal CFTR function.

The term "crystalline" refers to compounds or compositions where the structural units are arranged in fixed geometric patterns or lattices, so that crystalline solids have rigid long range order. The structural units that constitute the crystal structure can be atoms, molecules, or ions. Crystalline solids show definite melting points.

The term "substantially crystalline" refers to a solid material that is predominately arranged in fixed geometric patterns or lattices that have rigid long range order. For example, substantially crystalline materials have more than about 85% crystallinity (e.g., more than about 90% crystallinity, more than about 95% crystallinity, or more than about 99% crystallinity). It is also noted that the term 'substantially crystalline' includes the descriptor 'crystalline', which is defined in the previous paragraph.

For purposes of this invention, the chemical elements are identified in accordance with the Periodic Table of the Elements, CAS version, Handbook of Chemistry and Physics, 75th Ed. Additionally, general principles of organic chemistry are described in "Organic Chemistry", Thomas Sorrell, University Science Books, Sausalito: 1999, and "March's Advanced Organic Chemistry", 5th Ed., Ed.: Smith, M. B. and March, J., John Wiley & Sons, New York: 2001, the entire contents of which are hereby incorporated by reference.

The term "stable", as used herein, refers to compounds that are not substantially altered when subjected to conditions to allow for their production, detection, and preferably their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

Examples of suitable solvents that may be used in this invention are, but not limited to water, methanol, dichloromethane (DCM), acetonitrile, dimethylformamide (DMF), methyl acetate (MeOAc), ethyl acetate (EtOAc), isopropyl acetate (IPAc), t-butyl acetate (t-BuOAc), isopropyl alcohol (IPA), tetrahydrofuran (THF), methyl ethyl ketone (MEK), t-butanol, diethyl ether (Et$_2$O), methyl-t-butyl ether (MTBE), 1,4-dioxane and N-methylpyrrolidone (NMP).

Examples of suitable coupling agents that may be used in this invention are, but not limited to 1-(3-(dimethylamino)propyl)-3-ethyl-carbodiimide hydrochloride (EDCI), 2-(1H-benzotriazole-1-yl)-1,1,3,3-tetramethyluronium hexafluorophosphate (HBTU), 1-hydroxybenzotriazole (HOBT), 2-(1H-7-Azabenzotriazol-1-yl)-1,1,3,3-tetramethyl uronium hexafluorophosphate (HATU), 2-chloro-1,3-dimethyl-2-imidazolium tetrafluoroborate, 1-H-benzotriazolium-1-[bis(dimethylamino)methylene]-5-chlorohexafluorophosphate (HCTU), 2-chloro-4,6-dimethoxy-1,3,5-triazine, and 2-propane phosphonic anhydride (T3P6).

Examples of suitable bases that may be used in this invention are, but not limited to potassium carbonate (K$_2$CO$_3$), N-methylmorpholine (NMM), triethylamine (Et$_3$N; TEA), diisopropyl-ethyl amine (i-Pr$_2$EtN; DEA), pyridine, potassium hydroxide (KOH), sodium hydroxide (NaOH), and sodium methoxide (NaOMe; NaOCH$_3$).

Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}$C or $^{14}$C are within the scope of this invention. Such compounds are useful, for example, as analytical tools or probes in biological assays.

Processes of the Invention

In general, the invention provides processes for the synthesis of compounds useful as modulators of CFTR.

Preparation of Compound 1

In some embodiments, the invention provides a process for making a crystalline form of Compound 1:

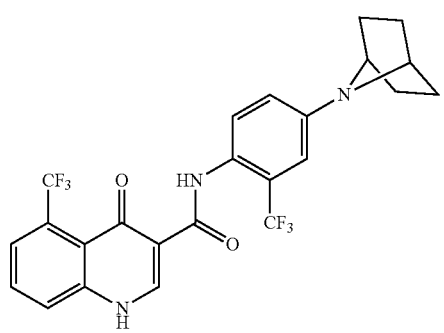

comprising:
(a) reacting Compound 2 with Compound 3 in the presence of a coupling agent

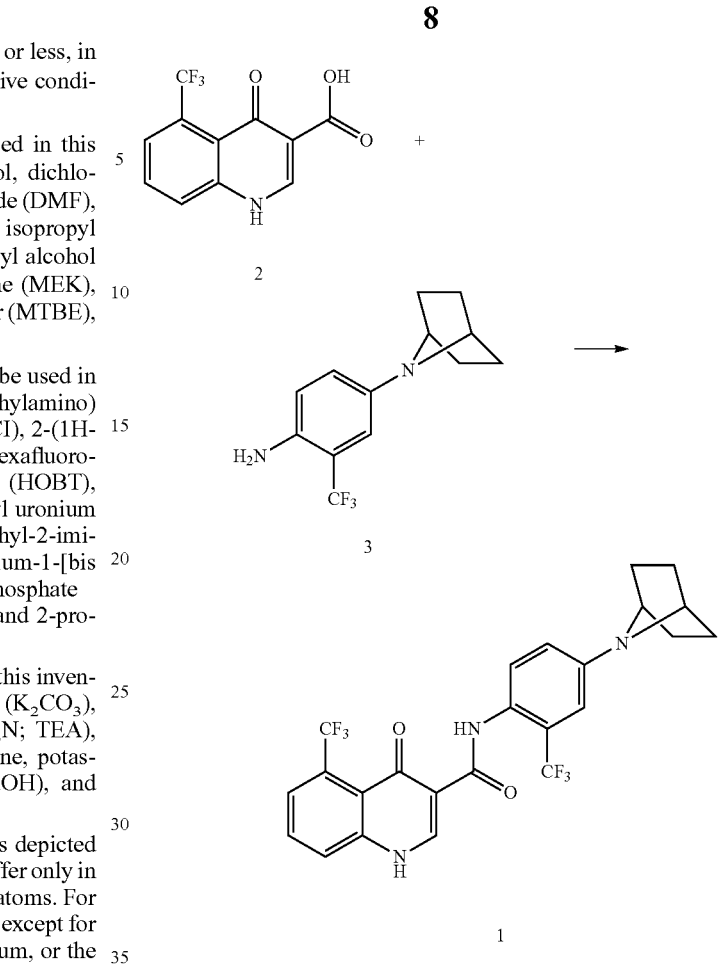

wherein the coupling agent is selected from the group consisting of 2-chloro-1,3-dimethyl-2-imidazolium tetrafluoroborate, HBTU, HCTU, 2-chloro-4,6-dimethoxy-1,3,5-triazine, HATU, HOBT/EDC, and T3P®.

In another aspect of this embodiment, Compound 3 can be the HCl salt.

In one aspect of this embodiment, the coupling of the Compound 2 and Compound 3 is performed in the presence of a base such as K$_2$CO$_3$, Et$_3$N,N-methylmorpholine (NMM), pyridine or diisopropylethyl amine (DIEA).

In another aspect of this embodiment, the coupling of Compound 2 and Compound 3 is performed in the presence of pyridine or DIEA.

In another aspect of this embodiment, the coupling of Compound 2 and Compound 3 is performed in the presence of pyridine.

In another aspect of this embodiment, the coupling of Compound 2 and Compound 3 is performed in the presence of a solvent. In one aspect, the solvent is a polar aprotic solvent. For example, the solvent is selected from the group consisting of ethyl acetate, isopropyl acetate, tetrahydrofuran, methylethyl ketone, N-Methyl-2-pyrrolidone, acetonitrile, N,N-dimethyl formamide, or 2-methyltetrahydrofuran. More particularly, the solvent is 2-methyltetrahydrofuran.

In another aspect of this embodiment, the coupling of Compound 2 and Compound 3 is performed at a reaction temperature that is maintained between 30° C. and 80° C. In further aspects, the coupling of Compound 2 and the aniline of Formula 3 is performed at a reaction temperature that is maintained between 30° C. and 80° C. (e.g., between about 40° C. and 78° C., between about 45° C. and 75° C., between about 50° C. and 70° C., between about 62° C. and 68° C., or about 65° C.) For example, the coupling of Compound 2 and Compound 3 is performed at a reaction temperature that is maintained at about 65° C.

In another aspect of this embodiment, Compound 1 is solid Form A.

In another embodiment, the invention provides Compound 1 prepared by the process described in the previous paragraphs.

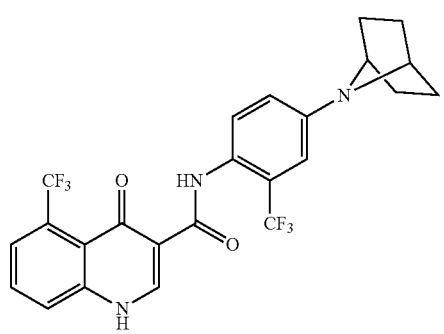

1

Preparation of Compound 1 Form A

In another embodiment, the invention provides a process for producing Compound 1 having solid Form A,

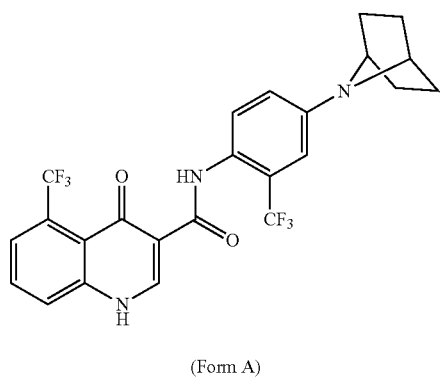

1 (Form A)

reacting Compound 2 with Compound 3 in the presence of a coupling agent

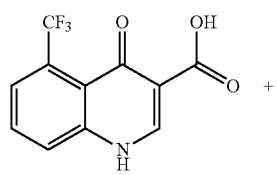

2

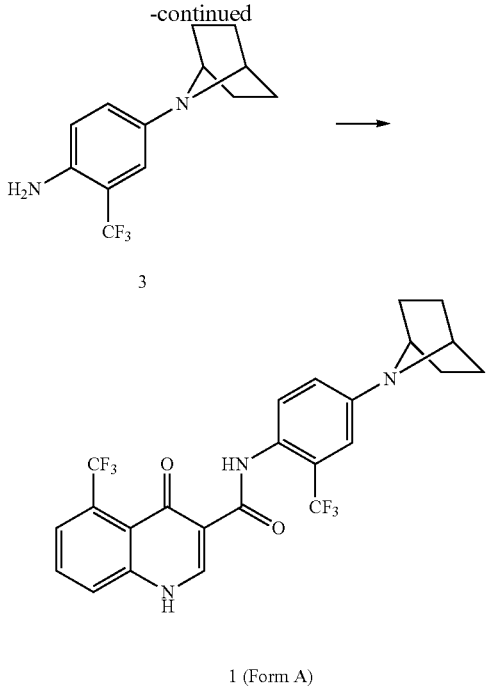

wherein the coupling agent is selected from the group consisting of 2-chloro-1,3-dimethyl-2-imidazolium tetrafluoroborate, HBTU, HCTU, 2-chloro-4,6-dimethoxy-1,3,5-triazine, HATU, HOBT/EDC, and T3P®.

In some other aspects of this embodiment, Compound 3 can be the HCl salt.

In one aspect of this embodiment, the coupling of Compound 2 and Compound 3 is performed in the presence of a base such as $K_2CO_3$, $Et_3N$,N-methylmorpholine (NMM), pyridine or diisopropylethyl amine (DIEA).

In another aspect of this embodiment, Compound 2 and Compound 3 is performed in the presence of pyridine or DIEA.

In another aspect of this embodiment, the coupling of Compound 2 and Compound 3 is performed in the presence of pyridine.

In another aspect of this embodiment, coupling of Compound 2 and Compound 3 is performed in the presence of a polar aprotic solvent. For example, the polar aprotic solvent is selected from the group consisting of ethyl acetate, isopropyl acetate, tetrahydrofuran, methylethyl ketone, N-Methyl-2-pyrrolidone, acetonitrile, N,N-dimethyl formamide, or 2-methyltetrahydrofuran. More particularly, the coupling of Compound 2 and Compound 3 is performed in the presence of a 2-methyltetrahydrofuran.

In another aspect of this embodiment, the coupling of Compound 2 and Compound 3 is performed at a reaction temperature that is maintained between 30° C. and 80° C. In further aspects, the coupling of Compound 2 and the aniline of Formula 3 is performed at a reaction temperature that is maintained between 30° C. and 80° C. (e.g., between about 40° C. and 78° C., between about 45° C. and 75° C., between about 50° C. and 70° C., between about 62° C. and 68° C., or about 65° C.) For example, the coupling of Compound 2 and Compound 3 is performed at a reaction temperature that is maintained at about 65° C.

In another embodiment, the invention provides Compound 1 Form A prepared by the process described in the preceding paragraphs.

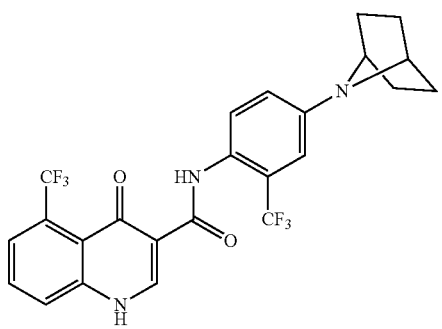

(Form A)

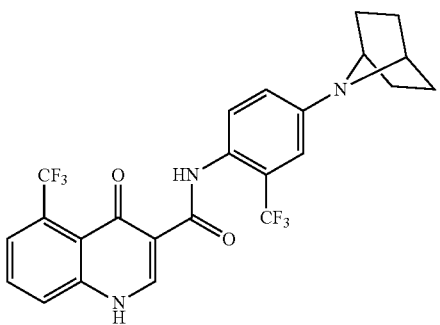

(Form B)

In one embodiment, the invention provides a process for preparing Compound 1 Form A, comprising reacting Compound 2 with Compound 3 in the presence of T3P® and pyridine at a temperature of about 65° C. for about 10 hours in the solvent, 2-MeTHF.

comprising:

(a) reacting Compound 2 with the hydrochloride salt of Compound 3 (3-HCl) in the presence of a coupling agent selected from the group consisting of 2-chloro-1,3-dimethyl-2-imidazolium tetrafluoroborate, HBTU, HCTU, 2-chloro-4,6-dimethoxy-1,3,5-triazine, HATU, HOBT/EDC, and T3P®

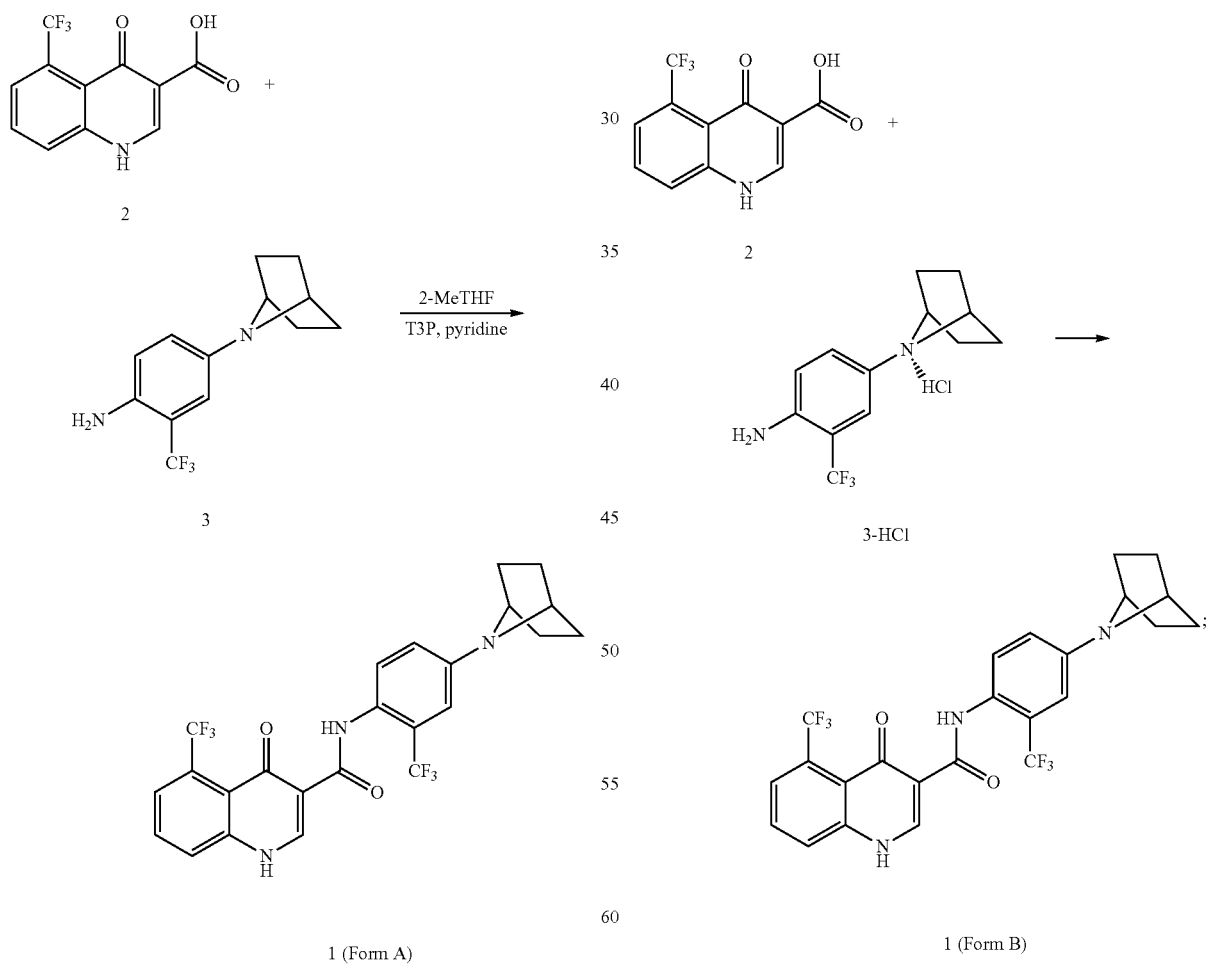

Preparation of Compound 1 Form B

In another embodiment, the invention provides a process for producing Compound 1 having solid form Form B:

In one aspect of this embodiment, the coupling of Compound 2 and the hydrochloride salt 3-HCl is performed in the presence of a base such as $K_2CO_3$, $Et_3N$, N-methylmorpholine (NMM), pyridine or DIEA.

In some other aspects of this embodiment, the hydrochloride salt 3-HCl can be Compound 3.

In another aspect of this embodiment, the coupling of Compound 2 and the hydrochloride salt 3-HCl is performed in the presence of pyridine or DIEA.

In another aspect of this embodiment, the coupling of Compound 2 and the hydrochloride salt 3-HCl is performed in the presence of pyridine.

In another aspect of this embodiment, the coupling of Compound 2 and the hydrochloride salt 3-HCl is performed in the presence of a solvent such as EtOAc, IPAc, THF, MEK, NMP, acetonitrile, DMF, or 2-methyltetrahydrofuran. More particularly, the coupling of Compound 2 and the hydrochloride salt 3-HCl is performed in the presence of a 2-methyltetrahydrofuran.

In another aspect of this embodiment, the coupling of Compound 2 and the hydrochloride salt 3-HCl is s performed at a reaction temperature that is maintained between 15° C. and 70° C. In further aspects, the coupling of Compound 2 and the hydrochloride salt 3-HCl is performed at a reaction temperature that is maintained between 15° C. and 70° C. (e.g., between about 20° C. and 65° C., between about 25° C. and 60° C., between about 30° C. and 55° C., between about 35° C. and 50° C., or about 45° C.). In a preferred aspect of this embodiment, the coupling of Compound 2 and the HCl salt of Compound 3 is performed at a reaction temperature that is maintained at about 45° C.

In another aspect, the coupling reaction is stirred for a duration of from about 1.5 hours to about 10 hours. In further aspects, the coupling reaction is stirred for a duration of from about 1.5 hours to about 10 hours (e.g., from about 2 hours to about 7 hours, from about 3 hours to about 6 hours, from about 4 hours to about 5.5 hours, or about 5 hours).

In another embodiment, the invention provides Compound 1 Form B prepared by the process of described in the preceding paragraphs.

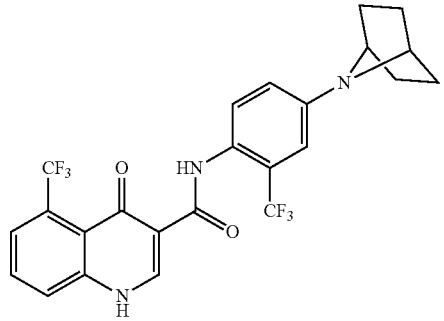

(Form B)

In one embodiment, the invention provides a process for preparing Compound 1 Form B, comprising reacting Compound 2 with Compound 3-HCl in the presence of T3P® and pyridine at a temperature of about 45° C. for about 5-6 hours in the solvent, 2-MeTHF.

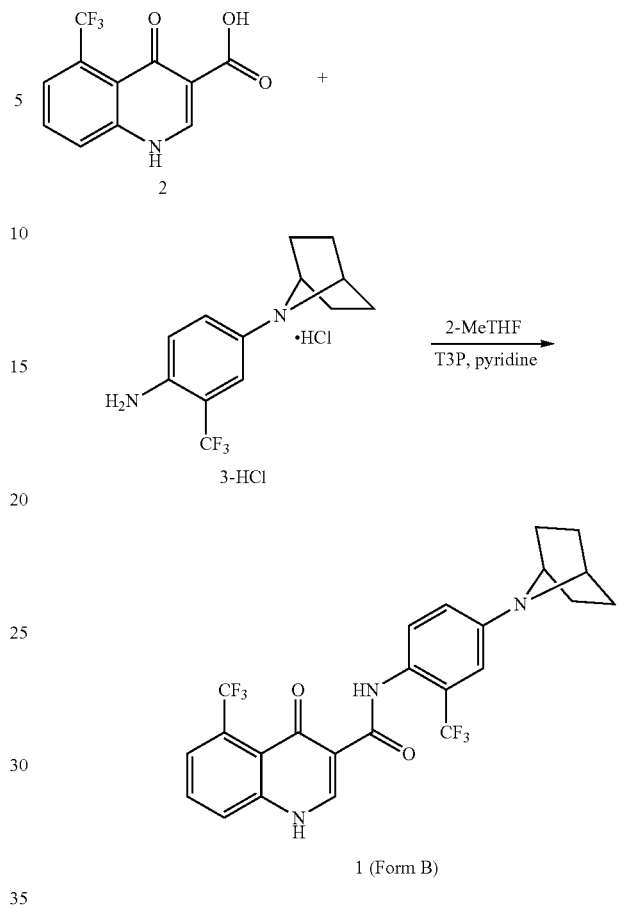

Preparation of Compound 1 Form A-HCl

In another embodiment, the invention provides a process for producing the hydrochloride salt of Compound 1 having solid Form A-HCl:

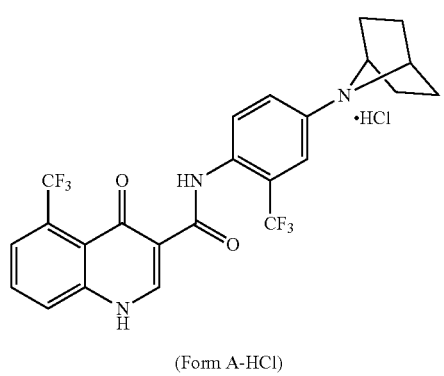

(Form A-HCl)

comprising:
(a) reacting Compound 2 with the hydrochloride salt of Compound 3 (3-HCl) in the presence of a coupling agent selected from the group consisting of 2-chloro-1,3-dimethyl-2-imidazolium tetrafluoroborate, HBTU, HCTU, 2-chloro-4,6-dimethoxy-1,3,5-triazine, HATU, HOBT/EDC, and T3P®:

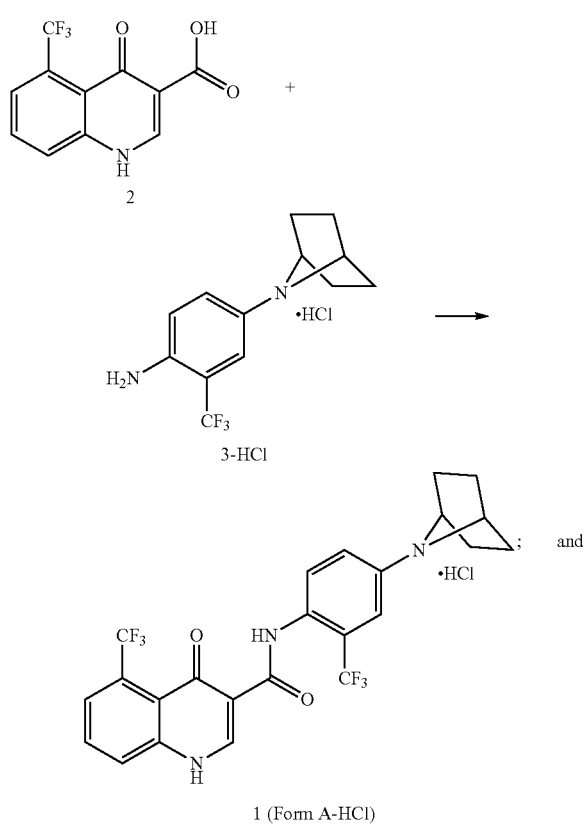

1 (Form A-HCl)

(b) treating a mixtures of the product of step (a) with HCl.

In one aspect of this embodiment, step (a) is performed in the presence of a base such as $K_2CO_3$, $Et_3N$, N-methylmorpholine (NMM), pyridine or diisopropylethyl amine (DIEA).

In another aspect of this embodiment, step (a) is performed in the presence of pyridine or DIEA.

In another aspect of this embodiment, step (a) is performed in the presence of pyridine.

In another aspect of this embodiment, step (a) is performed in the presence of a polar aprotic solvent. For example, the polar aprotic solvent is selected from the group consisting of ethyl acetate, isopropyl acetate, tetrahydrofuran, methylethyl ketone, N-Methyl-2-pyrrolidone, acetonitrile, N,N-dimethyl formamide, or 2-methyltetrahydrofuran. More particularly, the coupling of Compound 2 and 3-HCl is performed in the presence of a 2-methyltetrahydrofuran.

In another aspect of this embodiment, step (a) is performed at a reaction temperature that is maintained between 10° C. and 80° C. In another aspect of this embodiment, step (a) is performed at a reaction temperature that is maintained between 15° C. and 70° C. In further aspects, the coupling of Compound 2 and the HCl salt of Compound 3 is performed at a reaction temperature that is maintained between 15° C. and 70° C. (e.g., between about 20° C. and 65° C., between about 25° C. and 60° C., between about 30° C. and 55° C., between about 35° C. and 50° C., or about 45° C.) For example, the coupling of Compound 2 and 3-HCl is performed at a reaction temperature that is maintained at about 45° C.

In another aspect of this embodiment, the time of step (a) is from about 1.5 hours to about 72 hours. In further aspects, the coupling reaction is stirred for a duration of from about 1.5 hours to about 72 hours or more (e.g., from about 2 hours to about 48 hours, from about 3 hours to about 24 hours, from about 5 hours to about 20 hours, or from about 12 hours to about 15 hours).

In a further aspect of this embodiment, the coupling product in step (a) is treated with hydrogen chloride (HCl) in step (b). For example, HCl gas is bubbled into a mixture comprising the product of the coupling reaction of step (a) and apolar aprotic solvent such as 2-methyltetrahydrofuran.

Typically at least about 1 equivalent of HCl gas, and up to about 50 equivalents of HCl gas is bubbled into the mixture. More typically, from about 2 equivalents (eq.) to about 20 equivalents (from about of 5 eq to about 15 eq, from about 8 eq to about 12 eq, or about 10 eq) of HCl gas is bubbled into a reaction mixture comprising the coupling product of step (a).

Typically, the HCl gas is bubbled into the mixture product of step (a) and a solvent, such as an aprotic solvent, for a period of from about 0.5 hours to about 5 hours, and more typically, for a period of from about 0.5 hours to about 5 hours (e.g., from about 0.75 hours to about 3 hours, or about 2 hours).

In another embodiment, the invention provides Compound 1 Form A-HCl prepared by the process described in the preceding paragraphs.

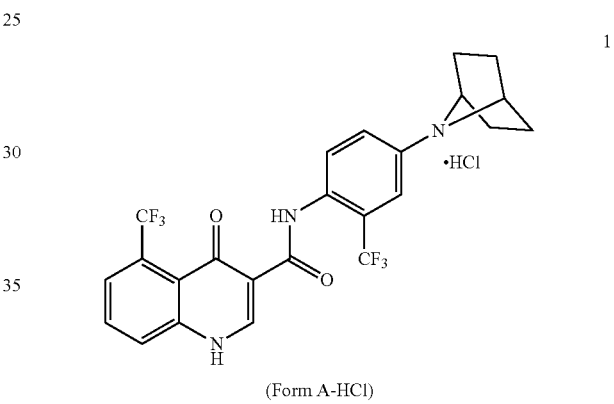

(Form A-HCl)

In one embodiment, the invention provides a process for preparing Compound 1 Form A-HCl, comprising reacting Compound 2 with Compound 3-HCl in the presence of T3P® and pyridine at a temperature of about 45° C. for about 12-15 hours in the solvent, 2-MeTHF, followed by treatment with gaseous HCl.

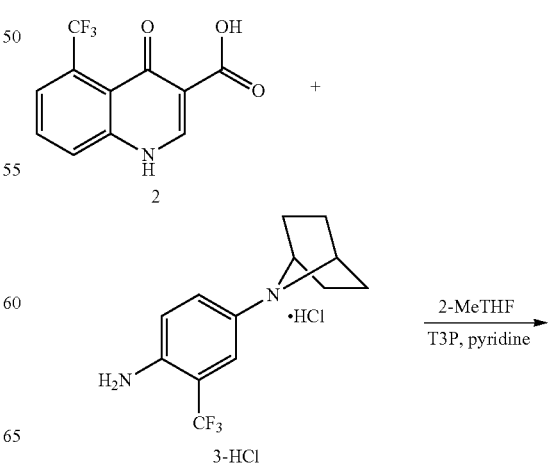

Preparation of Compound 1 Form B-HCl

In another aspect, the invention provides a process for producing a hydrochloride salt of Compound 1, having the solid form Form B-HCl:

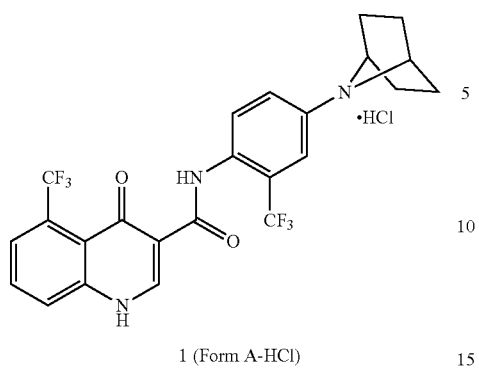

1 (Form A-HCl)

comprising:

(a) mixing a hydrochloride salt of Compound 1 Form A-HCl, as described herein, with an organic solvent and water to generate a mixture:

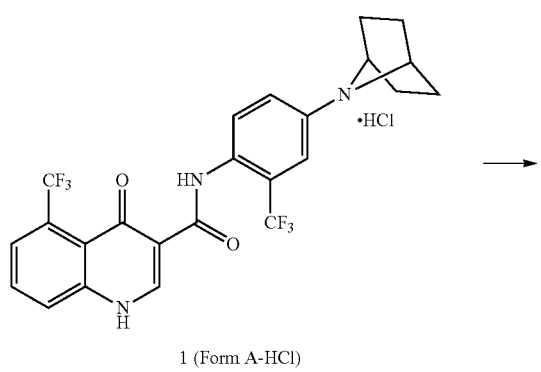

1 (Form A-HCl)

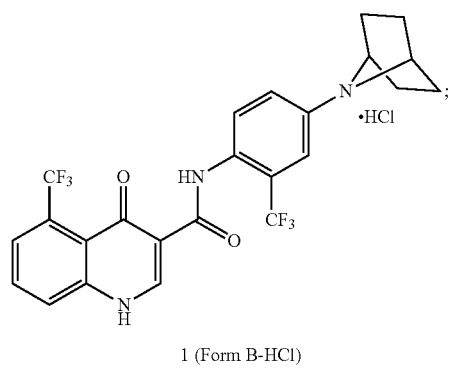

1 (Form B-HCl)

and (b) heating the mixture.

In one aspect of this embodiment, the organic solvent comprises dimethyl sulfoxide, dimethylformamide, dioxane, hexamethylphosphorotriamide, tetrahydrofuran, EtOAc, IPAc, THF, MEK, NMP, acetonitrile, DMF, EtOH, MeOH, isopropyl alcohol, or 2-methyltetrahydrofuran. More particularly, the aprotic solvent comprises 2-methyltetrahydrofuran.

In another aspect, the mixing in step (a) is followed in step (b) with maintaining the mixture at a temperature of from about 30° C. to about 80° C. (e.g., from about 40° C. to about 70° C., from about 50° C. to about 65° C., or about 60° C.) In one embodiment of this aspect, the mixture is maintained at a temperature of 30° C. to about 80° C. for a period of from about 12 hours to about 72 hours.

In another aspect, after heating in step (b), the mixture is filtered to generate a filter cake.

In another aspect, the filtering is followed by washing the filter cake with an aprotic solvent such as 2-methyltetrahydrofuran.

In another embodiment, the invention provides Compound 1 Form B-HCl prepared by the process described in the preceding paragraphs.

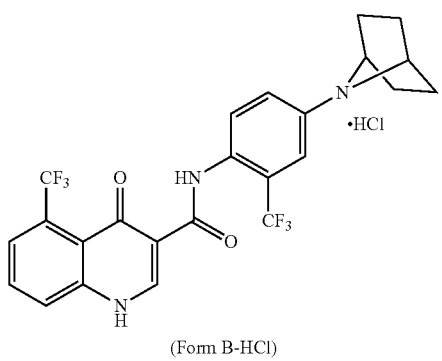

(Form B-HCl)

In one embodiment, the invention provides a process for preparing Compound 1 Form B-HCl, comprising heating Compound 1 Form A-HCl in a mixture of 2-MeTHF and water at a temperature of 60° C. for 48 hours; cooling to room temperature and filtering precipitated product; and drying the produce under vacuum at a temperature of 60° C.

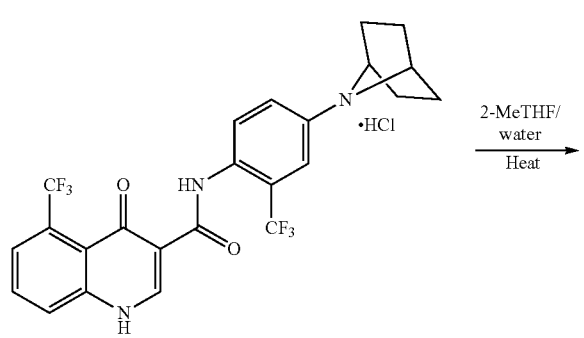

1 (Form A-HCl)

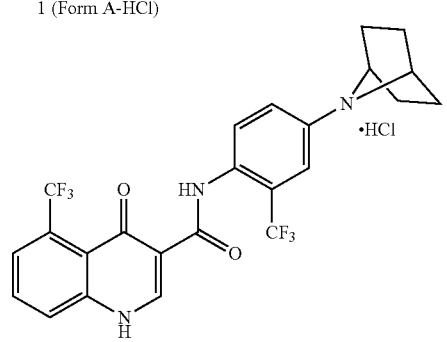

1 (Form B-HCl)

In another embodiment, the invention provides a process for preparing Compound 1 Form B-HCl, comprising heating Compound 1 Form A-HCl in a mixture of EtOH and water to reflux temperature; cooling to 20° C. and stirring for 3 hours; filtering precipitated product; and drying the produce under vacuum at a temperature of 45° C.

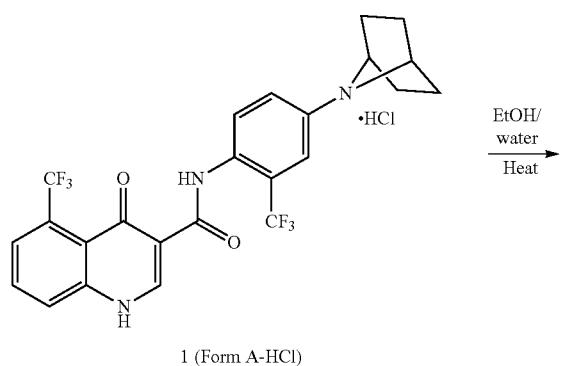

1 (Form A-HCl)

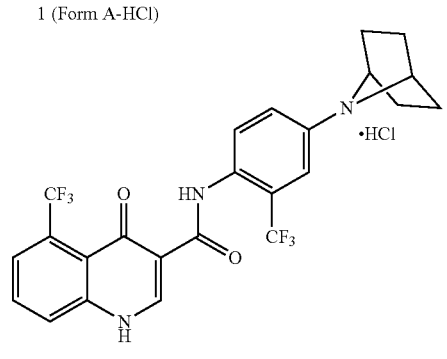

1 (Form B-HCl)

Preparation of Compounds 2, 3, and 3-HCl

In another embodiment, the invention provides a method for preparing Compound 2:

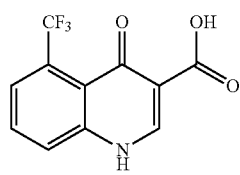

comprising:
(a) reacting Compound 4 with diethyl 2-(ethoxymethylene)malonate 5 to generate ester 6A

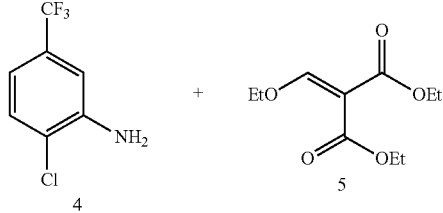

(b) treating ester 6A with a source of atomic hydrogen, such as hydrogen gas or formate in the presence of a catalyst and a base in separate steps to generate Compound 2

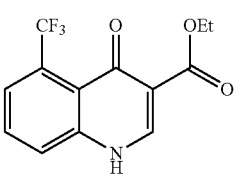

In one aspect, Compound 6A is treated with a source of atomic hydrogen, such as hydrogen gas or formate in the presence of a catalyst to produce Compound 6C

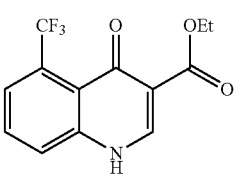

which is then treated with a base to produce Compound 2.
In another aspect, Compound 6A is treated with a base to produce Compound 6D

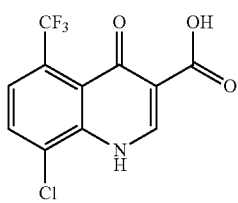

6D which is then treated with a source of atomic hydrogen, such as hydrogen gas or formate in the presence of a catalyst to produce Compound 2.

In some aspects, the source of hydrogen is hydrogen gas. In other aspects, the source of hydrogen is formate.

In some aspects, the catalyst is a palladium catalyst.

In some aspects, the base is aqueous sodium hydroxide or aqueous potassium hydroxide. For example, the base is aqueous sodium hydroxide.

In one embodiment, the invention provides a process for preparing Compound 2 comprising the steps of:

a) reacting Compound 4 with Compound 5 in toluene at reflux temperature in a Dean-Stark apparatus to form Compound 6B;

b) heating Compound 6B in Dowtherm, at a temperature of about 260° C. to produce the cyclized product, Compound 6A;

c) hydrogenating Compound 6A in EtOH using Pd/C as a catalyst in the presence of hydrogen gas and triethylamine to produce Compound 6C; and d) hydrolyzing Compound 6C using 5 M NaOH to produce Compound 2

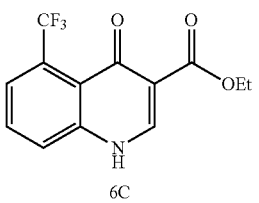

6C

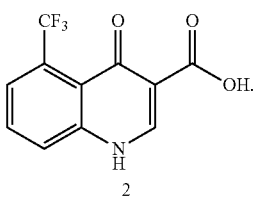

2

In one embodiment, the invention provides a process for preparing Compound 2 comprising the steps of:

a) reacting Compound 4 with Compound 5 in toluene at reflux temperature in a Dean-Stark apparatus to form Compound 6B;

b) heating Compound 6B in Dowtherm, at a temperature of about 260° C. to produce the cyclized product, Compound 6A;

c) hydrolyzing Compound 6A using NaOH in a mixture of isopropanol and water to produce Compound 6D; and d) hydrogenating Compound 6D in EtOH using Pd/C as a catalyst in the presence of formate, sodium methoxide and methanol; and e) acidifying the solution with acetic acid to produce Compound 2

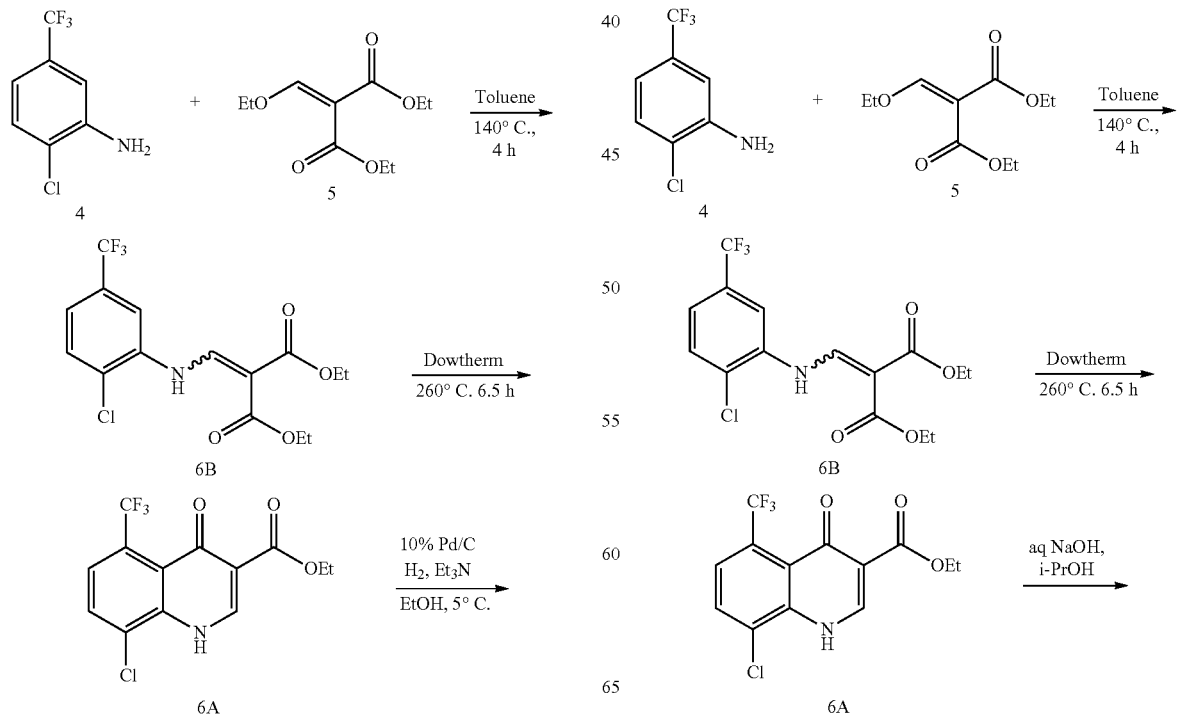

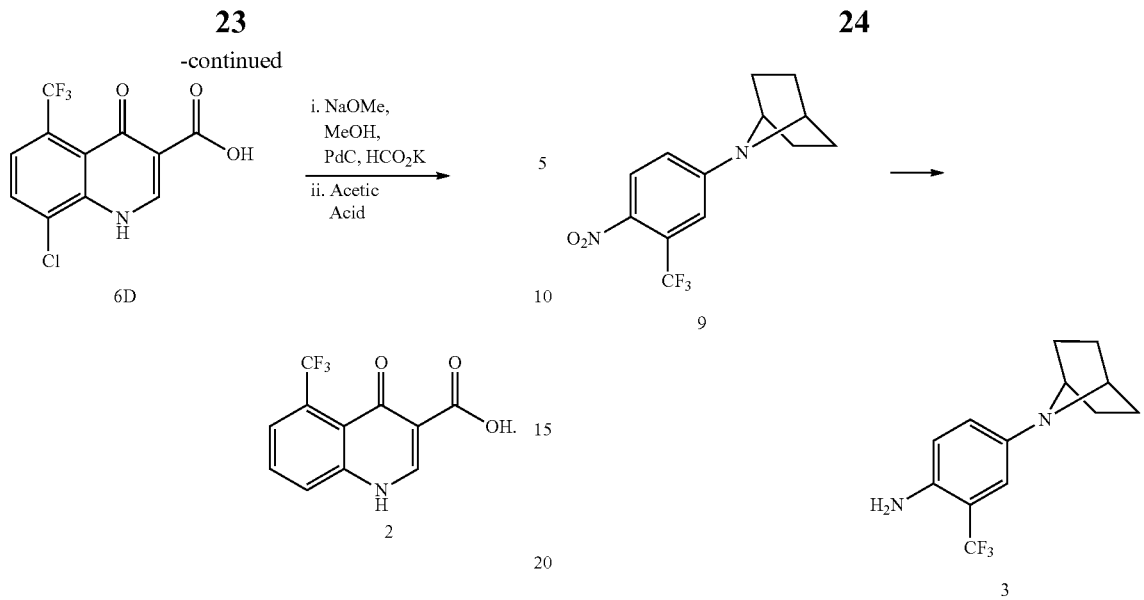

In another embodiment, the invention provides a method for preparing Compound 3

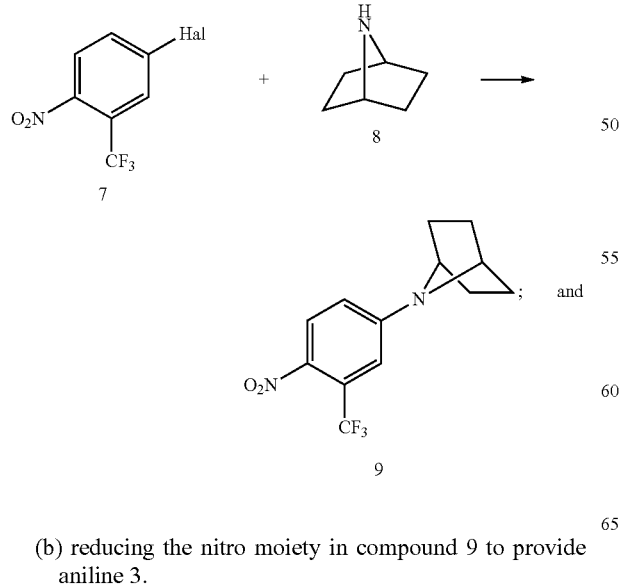

comprising:
(a) reacting compound 7, wherein Hal is F, Cl, Br or I, with 7-azabicyclo[2.2.1]heptane 8, or a salt thereof, to generate compound 9

(b) reducing the nitro moiety in compound 9 to provide aniline 3.

In one aspect of this embodiment, step (a) is performed in the presence of a base in a polar aprotic solvent. For example, the base is a tertiary amine bases such as triethyl amine, or diisopropylethyl amine or the like and the solvent such as acetonitrile.

In another aspect of this embodiment, step (b) is performed using hydrogen gas in the and a transition metal catalyst in an alcoholic solvent. For example, the catalyst comprises a group 9 or group 10 transition metal catalyst derived from Pt, Pd, or Ni. More particularly, the catalyst comprises Pd. The alcoholic solvent comprises an alcohol such as isopropanol, ethanol, methanol, or the like. For example, the solvent comprises ethanol.

In another embodiment, the invention provides a method for preparing Compound 3:

comprising:
(a) reacting Compound 7, wherein Hal is F, Cl, Br or I, with the hydrochloride salt of 7-azabicyclo[2.2.1]heptane (8-HCl) to generate compound 9

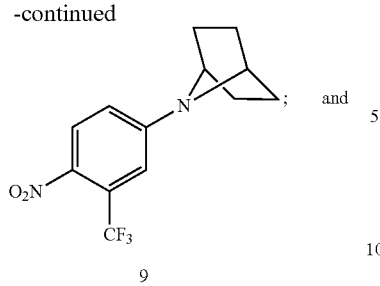
and (b) reducing the nitro moiety in Compound 9 to provide Compound 3.

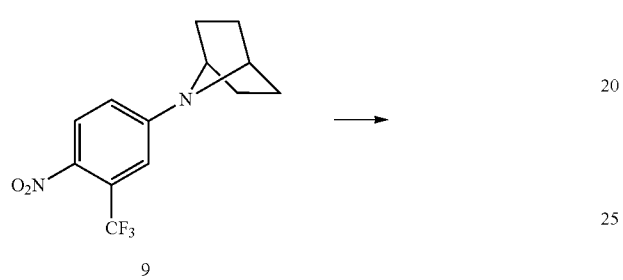

In one aspect of this embodiment, step (a) is performed in the presence of an inorganic carbonate base such as sodium carbonate and a polar aprotic solvent such as DMSO.

In another aspect of this embodiment, step (b) is performed using hydrogen gas in the and a transition metal catalyst in an alcoholic solvent. For example, the catalyst comprises a group 9 or group 10 transition metal catalyst derived from Pt, Pd, or Ni. More particularly, the catalyst comprises Pd. The alcoholic solvent comprises an alcohol such as isopropanol, ethanol, methanol, or the like. For example, the solvent comprises ethanol.

In another embodiment, the invention provides a method for preparing the hydrochloride salt 3-HCl:

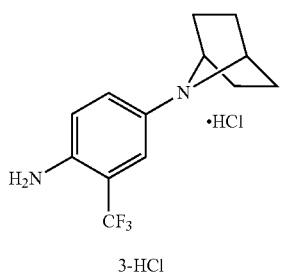 [SMILES: Nc1ccc(N2C3CCC2CC3)cc1C(F)(F)F ; Cl]

3-HCl comprising:
(a) reacting compound 7, wherein Hal is F, Cl, Br or I, with 7-azabicyclo[2.2.1]heptane hydrochloride salt 8-HCl to generate compound 9

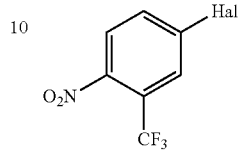 + 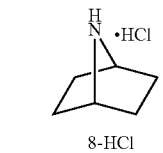 →

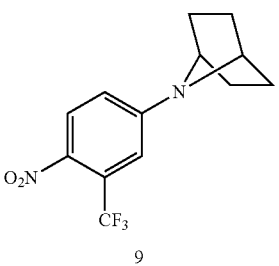

(b) reducing the nitro moiety in compound 9 to provide aniline 3;

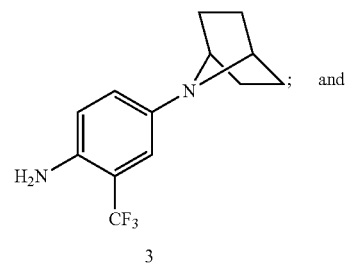

(c) treating the product of step (c) with HCl gas to provide 3-HCl.

In one aspect of this embodiment, step (a) is performed in the presence of an inorganic carbonate base such as sodium carbonate and a polar aprotic solvent such as DMSO.

In another aspect of this embodiment, step (b) is performed using hydrogen gas in the and a transition metal catalyst in an alcoholic solvent. For example, the catalyst comprises a group 9 or group 10 transition metal catalyst derived from Pt, Pd, or Ni. More particularly, the catalyst comprises Pd. The alcoholic solvent comprises an alcohol such as isopropanol, ethanol, methanol, or the like. For example, the solvent comprises ethanol.

In another embodiment, the invention includes a method for preparing Compound 8,

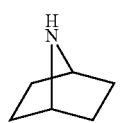

or a pharmaceutically acceptable salt thereof, comprising contacting trans-4-aminocyclohexanol with Boc anhydride to produce a compound of formula A

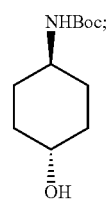

contacting a compound of formula A with methanesulfonic acid to produce a compound of formula B

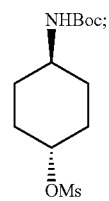

contacting a compound of formula B with trifluoroacetic acid to produce a compound of formula C

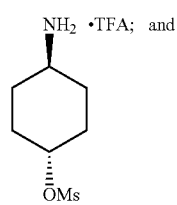

contacting a compound of formula C with hydroxide to produce a compound of formula 8.

In another embodiment, the invention includes a method of producing a compound of formula 8-HCl,

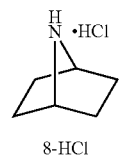

comprising contacting a compound of formula 8 with hydrochloric acid.

In one embodiment, the invention provides a process for producing Compound 3, comprising the steps of:

a) reacting Compound 7 with Compound 8-HCl in acetonitrile, in the presence of triethylamine at about 80° C. for about 16 hours to produce Compound 9; and b) hydrogenating Compound 9 in Ethanol, using Pd/C as a catalysts in the presence of hydrogen gas

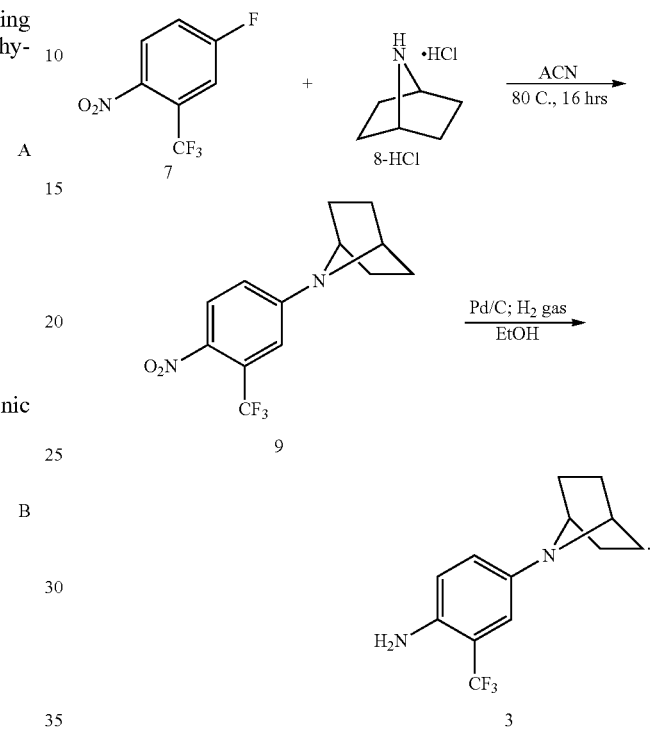

In one embodiment, the invention provides a process for producing Compound 3, comprising the steps of a) reacting Compound 7 with Compound 8-HCl in DMSO, in the presence of sodium carbonate at about 55° C. to produce Compound 9; and b) hydrogenating Compound 9 in Ethanol, using Pd/C as a catalysts in the presence of hydrogen gas

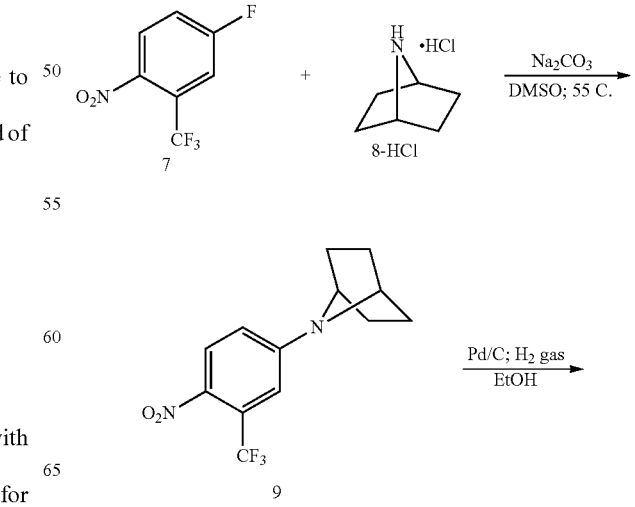

-continued

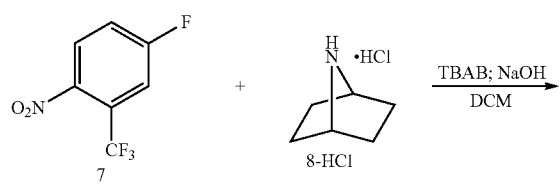
3

In one embodiment, the invention provides a process for producing Compound 3, comprising the steps of
a) reacting Compound 7 with Compound 8-HCl in dichloromethane, in the presence of sodium hydroxide and tetrabutylammonium bromide to produce Compound 9; and
b) hydrogenating Compound 9 in Ethanol, using Pd/C as a catalysts in the presence of hydrogen gas

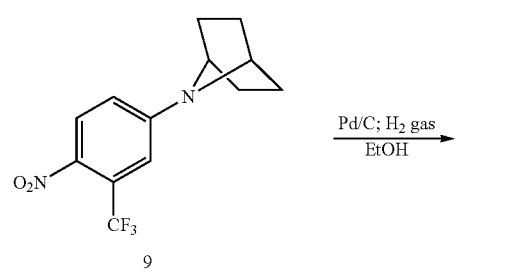

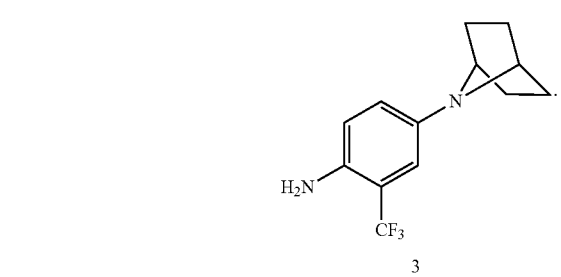
3

In one embodiment, the invention provides a process for producing Compound 3-HCl, comprising hydrogenating the hydrochloride salt of Compound 9 in 2-MeTHF in the presence of hydrogen gas using Pd/C as a catalyst.

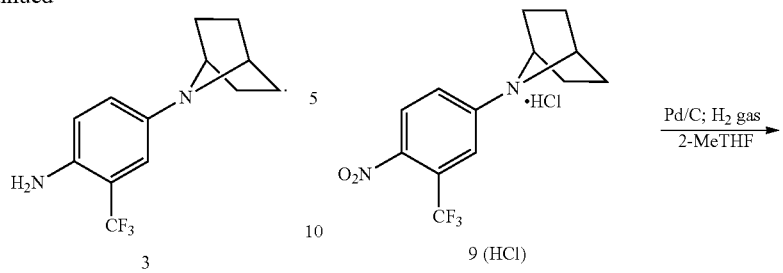
9 (HCl)

3-HCl

OTHER ASPECTS OF THE PRESENT INVENTION

In one aspect, the invention features a pharmaceutical composition comprising Compound 1 Form A, Compound 1 Form A-HCl, Compound 1 Form B, Compound 1 Form B-HCl, or any combination thereof, and a pharmaceutically acceptable adjuvant or carrier.

In one aspect, the present invention features a method of treating a CFTR mediated disease in a human comprising administering to the human an effective amount of Compound 1 Form A, Compound 1 Form A-HCl, Compound 1 Form B, Compound 1 Form B-HCl, or any combination thereof.

In some embodiments, the method comprises administering an additional therapeutic agent.

In certain embodiments, the present invention provides a method of treating diseases associated with reduced CFTR function due to mutations in the gene encoding CFTR or environmental factors (e.g., smoke). These diseases include, cystic fibrosis, asthma, smoke induced COPD, chronic bronchitis, rhinosinusitis, constipation, pancreatitis, pancreatic insufficiency, male infertility caused by congenital bilateral absence of the vas deferens (CBAVD), mild pulmonary disease, idiopathic pancreatitis, allergic bronchopulmonary aspergillosis (ABPA), liver disease, hereditary emphysema, hereditary hemochromatosis, coagulation-fibrinolysis deficiencies, such as protein C deficiency, Type 1 hereditary angioedema, lipid processing deficiencies, such as familial hypercholesterolemia, Type 1 chylomicronemia, abetalipoproteinemia, lysosomal storage diseases, such as I-cell disease/pseudo-Hurler, mucopolysaccharidoses, Sandhof/Tay-Sachs, Crigler-Najjar type H, polyendocrinopathy/hyperinsulemia, Diabetes mellitus, Laron dwarfism, myleoperoxidase deficiency, primary hypoparathyroidism, melanoma, glycanosis CDG type 1, congenital hyperthyroidism, osteogenesis imperfecta, hereditary hypofibrinogenemia, ACT deficiency, Diabetes insipidus (DI), neurophyseal DI, neprogenic DI, Charcot-Marie Tooth syndrome, Perlizaeus-Merzbacher disease, neurodegenerative diseases such as Alzheimer's disease, Parkinson's disease, amyotrophic lateral sclerosis, progressive supranuclear plasy, Pick's disease, several polyglutamine neurological disorders such as Huntington's, spinocerebullar ataxia type I, spinal and bulbar muscular atrophy, dentatorubal pallidoluysian, and myotonic dystrophy, as well as spongiform encephalopathies, such as hereditary Creutzfeldt-Jakob disease (due to prion protein processing defect), Fabry disease, Straussler-Scheinker syndrome, COPD, dry-eye disease, or Sjogren's disease, Osteoporosis, Osteopenia, bone healing and bone growth (including bone repair, bone regeneration, reducing bone resorption and increasing bone deposition), Gorham's Syndrome, chloride channelopathies such as myotonia congenita (Thomson and Becker forms), Bartter's syndrome type III, Dent's disease, hyperekplexia, epilepsy, hyperekplexia, lysosomal storage disease, Angelman syndrome, and Primary Ciliary Dyskinesia (PCD), a term for inherited disorders of the structure and/or function of cilia, including PCD with situs inversus (also known as Kartagener syndrome), PCD without situs inversus and ciliary aplasia.

In some embodiments, the method includes treating or lessening the severity of cystic fibrosis in a patient comprising administering to said patient one of the compositions as defined herein. In certain embodiments, the patient possesses mutant forms of human CFTR. In other embodiments, the patient possesses one or more of the following mutations ΔF508, R117H, and G551D of human CFTR. In one embodiment, the method includes treating or lessening the severity of cystic fibrosis in a patient possessing the ΔF508 mutation of human CFTR comprising administering to said patient one of the compositions as defined herein. In one embodiment, the method includes treating or lessening the severity of cystic fibrosis in a patient possessing the G551D mutation of human CFTR comprising administering to said patient one of the compositions as defined herein. In one embodiment, the method includes treating or lessening the severity of cystic fibrosis in a patient possessing the ΔF508 mutation of human CFTR on at least one allele comprising administering to said patient one of the compositions as defined herein. In one embodiment, the method includes treating or lessening the severity of cystic fibrosis in a patient possessing the ΔF508 mutation of human CFTR on both alleles comprising administering to said patient one of the compositions as defined herein. In one embodiment, the method includes treating or lessening the severity of cystic fibrosis in a patient possessing the G551D mutation of human CFTR on at least one allele comprising administering to said patient one of the compositions as defined herein. In one embodiment, the method includes treating or lessening the severity of cystic fibrosis in a patient possessing the G551D mutation of human CFTR on both alleles comprising administering to said patient one of the compositions as defined herein.

In some embodiments, the method includes lessening the severity of cystic fibrosis in a patient comprising administering to said patient one of the compositions as defined herein. In certain embodiments, the patient possesses mutant forms of human CFTR. In other embodiments, the patient possesses one or more of the following mutations ΔF508, R117H, and G551D of human CFTR. In one embodiment, the method includes lessening the severity of cystic fibrosis in a patient possessing the ΔF508 mutation of human CFTR comprising administering to said patient one of the compositions as defined herein. In one embodiment, the method includes lessening the severity of cystic fibrosis in a patient possessing the G551D mutation of human CFTR comprising administering to said patient one of the compositions as defined herein. In one embodiment, the method includes lessening the severity of cystic fibrosis in a patient possessing the ΔF508 mutation of human CFTR on at least one allele comprising administering to said patient one of the compositions as defined herein. In one embodiment, the method includes lessening the severity of cystic fibrosis in a patient possessing the ΔF508 mutation of human CFTR on both alleles comprising administering to said patient one of the compositions as defined herein. In one embodiment, the method includes lessening the severity of cystic fibrosis in a patient possessing the G551D mutation of human CFTR on at least one allele comprising administering to said patient one of the compositions as defined herein. In one embodiment, the method includes lessening the severity of cystic fibrosis in a patient possessing the G551D mutation of human CFTR on both alleles comprising administering to said patient one of the compositions as defined herein.

In some aspects, the invention provides a method of treating or lessening the severity of Osteoporosis in a patient comprising administering to said patient Compound 1 as described herein.

In certain embodiments, the method of treating or lessening the severity of Osteoporosis in a patient comprises administering to said patient a pharmaceutical composition as described herein.

In some aspects, the invention provides a method of treating or lessening the severity of Osteopenia in a patient comprising administering to said patient Compound 1 as described herein.

In certain embodiments, the method of treating or lessening the severity of Osteopenia in a patient comprises administering to said patient a pharmaceutical composition as described herein.

In some aspects, the invention provides a method of bone healing and/or bone repair in a patient comprising administering to said patient Compound 1 as described herein.

In certain embodiments, the method of bone healing and/or bone repair in a patient comprises administering to said patient a pharmaceutical composition as described herein.

In some aspects, the invention provides a method of reducing bone resorption in a patient comprising administering to said patient Compound 1 as described herein.

In certain embodiments, the method of reducing bone resorption in a patient comprises administering to said patient a pharmaceutical composition as described herein.

In some aspects, the invention provides a method of increasing bone deposition in a patient comprising administering to said patient Compound 1 as described herein.

In certain embodiments, the method of increasing bone deposition in a patient comprises administering to said patient a pharmaceutical composition as described herein.

In some aspects, the invention provides a method of treating or lessening the severity of COPD in a patient comprising administering to said patient Compound 1 as described herein.

In certain embodiments, the method of treating or lessening the severity of COPD in a patient comprises administering to said patient a pharmaceutical composition as described herein.

In some aspects, the invention provides a method of treating or lessening the severity of smoke induced COPD in a patient comprising administering to said patient Compound 1 as described herein.

In certain embodiments, the method of treating or lessening the severity of smoke induced COPD in a patient comprises administering to said patient a pharmaceutical composition as described herein.

In some aspects, the invention provides a method of treating or lessening the severity of chronic bronchitis in a patient comprising administering to said patient Compound 1 as described herein.

In certain embodiments, the method of treating or lessening the severity of chronic bronchitis in a patient comprises administering to said patient a pharmaceutical composition as described herein.

In one embodiment, the present invention provides a method of treating cystic fibrosis in a human, comprising administering to said human an effective amount of Compound 1 Form A, Form A-HCl, Form B, Form B-HCl, or any combination thereof.

In one aspect, the present invention features a pharmaceutical pack or kit comprising Compound 1 Form A, Form A-HCl, Form B, Form B-HCl, or any combination of these forms, and a pharmaceutically acceptable carrier.

In one aspect, the invention features a crystal form of N-(4-(7-azabicyclo[2.2.1]heptan-7-yl)-2-(trifluoromethyl)phenyl)-4-oxo-5-(trifluoromethyl)-1,4-dihydroquinoline-3-carboxamide having a trigonal crystal system, a R-3 space group, and the following unit cell dimensions: a=19.1670(4) Å, b=19.1670(4) Å, c=33.6572(12) Å, $\alpha=90°$, $\beta=90°$, and $\gamma=120°$.

In one embodiment, the present invention provides a crystal of N-(4-(7-azabicyclo[2.2.1]heptan-7-yl)-2-(trifluoromethyl)phenyl)-4-oxo-5-(trifluoromethyl)-1,4-dihydroquinoline-3-carboxamide in Form B having a monoclinic crystal system, a P21/c space group, and the following unit cell dimensions: a=13.5429(4) Å, b=13.4557(4) Å, c=12.0592(4) Å, $\alpha=90°$, $\beta=101.193°$, and $\gamma=90°$.

Uses, Formulation and Administration

In one aspect of the present invention, pharmaceutically acceptable compositions are provided, wherein these compositions comprise Form A as described herein, and optionally comprise a pharmaceutically acceptable carrier, adjuvant or vehicle. In certain embodiments, these compositions optionally further comprise one or more additional therapeutic agents.

As described above, the pharmaceutically acceptable compositions of the present invention additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention. Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Uses of Compounds and Pharmaceutically Acceptable Compositions

In yet another aspect, the present invention provides a method of treating or lessening the severity of a condition, disease, or disorder implicated by CFTR mutation. In certain embodiments, the present invention provides a method of treating a condition, disease, or disorder implicated by a deficiency of the CFTR activity, the method comprising administering composition comprising Compound 1 Form A, Form A-HCl, Form B, Form B-HCl, or any combination of these forms, to a subject, preferably a mammal, in need thereof.

In certain embodiments, the present invention provides a method of treating diseases associated with reduced CFTR function due to mutations in the gene encoding CFTR or environmental factors (e.g., smoke). These diseases include, cystic fibrosis, chronic bronchitis, recurrent bronchitis, acute bronchitis, male infertility caused by congenital bilateral absence of the vas deferens (CBAVD), female infertility caused by congenital absence of the uterus and vagina (CAUV), idiopathic chronic pancreatitis (ICP), idiopathic recurrent pancreatitis, idiopathic acute pancreatitis, chronic rhinosinusitis, primary sclerosing cholangitis, allergic bronchopulmonary aspergillosis, diabetes, dry eye, constipation, allergic bronchopulmonary aspergillosis (ABPA), bone diseases (e.g., osteoporosis), and asthma.

In certain embodiments, the present invention provides a method for treating diseases associated with normal CFTR function. These diseases include, chronic obstructive pulmonary disease (COPD), chronic bronchitis, recurrent bronchitis, acute bronchitis, rhinosinusitis, constipation, pancreatitis including chronic pancreatitis, recurrent pancreatitis, and acute pancreatitis, pancreatic insufficiency, male infertility caused by congenital bilateral absence of the vas deferens (CBAVD), mild pulmonary disease, idiopathic pancreatitis, liver disease, hereditary emphysema, gallstones, gastroesophageal reflux disease, gastrointestinal malignancies, inflammatory bowel disease, constipation, diabetes, arthritis, osteoporosis, and osteopenia.

In certain embodiments, the present invention provides a method for treating diseases associated with normal CFTR function including hereditary hemochromatosis, coagulation-fibrinolysis deficiencies, such as protein C deficiency, Type 1 hereditary angioedema, lipid processing deficiencies, such as familial hypercholesterolemia, Type 1 chylomicronemia, abetalipoproteinemia, lysosomal storage diseases, such as I-cell disease/pseudo-Hurler, mucopolysaccharidoses, Sandhof/Tay-Sachs, Crigler-Najjar type II, polyendocrinopathy/hyperinsulemia, Diabetes mellitus, Laron dwarfism, myleoperoxidase deficiency, primary hypoparathyroidism, melanoma, glycanosis CDG type 1, congenital hyperthyroidism, osteogenesis imperfecta, hereditary hypofibrinogenemia, ACT deficiency, Diabetes insipidus (DI), neurophyseal DI, neprogenic DI, Charcot-Marie Tooth syndrome, Perlizaeus-Merzbacher disease, neurodegenerative diseases such as Alzheimer's disease, Parkinson's disease, amyotrophic lateral sclerosis, progressive supranuclear palsy, Pick's disease, several polyglutamine neurological disorders such as Huntington's, spinocerebullar ataxia type I, spinal and bulbar muscular atrophy, dentatorubal pallidoluysian, and myotonic dystrophy, as well as spongiform encephalopathies, such as hereditary Creutzfeldt-Jakob disease (due to prion protein processing defect), Fabry disease, Straussler-Scheinker syndrome, Gorham's Syndrome, chloride channelopathies, myotonia congenita (Thomson and Becker forms), Bartter's syndrome type III, Dent's disease, hyperekplexia, epilepsy, hyperekplexia, lysosomal storage disease, Angelman syndrome, Primary Ciliary Dyskinesia (PCD), PCD with situs inversus (also known as Kartagener syndrome), PCD without situs inversus and ciliary aplasia, or Sjogren's disease, comprising the step of administering to said mammal an effective amount of a composition comprising Compound 1 Form A, Compound 1 Form A-HCl, Compound 1 Form B, Compound 1 Form B-HCl, or any combination of these forms, described herein.

According to an alternative preferred embodiment, the present invention provides a method of treating cystic fibrosis comprising the step of administering to said mammal a composition comprising the step of administering to said mammal an effective amount of a composition comprising Compound 1 Form A, Compound 1 Form A-HCl, Compound 1 Form B, Compound 1 Form B-HCl, or any combination of these forms, described herein.

According to the invention an "effective amount" of Compound 1 Form A, Compound 1 Form A-HCl, Compound 1 Form B, Compound 1 Form B-HCl, any combination of these forms, or a pharmaceutically acceptable composition thereof is that amount effective for treating or lessening the severity of one or more of the diseases, disorders or conditions as recited above.

Compound 1 Form A, Compound 1 Form A-HCl, Compound 1 Form B, Compound 1 Form B-HCl, or any combination of these forms, or a pharmaceutically acceptable composition thereof may be administered using any amount and any route of administration effective for treating or lessening the severity of one or more of the diseases, disorders or conditions as recited above.

In certain embodiments, Compound 1 Form A, Compound 1 Form A-HCl, Compound 1 Form B, Compound 1 Form B-HCl, any combination of these forms, or a pharmaceutically acceptable composition thereof is useful for treating or lessening the severity of cystic fibrosis in patients who exhibit residual CFTR activity in the apical membrane of respiratory and non-respiratory epithelia. The presence of residual CFTR activity at the epithelial surface can be readily detected using methods known in the art, e.g., standard electrophysiological, biochemical, or histochemical techniques. Such methods identify CFTR activity using in vivo or ex vivo electrophysiological techniques, measurement of sweat or salivary CF concentrations, or ex vivo biochemical or histochemical techniques to monitor cell surface density. Using such methods, residual CFTR activity can be readily detected in patients heterozygous or homozygous for a variety of different mutations, including patients homozygous or heterozygous for the most common mutation, ΔF508.

In another embodiment, Compound 1 Form A, Compound 1 Form A-HCl, Compound 1 Form B, Compound 1 Form B-HCl, or any combination of these forms, described herein or a pharmaceutically acceptable composition thereof is useful for treating or lessening the severity of cystic fibrosis in patients who have residual CFTR activity induced or augmented using pharmacological methods or gene therapy. Such methods increase the amount of CFTR present at the cell surface, thereby inducing a hitherto absent CFTR activity in a patient or augmenting the existing level of residual CFTR activity in a patient.

In one embodiment, Compound 1 Form A, Compound 1 Form A-HCl, Compound 1 Form B, Compound 1 Form B-HCl, or any combination of these forms, described herein, or a pharmaceutically acceptable composition thereof is useful for treating or lessening the severity of cystic fibrosis in patients within certain genotypes exhibiting residual CFTR activity, e.g., class III mutations (impaired regulation or gating), class N mutations (altered conductance), or class V mutations (reduced synthesis) (Lee R. Choo-Kang, Pamela L., Zeitlin, Type I, II, III, IV, and V cystic fibrosis Transmembrane Conductance Regulator Defects and Opportunities of Therapy; Current Opinion in Pulmonary Medicine 6:521-529, 2000). Other patient genotypes that exhibit residual CFTR activity include patients homozygous for one of these classes or heterozygous with any other class of mutations, including class I mutations, class II mutations, or a mutation that lacks classification.

In one embodiment, Compound 1 Form A, Compound 1 Form A-HCl, Compound 1 Form B, Compound 1 Form B-HCl, or any combination of these forms described herein or a pharmaceutically acceptable composition thereof is useful for treating or lessening the severity of cystic fibrosis in patients within certain clinical phenotypes, e.g., a moderate to mild clinical phenotype that typically correlates with the amount of residual CFTR activity in the apical membrane of epithelia. Such phenotypes include patients exhibiting pancreatic insufficiency or patients diagnosed with idiopathic pancreatitis and congenital bilateral absence of the vas deferens, or mild lung disease.

The exact amount required will vary from subject to subject, depending on the species, age, and general condition of the subject, the severity of the infection, the particular agent, its mode of administration, and the like. The compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

The pharmaceutically acceptable compositions of this invention can be administered to humans and other animals orally, rectally, parenterally, intracisternally, intravaginally, intraperitoneally, topically (as by powders, ointments, drops or patch), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 0.5 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in microencapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, eardrops, and eye drops are also contemplated as being within the scope of this invention. Additionally, the present invention contemplates the use of transdermal patches, which have the added advantage of providing controlled delivery of a compound to the body. Such dosage forms are prepared by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

It will also be appreciated that the Form A, Form A-HCl, Form B, Form B-HCl, or any combination thereof described herein or a pharmaceutically acceptable composition thereof can be employed in combination therapies, that is, Form A, Form A-HCl, Form B, Form B-HCl, or any combination thereof described herein or a pharmaceutically acceptable composition thereof can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another agent used to treat the same disorder), or they may achieve different effects (e.g., control of any adverse effects). As used herein, additional therapeutic agents that are normally administered to treat or prevent a particular disease, or condition, are known as "appropriate for the disease, or condition, being treated."

In one embodiment, the additional agent is selected from a mucolytic agent, bronchodialator, an anti-biotic, an anti-infective agent, an anti-inflammatory agent, a CFTR modulator other than a compound of the present invention, or a nutritional agent.

In one embodiment, the additional agent is an antibiotic. Exemplary antibiotics useful herein include tobramycin, including tobramycin inhaled powder (TIP), azithromycin, aztreonam, including the aerosolized form of aztreonam, amikacin, including liposomal formulations thereof, ciprofloxacin, including formulations thereof suitable for administration by inhalation, levoflaxacin, including aerosolized formulations thereof, and combinations of two antibiotics, e.g., fosfomycin and tobramycin.

In another embodiment, the additional agent is a mucolyte. Exemplary mucolytes useful herein includes Pulmozyme®.

In another embodiment, the additional agent is a bronchodialator. Exemplary bronchodialtors include albuterol, metaprotenerol sulfate, pirbuterol acetate, salmeterol, or tetrabuline sulfate.

In another embodiment, the additional agent is effective in restoring lung airway surface liquid. Such agents improve the movement of salt in and out of cells, allowing mucus in the lung airway to be more hydrated and, therefore, cleared more easily. Exemplary such agents include hypertonic saline, denufosol tetrasodium ([[(3S,5R)-5-(4-amino-2-oxopyrimidin-1-yl)-3-hydroxyoxolan-2-yl]methoxy-hydroxyphosphoryl][[[(2R,3S,4R,5R)-5-(2,4-dioxopyrimidin-1-yl)-3,4-dihydroxyoxolan-2-yl]methoxy-hydroxyphosphoryl]oxy-hydroxyphosphoryl]hydrogen phosphate), or bronchitol (inhaled formulation of mannitol).

In another embodiment, the additional agent is an anti-inflammatory agent, i.e., an agent that can reduce the inflammation in the lungs. Exemplary such agents useful herein include ibuprofen, docosahexanoic acid (DHA), sildenafil, inhaled glutathione, pioglitazone, hydroxychloroquine, or simavastatin.

In another embodiment, the additional agent reduces the activity of the epithelial sodium channel blocker (ENaC) either directly by blocking the channel or indirectly by modulation of proteases that lead to an increase in ENaC activity (e.g., seine proteases, channel-activating proteases). Exemplary such agents include camostat (a trypsin-like protease inhibitor), QAU145, 552-02, GS-9411, INO-4995, Aerolytic, and amiloride. Additional agents that reduce the activity of the epithelial sodium channel blocker (ENaC) can be found, for example, in PCT Publication No. WO2009/074575, the entire contents of which are incorporated herein in their entirety.

Amongst other diseases described herein, combinations of CFTR modulators, such as those described herein, and agents that reduce the activity of ENaC are use for treating Liddle's syndrome, an inflammatory or allergic condition including cystic fibrosis, primary ciliary dyskinesia, chronic bronchitis, chronic obstructive pulmonary disease, asthma, respiratory tract infections, lung carcinoma, xerostomia and keratoconjunctivitis sire, respiratory tract infections (acute and chronic; viral and bacterial) and lung carcinoma.

Combinations of CFTR modulators, such as those described herein, and agents that reduce the activity of ENaC are also useful for treating diseases mediated by blockade of the epithelial sodium channel also include diseases other than respiratory diseases that are associated with abnormal fluid regulation across an epithelium, perhaps involving abnormal physiology of the protective surface liquids on their surface, e.g., xerostomia (dry mouth) or keratoconjunctivitis sire (dry eye). Furthermore, blockade of the epithelial sodium channel in the kidney could be used to promote diuresis and thereby induce a hypotensive effect.

Asthma includes both intrinsic (non-allergic) asthma and extrinsic (allergic) asthma, mild asthma, moderate asthma, severe asthma, bronchitic asthma, exercise-induced asthma, occupational asthma and asthma induced following bacterial infection. Treatment of asthma is also to be understood as embracing treatment of subjects, e.g., of less than 4 or 5 years of age, exhibiting wheezing symptoms and diagnosed or diagnosable as "wheezy infants", an established patient category of major medical concern and now often identified as incipient or early-phase asthmatics. (For convenience this particular asthmatic condition is referred to as "wheezy-infant syndrome".) Prophylactic efficacy in the treatment of asthma will be evidenced by reduced frequency or severity of symptomatic attack, e.g., of acute asthmatic or bronchoconstrictor attack, improvement in lung function or improved airways hyperreactivity. It may further be evidenced by reduced requirement for other, symptomatic therapy, i.e., therapy for or intended to restrict or abort symptomatic attack when it occurs, e.g., anti-inflammatory (e.g., cortico-steroid) or bronchodilatory. Prophylactic benefit in asthma may, in particular, be apparent in subjects prone to "morning dipping". "Morning dipping" is a recognized asthmatic syndrome, common to a substantial percentage of asthmatics and characterized by asthma attack, e.g., between the hours of about 4-6 am, i.e., at a time normally substantially distant from any previously administered symptomatic asthma therapy.

Chronic obstructive pulmonary disease includes chronic bronchitis or dyspnea associated therewith, emphysema, as well as exacerbation of airways hyperreactivity consequent to other drug therapy, in particular, other inhaled drug therapy. In some embodiments, the combinations of CFTR modulators, such as those described herein, and agents that reduce the activity of ENaC are useful for the treatment of bronchitis of whatever type or genesis including, e.g., acute, arachidic, catarrhal, croupus, chronic or phthinoid bronchitis.

In another embodiment, the additional agent is a CFTR modulator other than Form A, Form B, Form B-HCl, and Form A-HCl, i.e., an agent that has the effect of modulating CFTR activity. Exemplary such agents include ataluren ("PTC124®"; 3-[5-(2-fluorophenyl)-1,2,4-oxadiazol-3-yl]

benzoic acid), sinapultide, lancovutide, depelestat (a human recombinant neutrophil elastase inhibitor), cobiprostone (7-{(2R,4aR,5R,7aR)-2-[(3S)-1,1-difluoro-3-methylpentyl]-2-hydroxy-6-oxooctahydrocyclopenta[b]pyran-5-yl}heptanoic acid), or (3-(6-(1-(2,2-difluorobenzo[d][1,3]dioxol-5-yl)cyclopropanecarboxamido)-3-methylpyridin-2-yl)benzoic acid. In another embodiment, the additional agent is (3-(6-(1-(2,2-difluorobenzo[d][1,3]dioxol-5-yl)cyclopropanecarboxamido)-3-methylpyridin-2-yl)benzoic acid.

In another embodiment, the additional agent is a nutritional agent. Exemplary such agents include pancrelipase (pancreating enzyme replacement), including Pancrease®, Pancreacarb®, Ultrase®, or Creon®, Liprotomase® (formerly Trizytek®), Aquadeks®, or glutathione inhalation. In one embodiment, the additional nutritional agent is pancrelipase.

In one embodiment, the additional agent is a CFTR modulator other than a compound of the present invention.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

Compound 1 Form A, Form A-HCl, Form B, Form B-HCl, or any combination thereof described herein or a pharmaceutically acceptable composition thereof may also be incorporated into compositions for coating an implantable medical device, such as prostheses, artificial valves, vascular grafts, stents and catheters. Accordingly, the present invention, in another aspect, includes a composition for coating an implantable device comprising a compound of the present invention as described generally above, and in classes and subclasses herein, and a carrier suitable for coating said implantable device. In still another aspect, the present invention includes an implantable device coated with a composition comprising a compound of the present invention as described generally above, and in classes and subclasses herein, and a carrier suitable for coating said implantable device. Suitable coatings and the general preparation of coated implantable devices are described in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccharides, polyethylene glycol, phospholipids or combinations thereof to impart controlled release characteristics in the composition.

Another aspect of the invention relates to modulating CFTR activity in a biological sample or a patient (e.g., in vitro or in vivo), which method comprises administering to the patient, or contacting said biological sample with Compound 20 Form A, Form A-HCl, Form B, Form B-HCl, or any combination thereof described herein or a pharmaceutically acceptable composition thereof. The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Modulation of CFTR in a biological sample is useful for a variety of purposes that are known to one of skill in the art. Examples of such purposes include, but are not limited to, the study of CFTR in biological and pathological phenomena; and the comparative evaluation of new modulators of CFTR.

In yet another embodiment, a method of modulating activity of an anion channel in vitro or in vivo, is provided comprising the step of contacting said channel with Compound 20 Form A, Form A-HCl, Form B, Form B-HCl, or any combination thereof described herein or a pharmaceutically acceptable composition thereof. In preferred embodiments, the anion channel is a chloride channel or a bicarbonate channel. In other preferred embodiments, the anion channel is a chloride channel.

According to an alternative embodiment, the present invention provides a method of increasing the number of functional CFTR in a membrane of a cell, comprising the step of contacting said cell with Compound 20 Form A, Form A-HCl, Form B, Form B-HCl, or any combination thereof described herein or a pharmaceutically acceptable composition thereof.

According to another preferred embodiment, the activity of the CFTR is measured by measuring the transmembrane voltage potential. Means for measuring the voltage potential across a membrane in the biological sample may employ any of the known methods in the art, such as optical membrane potential assay or other electrophysiological methods.

The optical membrane potential assay utilizes voltage-sensitive FRET sensors described by Gonzalez and Tsien (See, Gonzalez, J. E. and R. Y. Tsien (1995) "Voltage sensing by fluorescence resonance energy transfer in single cells." Biophys J 69(4): 1272-80, and Gonzalez, J. E. and R.Y. Tsien (1997); "Improved indicators of cell membrane potential that use fluorescence resonance energy transfer" Chem Biol 4(4): 269-77) in combination with instrumentation for measuring fluorescence changes such as the Voltage/Ion Probe Reader (VIPR) (See, Gonzalez, J. E., K. Oades, et al. (1999) "Cell-based assays and instrumentation for screening ion-channel targets" Drug Discov Today 4(9): 431-439).

These voltage sensitive assays are based on the change in fluorescence resonant energy transfer (FRET) between the membrane-soluble, voltage-sensitive dye, $DiSBAC_2(3)$, and a fluorescent phospholipid, CC2-DMPE, which is attached to the outer leaflet of the plasma membrane and acts as a FRET donor. Changes in membrane potential ($V_m$) cause the negatively charged $DiSBAC_2(3)$ to redistribute across the plasma membrane and the amount of energy transfer from CC2-DMPE changes accordingly. The changes in fluorescence emission can be monitored using VIPR™ II, which is an integrated liquid handler and fluorescent detector designed to conduct cell-based screens in 96- or 384-well microtiter plates.

In another aspect the present invention provides a kit for use in measuring the activity of CFTR or a fragment thereof in a biological sample in vitro or in vivo comprising (i) a composition comprising Compound 20 Form A, Form A-HCl, Form B, Form B-HCl, or any combination thereof or any of the above embodiments; and (ii) instructions for a) contacting the composition with the biological sample and b) measuring activity of said CFTR or a fragment thereof. In one embodiment, the kit further comprises instructions for a) contacting an additional composition with the biological sample; b) measuring the activity of said CFTR or a fragment thereof in the presence of said additional compound, and c) comparing the activity of the CFTR in the presence of the additional compound with the density of the CFTR in the presence of Form A, Form A-HCl, Form B, Form B-HCl, or any combination thereof described herein. In preferred embodiments, the kit is used to measure the density of CFTR.

In order that the invention described herein may be more fully understood, the following examples are set forth. It should be understood that these examples are for illustrative purposes only and are not to be construed as limiting this invention in any manner.

EXAMPLES

Methods & Materials

XRPD (X-Ray Powder Diffraction)

Instrument 1

X-ray powder diffraction (XRPD) data are recorded at room temperature using a Rigaku/MSC MiniFlex Desktop Powder X-ray Diffractometer (Rigaku, The Woodlands, Tex.). The X-Ray is generated using Cu tube operated at 30 kV and 15 mA with Kβ suppression filter. The divergence slit is variable with the scattering and receiving slits set at 4.2 degree and slit 0.3 mm, respectively. The scan mode is fixed time (FT) with 0.02 degree step width and count time of 2.0 seconds. The Powder X-ray Diffractometer is calibrated using reference standard: 75% Sodalite ($Na_3Al_4Si_4O_{12}Cl$) and 25% Silicon (Rigaku, Cat#2100/ALS). The six samples stage is used with zero background sample holders (SH-LBSI511-RNDB). The powder sample is placed on the indented area and flattened with glass slide.

Instrument 2

Alternatively, the powder x-ray diffraction measurements were performed using PANalytical's X-pert Pro diffractometer at room temperature with copper radiation (1.54060 A). The incident beam optic was comprised of a variable divergence slit to ensure a constant illuminated length on the sample and on the diffracted beam side. A fast linear solid state detector was used with an active length of 2.12 degrees 2 theta measured in a scanning mode. The powder sample was packed on the indented area of a zero background silicon holder and spinning was performed to achieve better statistics. A symmetrical scan was measured from 4-40 degrees 2 theta with a step size of 0.017 degrees and a scan step time of 15.5 s.

Instrument 3

Alternatively, high resolution data were collected at room temperature at the beamline ID31 (European Synchrotron Radiation Facility in Grenoble, France) The X-rays are produced by three 11-mm-gap ex-vacuum undulators. The beam is monochromated by a cryogenically cooled double-crystal monochromator (Si(111) crystals). Water-cooled slits define the size of the beam incident on the monochromator, and of the monochromatic beam transmitted to the sample in the range of 0.5 to 2.5 mm (horizontal) by 0.1 to 1.5 mm (vertical). The wavelength used for the experiment was 1.29984 (3) Å. The diffractometer consists of a bank of nine detectors which is scanned vertically to measure the diffracted intensity as a function of 2θ. Each detector is preceded by a Si(111) analyser crystal and the detector channels are approximately 2° apart. This diffractometer is capable of producing very precise high resolution diffraction patterns with peak widths as low as 0.003°, and accuracy of peak positions is in the order of 0.0001°. The powder diffraction data were processed and indexed using Materials Studio (Reflex module). The structure was solved using PowderSolve module of Materials Studio. The resulting solution was assessed for structural viability and subsequently refined using Rietveld refinement procedure.

The XPRD spectra described in the examples for Form A and Form B were recorded using Instrument 1 (FIG. 10A) or Instrument 2 (FIG. 10B) with the settings described above. XPRD spectra described in the examples for Form B-HCl, and Form A-HCl were recorded using Instrument 2 with the settings described above. The crystal system, space group and unit cell dimensions for Form A-HCl and Form B-HCl were determined using instrument 3.

Differential Scanning Calorimetry (DSC)

Differential Scanning calorimetry (DSC) was performed using TA DSC Q2000 differential scanning calorimeter (TA Instruments, New Castle, Del.). The instrument was calibrated with indium. Samples of approximately 2-3 mg were weighed into hermetic pans that were crimped using lids with one hole. The DSC samples were scanned from 25° C. to 315° C. at a heating rate of 10° C./min. Data was collected by Thermal Advantage Q Series™ software and analyzed by Universal Analysis software (TA Instruments, New Castle, Del.).

Thermogravimetric Analysis (TGA)

Thermogravimetric Analysis (TGA) data were collected on a TA Q500 Thermogravimetric Analyzer (TA Instruments, New Castle, Del.). A sample with weight of approximately 3-5 mg was scanned from 25° C. to 350° C. at a heating rate of 10° C./min. Data were collected by Thermal Advantage Q Series™ software and analyzed by Universal Analysis software (TA Instruments, New Castle, Del.).

FTIR Spectroscopy

FTIR spectra were collected from a Thermo Scientific, Nicolet 6700 FT-IR spectrometer, with smart orbit sampling compartment (multi-bounce Attenuated Total Reflection accessory), diamond window at 45 degrees. The Software used for data collection and analysis is: Omnic, 7.4. The collection settings were as follows:

Detector: DTGS KBr;
Beamsplitter: Ge on KBr;
Source: EverGlo IR;
Scan range: 4000—400 $cm^{-1}$;
Gain: 8.0;
Optical velocity: 0.6329 cm/sec;
Aperture: 100;
No. of scans: 32; and
Resolution: 4 $cm^{-1}$ The powder sample was placed directly on the diamond crystal and pressure was added to conform the surface of the sample to the surface of the diamond crystal. The background spectrum was collected and then the sample spectrum was collected.

Solid State Nuclear Magnetic Spectroscopy

Solid state nuclear magnetic spectroscopy (SSNMR) spectra were acquired on Bruker 400 MHz proton frequency wide bore spectrometer. Proton relaxation longitudinal relaxation times ($^1H\ T_1$) were obtained by fitting proton detected proton saturation recovery data to an exponential function. These values were used to set an optimal recycle delay of carbon cross-polarization magic angle spinning experiment ($^{13}C$ CPMAS), which, typically, was set between 1.233 $^1H\ T_1$ and 1.5×$^1H\ T_1$. The carbon spectra were acquired with 2 ms contact time using linear amplitude ramp on proton channel (from 50% to 100%) and 100 kHz TPPM decoupling. The typical magic angle spinning (MAS) speed was 15.0 kHz. Fluorine spectra were obtained using proton decoupled, direct polarization MAS experiment. 100 kHz TPPM decoupling was used. The recycle delay was set to ≥5×$^{19}F\ T_1$. The fluorine longitudinal relaxation time ($^{19}F\ T_1$) was obtained by fitting fluorine detected, proton decoupled saturation recovery data to an exponential function. Carbon as well as fluorine spectra were externally referenced using the upfield resonance of solid phase adamantane which was set to 29.5 ppm. Using this procedure, carbon spectra were indirectly referenced to tetramethyl silane at 0 ppm and fluorine spectra were indirectly referenced to nitromethane at 0 ppm.

Synthetic Examples

Preparative Example 7-azabicyclo[2.2.1]heptane hydrochloride (8-HCl)

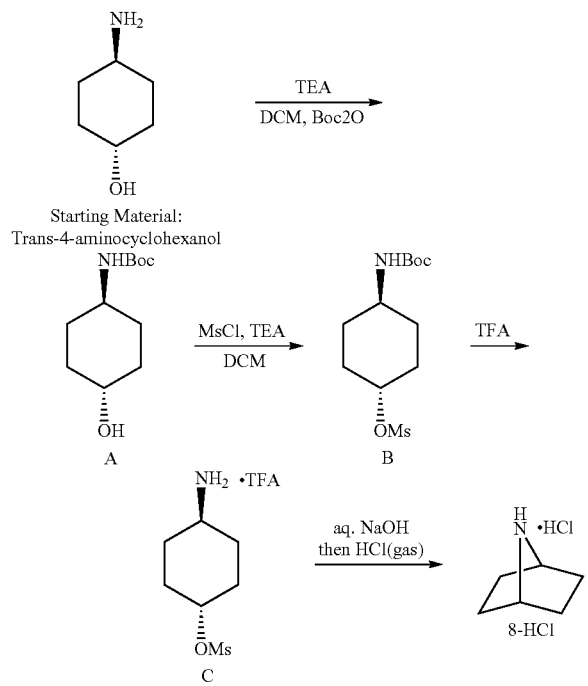

Preparation of trans-4-(tert-butoxycarbonylamino)cyclohexanol (A), method 1

Sodium carbonate (920.2 g, 8.682 mol, 2 eq) was added to a reaction vessel followed by an addition of water (3.000 L, 6 vol) and stirring. Dichloromethane (DCM, 4.000 L, 4 vol) was added followed by trans-4-aminocyclohexanol (500.0 g, 4.341 mol) to generate a biphasic reaction mixture that was vigorously stirred at room temperature. A solution of Boc$_2$O (947.4 g, 997.3 mL, 4.341 mol, 1 eq) in DCM (2 vol) was then rapidly added dropwise to the vessel, and the resulting reaction mixture was stirred at room temperature overnight. The reaction mixture was then filtered and the filter cake was washed with water (2×8 vol). The product was suction-dried until it was a compact cake. The cake was then dried in a vacuum oven at 35° C. for 24 h giving 830 g of trans-4-(tert-butoxycarbonylamino)cyclohexanol (A) as a crystalline solid.

Preparation of trans-4-(tert-butoxycarbonylamino)cyclohexanol (A), method 2

Two 50 L three-neck round bottom flasks were each equipped with a mechanical stirrer and thermocouple. The flasks were placed in a cooling tub, and then each flask was charged with water (8.87 L) and trans-4-aminocyclohexanol (1479 g). After about 10 to 30 minutes, the trans-4-aminocyclohexanol had dissolved, and potassium carbonate (1774.6 g) was added to each flask. After about 10 to 20 minutes, the potassium carbonate had dissolved, and DCM (2.96 L) was charged to each flask. Boc anhydride (3082.6 g) in DCM (1479 mL) was then added to each flask at such a rate as to maintain the temperature at 20 to 30° C. An ice/water bath was used to control the exotherm and to accelerate the addition, which took approximately 1 to 2 hours. A suspension formed during the addition, and the reaction mixtures were allowed to warm to room temperature and stirred overnight, until the reaction was complete based on the disappearance of the Boc anhydride. Heptane (6 L) was then charged to each flask, and the mixtures were cooled to approximately 0 to 5° C. Solids were collected from each flask by filtration using the same filter. The combined solids were washed with heptane (6 L) followed by water (8 L). The solids were charged to an appropriately sized crock equipped with a mechanical stirrer. Water (12 L) and heptane (6 L) were added, and the resulting suspension was mechanically stirred for 30 to 60 minutes. The solids were collected by filtration and then washed on a filter with water (8 L) and heptane (8 L), air-dried on a filter for three days, and then dried under vacuum at 30 to 35° C. to a constant weight to provide the product as a white solid.

Preparation of trans-4-(tert-butoxycarbonylamino)cyclohexylmethanesulfonate (B), method 1

A 12 L flask was equipped with a nitrogen flow and a mechanical stirrer. Trans-4-(tert-butoxycarbonylamino)cyclohexanol (750 g, 3.484 mol) was introduced, followed by tetrahydrofuran (THF, 6.000 L, 8 vol), and the mixture was stirred. Triethylamine (370.2 g, 509.9 mL, 3.658 mol, 1.05 eq) was added and the mixture was cooled to 0° C. Methanesulfonyl chloride (419.0 g, 283.1 mL, 3.658 mol, 1.05 eq) was carefully added dropwise, keeping the temperature of the mixture below 5° C. After the addition, the mixture was stirred at 0° C. for 3 h, and then gradually warmed to room temperature (17° C.) and stirred overnight (about 15 h). The mixture was quenched with water (6 vol) and stirred for 15 min. Ethyl acetate (EtOAc, 9.000 L, 12 vol) was added and the stirring was continued for 15 min. The stirring was stopped and the mixture was allowed to stand for 10 min, and the aqueous phase was removed. 1 N HCl (6 vol, 4.5 L) was added and stirring was continued for 15 min. The stirring stopped and the aqueous phase was removed. 10% w/v NaHCO$_3$ (4.5 L, 6 vol) was added and the mixture stirred for 10 min. Stirring was stopped and the aqueous phase was removed. Water (6 vol, 4.5 L) was added and the mixture was stirred for 10 min. The aqueous layer was removed, and the organic layer was polish filtered and concentrated to 4 vol. Heptane (5.5 vol, 4 L) was added and the mixture was concentrated again to dryness resulting in 988 g of trans-4-(tert-butoxycarbonylamino)cyclohexylmethanesulfonate.

Preparation of trans-4-(tert-butoxycarbonylamino)cyclohexylmethanesulfonate (B), method 2

A three-neck round bottom flask equipped with a mechanical stirrer, addition funnel, nitrogen inlet, thermocouple and drying tube was placed into a cooling tub. Trans-4-(tert-butoxycarbonylamino)cyclohexanol (2599 g, 12.07 mol, 1.0 eq), tetrahydrofuran (THF) (20.8 L), and triethylamine (1466 g, 14.49 mol, 1.2 eq) were added to the flask. The mixture was cooled with an ice water bath and stirred. Methanesulfonyl chloride (1466 g, 12.80 mol, 1.06 eq) was added dropwise by addition funnel over 1 hour. Once the addition was complete, the cooling bath was removed, and the reaction mixture was stirred until TLC indicated the starting material was consumed (about 30 minutes). The reaction mixture was then quenched with an aqueous solution of hydrochloric acid (223 mL of HCl in 6.7 L of water) and EtOAc (10.4 L). The mixture was stirred for approximately 10 to 20 minutes at ambient temperature and then was transferred to a sepratory funnel. The layers were separated, and the aqueous layer discarded. The organic layer was washed with water (2×4.5 L), aqueous saturated sodium bicarbonate solution (1×4.5 L), and dried over anhydrous magnesium sulfate with stirring for 5 to 10 minutes. The mixture was filtered and the filter cake was washed with EtOAc (2×600 mL). The combined washes and filtrate were concentrated under reduced pressure at 40° C., leaving a white solid. The solid was taken up in heptane (3 L) and cooled in an ice/methanol cooling tub. More heptane (5 L) was added, and the mixture was stirred at 0 to 5° C. for not less than 1 hour. The solids were then collected by filtration, washed with cold heptane (0 to 5° C., 2×1.3 L), and dried under vacuum at 40° C. to a constant weight to provide the captioned compound.

Note: A jacketed reactor may be used instead of a round bottom flask with a cooling tub and ice bath.

Preparation of
trans-4-aminocyclohexylmethanesulfonate (C),
method 1

Trans-4-(tert-butoxycarbonylamino)cyclohexylmethanesulfonate (985 g, 3.357 mol) was introduced into a 3-neck 12 L flask equipped with a stirrer under a nitrogen atmosphere and open vent. DCM (1.970 L, 2 vol) was added at room temperature, and stirring was commenced. Trifluoroacetic acid (TFA) (2.844 kg, 1.922 L, 24.94 mol, 2 vol) was slowly added to the mixture in two batches of 1 L each. After the first addition, the mixture was stirred for 30 min followed by a second addition. The mixture was stirred overnight (15 h) at room temperature resulting in a clear solution. 2-methyltetrahydrofuran (4 vol) was then added to the reaction mixture, which was stirred for 1 h. The mixture was then carefully filtered in a fume hood and suction dried to generate 1100 g of TFA salt of trans-4-aminocyclohexylmethanesulfonate with excess TFA.

Preparation of
trans-4-aminocyclohexylmethanesulfonate (C),
method 2

A 50 L three-neck round bottom flask was equipped with a mechanical stirrer, addition funnel and thermocouple and was placed into a cooling tub. To the flask was added trans-4-(tert-butoxycarbonylamino)cyclohexylmethanesulfonate (3474 g, 1.0 eq) and DCM (5.9 L) to the flask. The resulting suspension was stirred for 5 to 10 minutes at ambient temperature, and then trifluoroacetic acid (TFA, 5.9 L) was added via addition funnel slowly over 2.5 hours to control the resulting exotherm and rate of gas evolution. The reaction mixture was stirred at room temperature overnight and then cooled to 15° C. to 20° C. using an ice water bath. 2-Methyl tetrahydrofuran (2-MeTHF, 11.8 L) was then added via the addition funnel at a rate to maintain the internal temperature below 25° C. (approximately 1.5 hours). The addition of the first 4-5 L of 2-MeTHF was exothermic. The resulting suspension was stirred for 1 hour. The solids were collected by filtration and then washed with 2-MeTHF (2×2.2 L) and then dried under vacuum at ambient temperature to a constant weight to provide the captioned compound as a white solid.

Preparation of 7-azabicyclo[2.2.1]heptane
hydrochloride (8-HCl), method 1

The TFA salt of trans-4-aminocyclohexylmethanesulfonate (200 g, 650.9 mmol) was introduced into a 3-necked flask followed by the addition of water (2.200 L, 11 vol). NaOH (78.11 g, 1.953 mol, 3 eq) was slowly added, keeping the temperature of the reaction mixture below 25° C. and the mixture was stirred overnight. DCM (1.4 L, 7 vol) was then added and the mixture stirred, and the organic layer was separated. The aqueous layer was then extracted a second time with DCM (1.4 L, 7 vol), and the DCM layers were combined. HCl (108.5 mL, 12M, 1.3020 mol, 2 eq) was then added, the mixture was stirred for 30 min and then concentrated on a rotary evaporator to dryness. Acetonitrile (10 vol) was added and the mixture concentrated. This was repeated 3 times until all trace water was azeotropically removed, to provide 7-azabicyclo[2.2.1]heptane hydrochloride. The crude product was recrystallized from acetonitrile (10 vol) to provide 7-azabicyclo[2.2.1]heptane hydrochloride 8-HCl as a colorless crystalline solid. $^1$HNMR (DMSO-d$^6$) ppm 8.02-8.04 (d); 7.23-7.31 (m); 4.59 (s); 3.31 (s); 2.51-3.3 (m); 1.63-1.75 (m); 1.45-1.62 (m).

As a note, instead of adding DCM for extraction, the crude product can also be distilled at about 95° C. to 97° C. and further recrystallized.

Preparation of 7-azabicyclo[2.2.1]heptane
hydrochloride (8-HCl), method 2

A 50 L three neck round bottom flask equipped with a mechanical stirrer, addition funnel and thermocouple and was placed into a heating mantle. Trans-4-aminocyclohexylmethanesulfonate trifluoroacetate in (3000 g, 1 eq) and water (30 L) were added to the flask. The mixture was stirred, as 50% NaOH (2343 g, 29.29 mol, 3 eq) was added by an addition funnel at such a rate as to maintain the temperature below 25° C. because the addition was mildly exothermic. Upon completion of the NaOH addition, the reaction mixture was stirred overnight at room temperature. The product was recovered by fractional distillation at reflux temperature, (approximately 100° C.) with a head temperature of 95° C. to 98° C. The pH of each fraction was adjusted to 2 by adding HCl, and concentrated under reduced pressure at 55° C. to leave a thick paste. Acetonitrile (ACN 1.5 L) was added and the resulting suspension was stirred for 30 minutes and then cooled to 0° C. to 5° C. for 1 hour. The solids were collected by filtration, washed with cold (0 to 5° C.) ACN (2×600 mL), and dried under vacuum at 50° C. to a constant weight.

A 22 L three-neck round bottom flask was equipped with a mechanical stirrer, thermocouple, and condenser and placed into a heating mantle. The collected solids (2382 g), methanol (4.7 L) and 2-MeTHF (4.7 L) were added to the flask. The resulting suspension was stirred and heated to reflux (approximately 65° C.). The reaction flask was transferred to a cooling tub, and the mixture was stirred. 2-MeTHF (4.7 L) was then added via addition funnel over 30 minutes. The resulting suspension was cooled to 0 to 5° C. and stirred at this temperature for 30 minutes. The solids were collected by filtration, washed with cold (0 to 5° C.) 2-MeTHF (2×600 mL), and then dried under vacuum at 55° C. to a constant weight.

A 12 L three-neck round bottom flask equipped with a mechanical stirrer, thermocouple, nitrogen inlet and condenser was placed into a heating mantle. The crude product (2079 g) and ACN (6.2 L) were added to the flask. The resulting suspension was stirred and heated to reflux (approximately 82° C.) for 30 minutes. The flask was transferred to a cooling tub and the suspension was slowly cooled to 0 to 5° C. and maintained at this temperature for 1 hour. The solids were collected by filtration, washed with cold (0 to 5° C.) ACN (3×600 mL), and dried under vacuum at 55° C. to a constant weight affording to provide the captioned product.

Example 1A

Preparation of 4-oxo-5-(trifluoromethyl)-1,4-dihydroquinoline-3-carboxylic acid (2)

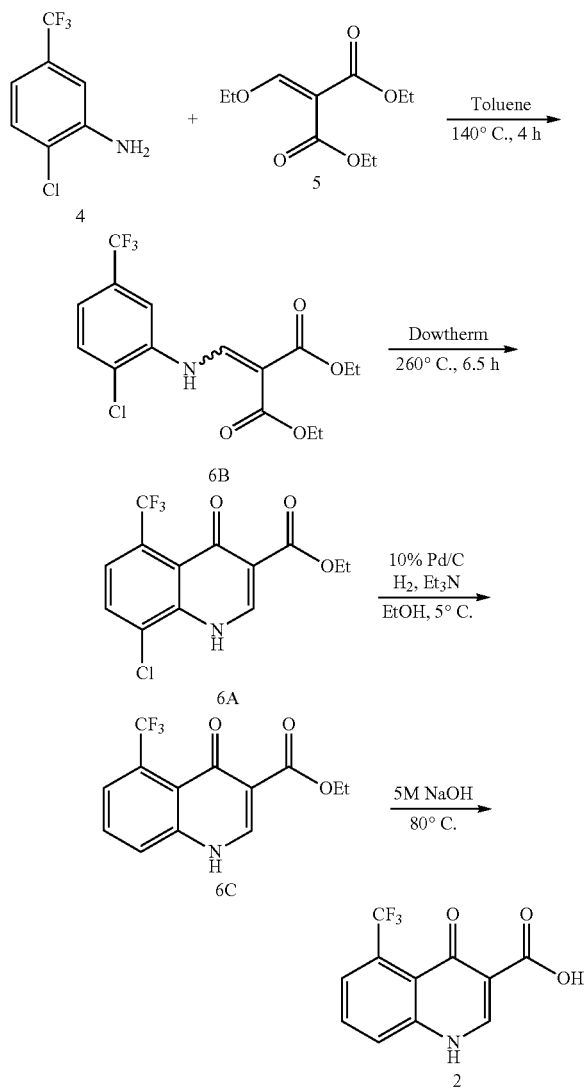

Preparation of diethyl 2-((2-chloro-5-(trifluoromethyl)phenylamino)methylene)malonate (6B)

2-Chloro-5-(trifluoromethyl)aniline 4 (200 g, 1.023 mol), diethyl 2-(ethoxymethylene)malonate (5) (276 g, 1.3 mol) and toluene (100 mL) were combined under a nitrogen atmosphere in a 3-neck, 1-L round bottom flask equipped with Dean-Stark condenser. The solution was heated with stirring to 140° C. and the temperature was maintained for 4 h. The reaction mixture was cooled to 70° C. and hexane (600 mL) was slowly added. The resulting slurry was stirred and allowed to cool to room temperature. The solid was collected by filtration, washed with 10% ethyl acetate in hexane (2×400 mL) and then dried under vacuum to provide a white solid (350 g, 94% yield) as the desired condensation product diethyl 2-((2-chloro-5-(trifluoromethyl)phenylamino)methylene)malonate (6B). $^1$H NMR (400 MHz, DMSO-$d_6$) δ 11.28 (d, J=13.0 Hz, 1H), 8.63 (d, J=13.0 Hz, 1H), 8.10 (s, 1H), 7.80 (d, J=8.3 Hz, 1H), 7.50 (dd, J=1.5, 8.4 Hz, 1H), 4.24 (q, J=7.1 Hz, 2H), 4.17 (q, J=7.1 Hz, 2H), 1.27 (m, 6H).

Preparation of ethyl 8-chloro-4-oxo-5-(trifluoromethyl)-1,4-dihydroquinoline-3-carboxylate (6A)
Method 1

A 3-neck, 1 L flask was charged with Dowtherm® (200 mL, 8 mL/g), which was degassed at 200° C. for 1 h. The solvent was heated to 260° C. and charged in portions over 10 min with diethyl 2-((2-chloro-5-(trifluoromethyl)phenylamino)methylene)malonate (6B) (25 g, 0.07 mol). The resulting mixture was stirred at 260° C. for 6.5 hours (h) and the resulting ethanol byproduct removed by distillation. The mixture was allowed to slowly cool to 80° C. Hexane (150 mL) was slowly added over 30 minutes (min), followed by an additional 200 mL of hexane added in one portion. The slurry was stirred until it had reached room temperature. The solid was filtered, washed with hexane (3×150 mL), and then dried under vacuum to provide ethyl 8-chloro-4-oxo-5-(trifluoromethyl)-1,4-dihydroquinoline-3-carboxylate (6A) as a tan solid. $^1$H NMR (400 MHz, DMSO-$d_6$) δ 11.91 (s, 1H), 8.39 (s, 1H), 8.06 (d, J=8.3 Hz, 1H), 7.81 (d, J=8.4 Hz, 1H), 4.24 (q, J=7.1 Hz, 2H), 1.29 (t, J=7.1 Hz, 3H).

Preparation of ethyl 8-chloro-4-oxo-5-(trifluoromethyl)-1,4-dihydroquinoline-3-carboxylate (6A)
Method 2

Compound 6B (2000 g, 5.468 mol) was introduced into the reactor. Dowtherm (4.000 L) was charged to the reactor and degassed at room temperature overnight with nitrogen purge. It was then stirred and warmed to 260° C. EtOH produced was distilled off. The reaction was monitored and was complete after 5.5 h, the reaction was substantially complete. Heat source was removed and the reaction mixture was cooled to 80° C. and heptane (2.000 L) was charged. The mixture was stirred for 30 min. Heptane (6.000 L) was charged to the stirred mixture and stirring continued overnight. Solids were filtered off and washed with heptane (4.000 L) and dried in a vacuum oven at 50° C. to provide Compound 6A.

Preparation of ethyl 4-oxo-5-(trifluoromethyl)-1H-quinoline-3-carboxylate (6C)

A 3-neck, 5 L flask was charged with of ethyl 8-chloro-4-oxo-5-(trifluoromethyl)-1,4-dihydroquinoline-3-carboxylate (6A) (100 g, 0.3 mol), ethanol (1250 mL, 12.5 mL/g) and triethylamine (220 mL, 1.6 mol). The vessel was then charged with 10 g of 10% Pd/C (50% wet) at 5° C. The reaction was stirred vigorously under hydrogen atmosphere for 20 h at 5° C., after which time the reaction mixture was concentrated to a volume of approximately 150 mL. The product, ethyl 4-oxo-5-(trifluoromethyl)-1H-quinoline-3-carboxylate (6C), as a slurry with Pd/C, was taken directly into the next step.

Preparation of 4-oxo-5-(trifluoromethyl)-1,4-dihydroquinoline-3-carboxylic acid (2)

Ethyl 4-oxo-5-(trifluoromethyl)-1H-quinoline-3-carboxylate (6C) (58 g, 0.2 mol, crude reaction slurry containing Pd/C) was suspended in NaOH (814 mL of 5 M, 4.1 mol) in a 1 L flask with a reflux condenser and heated at 80° C. for 18 h, followed by further heating at 100° C. for 5 h. The reaction was filtered warm through packed Celite to remove Pd/C and the Celite was rinsed with 1 N NaOH. The filtrate was acidified to about pH 1 to obtain a thick, white precipitate. The precipitate was filtered then rinsed with water and cold acetonitrile. The solid was then dried under vacuum to provide 4-oxo-5-(trifluoromethyl)-1,4-dihydroquinoline-3-carboxylic acid (2) as a white solid. $^1$H NMR (400.0 MHz, DMSO-$d_6$) δ 15.26 (s, 1H), 13.66 (s, 1H), 8.98 (s, 1H), 8.13 (dd, J=1.6, 7.8 Hz, 1H), 8.06-7.99 (m, 2H).

Example 1B

Alternative Preparation of 4-oxo-5-(trifluoromethyl)-1,4-dihydroquinoline-3-carboxylic acid (2)

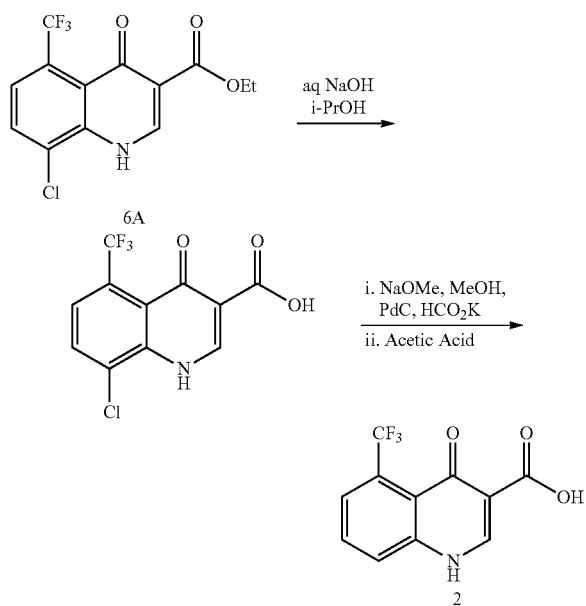

Preparation of 8-chloro-4-oxo-5-(trifluoromethyl)-1,4-dihydroquinoline-3-carboxylic acid (6D)

Ethyl 8-chloro-4-oxo-5-(trifluoromethyl)-1,4-dihydroquinoline-3-carboxylate (6B) (1200 g, 3.754 mol) was charged into a vessel followed by the addition of 2-propanol (1.200 L) and water (7.200 L) and stirred. NaOH (600.6 g, 7.508 mol) and water (1.200 L) were mixed and allowed to cool to room temperature. The resulting NaOH solution was charged into the reaction vessel. The reaction mixture was heated to 80° C. and stirred for 3.5 h generating a dark and homogenous mixture. After an additional hour, acetic acid (9.599 L [of a 20% w/v solution], 31.97 mol) was added via dropping funnel over 45 min. The reaction mixture was cooled to 22° C. at a rate of 6° C./h with stirring. The resulting solid was filtered, washed with water (3 L) to generate a wet cake of (1436 g). The filtrate was dried in a vacuum oven with nitrogen bleed over Drierite® to generate 8-chloro-4-oxo-5-(trifluoromethyl)-1,4-dihydroquinoline-3-carboxylic acid as a brown solid. The 8-chloro-4-oxo-5-(trifluoromethyl)-1,4-dihydroquinoline-3-carboxylic acid was purified by slurrying in 1.5 L methanol, with stirring, for 6 h. It was then filtered and dried to furnish 968.8 g of purified 8-chloro-4-oxo-5-(trifluoromethyl)-1,4-dihydroquinoline-3-carboxylic acid (6D).

Preparation of 4-oxo-5-(trifluoromethyl)-1,4-dihydroquinoline-3-carboxylic acid (2)

8-chloro-4-oxo-5-(trifluoromethyl)-1,4-dihydroquinoline-3-carboxylic acid (6D) (18.5 g, 1.00 eq, limiting reagent) was charged into a reaction vessel and MeOH (118 mL, 6.4 vol) was added under inert atmosphere with agitation. NaOMe (3.53 g, 1.00 eq.) was added portion wise over 10 min to the reactor. The mixture was stirred until all solids were in solution (5-10 minutes). Palladium on carbon (2.7 g, 0.03 eq) was then added to the reaction mixture. Potassium formate (10.78 g, 2 eq.) dissolved in MeOH (67 mL, 3.6 vol) was added to the reaction mixture over 30 min. It was then stirred for about 4.5 h at ambient temperature. The reaction was judged complete when 8-chloro-4-oxo-5-(trifluoromethyl)-1,4-dihydroquinoline-3-carboxylic acid is no more than 1.0% with respect to 4-oxo-5-(trifluoromethyl)-1,4-dihydroquinoline-3-carboxylic acid. When the reaction was complete, the mixture was filtered through a pad of Celite (37 g [~approximately twice the mass of the starting material, 6D]) to remove solids. The Celite cake was washed with MeOH (37 mL, 2 vol). The filtrate was charged into a clean reaction vessel and stirred. Acetic acid (7.22 mL, 2 eq.) was charged continuously to the stirred solution over at least 45 minutes and the resulting slurry stirred for between 5-16 h. The solid was filtered and the cake washed with MeOH (56 mL, 3 vol), suction-dried and then vacuum dried to provide the captioned carboxylic acid 2.

Alternatively, the potassium formate reagent may be replaced with hydrogen gas.

Example 2A

Preparation of 4-(7-azabicyclo[2.2.1]heptan-7-yl)-2-(trifluoromethyl)aniline (3)

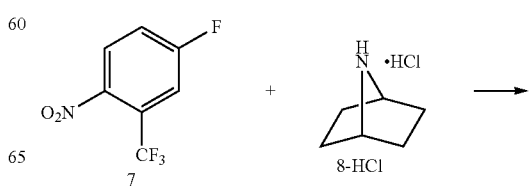

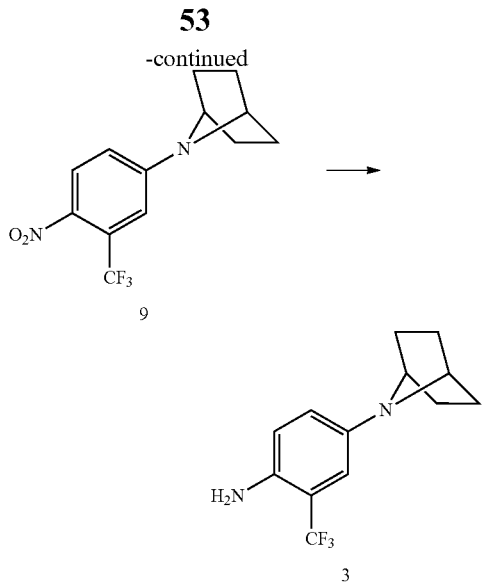

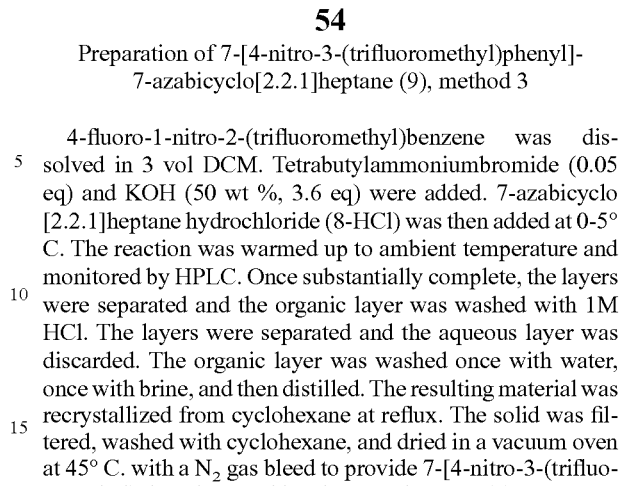

Preparation of 7-[4-nitro-3-(trifluoromethyl)phenyl]-7-azabicyclo[2.2.1]heptane (9), method 1

To a flask containing 7-azabicyclo[2.2.1]heptane hydrochloride (8-HCl) (4.6 g, 34.43 mmol, obtained from under a nitrogen atmosphere was added a solution of 4-fluoro-1-nitro-2-(trifluoromethyl)benzene (7) (6.0 g, 28.69 mmol) and triethylamine (8.7 g, 12.00 ml, 86.07 mmol) in acetonitrile (50 ml). The reaction flask was heated at 80° C. under a nitrogen atmosphere for 16 h. The reaction mixture was allowed to cool and then was partitioned between water and dichloromethane. The organic layer was washed with 1 M HCl, dried over Na$_2$SO$_4$, filtered, and concentrated to dryness. Purification by silica gel chromatography (0-10% ethyl acetate in hexanes) yielded 7-[4-nitro-3-(trifluoromethyl) phenyl]-7-azabicyclo[2.2.1]heptane (9) as a yellow solid. $^1$H NMR (400.0 MHz, DMSO-d$_6$) δ 8.03 (d, J=9.1 Hz, 1H), 7.31 (d, J=2.4 Hz, 1H), 7.25 (dd, J=2.6, 9.1 Hz, 1H), 4.59 (s, 2H), 1.69-1.67 (m, 4H), 1.50 (d, J=7.0 Hz, 4H).

Preparation of 7-[4-nitro-3-(trifluoromethyl)phenyl]-7-azabicyclo[2.2.1]heptane (9), method 2

4-fluoro-1-nitro-2-(trifluoromethyl)benzene (7) (901 g, 4.309 mol) was introduced into a 30 L jacketed vessel along with Na$_2$CO$_3$ (959.1 g, 9.049 mol) and DMSO (5 L, 5.5 vol) under nitrogen atmosphere and stirring. 7-azabicyclo[2.2.1] heptane hydrochloride (8-HCl) (633.4 g, 4.740 mol) was then added to the vessel in portions. The temperature was gradually raised to 55° C. When the reaction was substantially complete, the mixture was diluted with 10 vol EtOAc and washed with water (5.5 vol) three times or until DMSO in the aqueous layer disappeared (HPLC). The organic layer was concentrated to 4 vol and then the solvent was swapped with cyclohexane until all the EtOAc was removed, and the total volume in the flask was about 4 vol containing cyclohexane. The reaction mixture was heated to 60° C. on a rotary evaporator for 30 min. Then the solution was cooled to room temperature with stirring or rotation for 3 h. When all the solid crystallized, the solution was concentrated to dryness to provide 7-[4-nitro-3-(trifluoromethyl)phenyl]-7-azabicyclo [2.2.1]heptane (9).

Preparation of 7-[4-nitro-3-(trifluoromethyl)phenyl]-7-azabicyclo[2.2.1]heptane (9), method 3

4-fluoro-1-nitro-2-(trifluoromethyl)benzene was dissolved in 3 vol DCM. Tetrabutylammoniumbromide (0.05 eq) and KOH (50 wt %, 3.6 eq) were added. 7-azabicyclo [2.2.1]heptane hydrochloride (8-HCl) was then added at 0-5° C. The reaction was warmed up to ambient temperature and monitored by HPLC. Once substantially complete, the layers were separated and the organic layer was washed with 1M HCl. The layers were separated and the aqueous layer was discarded. The organic layer was washed once with water, once with brine, and then distilled. The resulting material was recrystallized from cyclohexane at reflux. The solid was filtered, washed with cyclohexane, and dried in a vacuum oven at 45° C. with a N$_2$ gas bleed to provide 7-[4-nitro-3-(trifluoromethyl)phenyl]-7-azabicyclo[2.2.1]heptane (9).

Preparation of 4-(7-azabicyclo[2.2.1]heptan-7-yl)-2-(trifluoromethyl)aniline (3)

A flask charged with 7-[4-nitro-3-(trifluoromethyl)phenyl]-7-azabicyclo[2.2.1]heptane (26) (7.07 g, 24.70 mmol) and 10% Pd/C (0.71 g, 6.64 mmol) was evacuated and then flushed with nitrogen. Ethanol (22 ml) was added and the reaction flask was fitted with a hydrogen balloon. After stirring vigorously for 12 h, the reaction mixture was purged with nitrogen and Pd/C was removed by filtration. The filtrate was concentrated to a dark oil under reduced pressure and the residue purified by silica gel chromatography (0-15% ethyl acetate in hexanes) to provide 447-azabicyclo[2.2.1]heptan-7-yl)-2-(trifluoromethyl)aniline (3) as a purple solid (5.76 g, 91% yield). $^1$H NMR (400.0 MHz, DMSO-d$_6$) δ 6.95 (dd, J=2.3, 8.8 Hz, 1H), 6.79 (d, J=2.6 Hz, 1H), 6.72 (d, J=8.8 Hz, 1H), 4.89 (s, 2H), 4.09 (s, 2H), 1.61-1.59 (m, 4H) and 1.35 (d, J=6.8 Hz, 4H).

Example 2B

Preparation of the hydrochloride salt of 4-(7-azabicyclo[2.2.1]heptan-7-yl)-2-(trifluoromethyl)aniline (3-HCl)

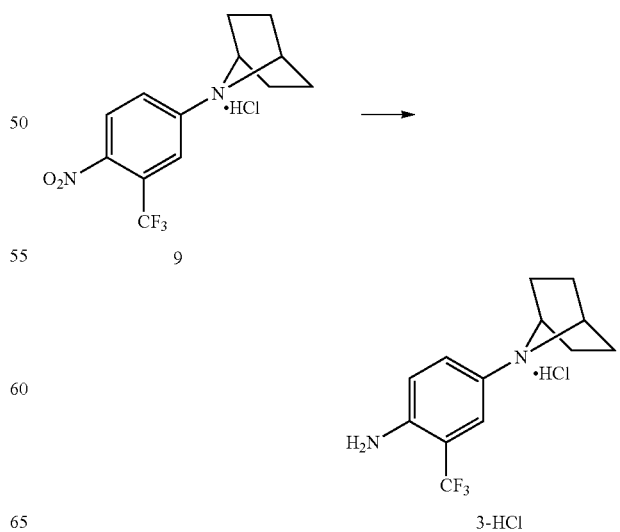

Preparation of the hydrochloride salt of 4-(7-azabicyclo[2.2.1]heptan-7-yl)-2-(trifluoromethyl)aniline (3-HCl), method 1. Palladium on carbon (150 g, 5% w/w) was charged into a Büchi Hydrogenator (20 L capacity) under a nitrogen atmosphere followed by the addition of the hydrochloride salt of 7-[4-nitro-3-(trifluoromethyl)phenyl]-7-azabicyclo[2.2.1]heptane (9) (1500 g) and 2-methyltetrahydrofuran (10.5 L, 7 vol). Hydrogen gas was charged into the closed vessel to a pressure of +0.5 bar above atmospheric pressure. A vacuum was applied for about 2 min followed by the introduction of hydrogen gas to a pressure of 0.5 bar. This process was repeated 2 times. Then hydrogen gas was continuously charged at +0.5 bar above atmospheric pressure. The mixture was stirred and the temperature was maintained between 18° C. and 23° C. by cooling the jacket of the vessel. Once the reaction consumed no more hydrogen and evolved no more heat, a vacuum was again applied. Nitrogen gas was charged into the vessel at 0.5 bar and a vacuum was reapplied followed by a second charge of 0.5 bar nitrogen gas. When the reaction was substantially complete, the reaction mixture was transferred into a receiving flask under nitrogen atmosphere via a filter funnel using a Celite filter. The Celite filter cake was washed with 2-methyltetrahydrofuran (3 L, 2 vol). The washings and filtrate were charged into a vessel equipped with stirring, temperature control, and a nitrogen atmosphere. 4M HCl in 1,4-dioxane (1 vol) was added continuously over 1 h into the vessel at 20° C. The mixture was stirred for an additional 10 h (or overnight), filtered, and washed with 2-methyltetrahydrofuran (2 vol) and dried to generate 1519 g of the of 4-(7-azabicyclo[2.2.1]heptan-7-yl)-2-(trifluoromethyl)aniline hydrochloride (3-HCl) as a white crystalline solid.

Alternative solvents may also be substituted in this example. For instance, MeOH and/or EtOH could be used in place of 2-MeTHF.

Example 3A

Preparation of N-(4-(7-azabicyclo[2.2.1]heptan-7-yl)-2-(trifluoromethyl)phenyl)-4-oxo-5-(trifluoromethyl)-1,4-dihydroquinoline-3-carboxamide as Form A (Compound 1 Form A)

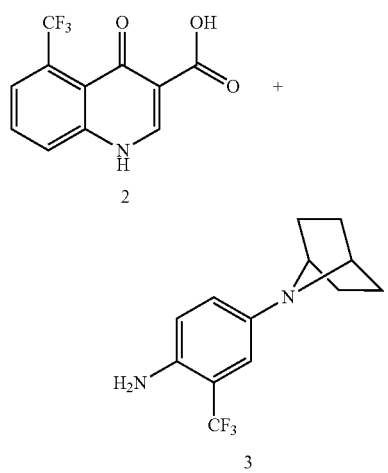

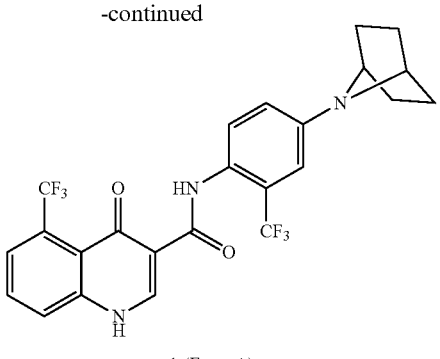

1 (Form A)

To a solution of 4-oxo-5-(trifluoromethyl)-1H-quinoline-3-carboxylic acid (2) (9.1 g, 35.39 mmol) and 4-(7-azabicyclo[2.2.1]heptan-7-yl)-2-(trifluoromethyl)aniline (3) (9.2 g, 35.74 mmol) in 2-methyltetrahydrofuran (91.00 mL) was added propyl phosphoric acid cyclic anhydride (50% solution in ethyl acetate, 52.68 mL, 88.48 mmol) and pyridine (5.6 g, 5.73 mL, 70.78 mmol) at room temperature. The reaction flask heated at 65° C. for 10 h under a nitrogen atmosphere. After cooling to room temperature the reaction was then diluted with ethyl acetate and quenched with saturated $Na_2CO_3$ solution (50 mL). The layers were separated, and the aqueous layer was extracted twice more with ethyl acetate. The combined organic layers were washed with water, dried over $Na_2SO_4$, filtered and concentrated to a tan solid. The crude solid product was slurried in ethyl acetate/diethyl ether (2:1), collected by vacuum filtration, and washed twice more with ethyl acetate/diethyl ether (2:1) to provide the crude product as a light yellow crystalline powder. The powder was dissolved in warm ethyl acetate and absorbed onto Celite. Purification by silica gel chromatography (0-50% ethyl acetate in dichloromethane) provided Form A of N-(4-(7-azabicyclo[2.2.1]heptan-7-yl)-2-(trifluoromethyl)phenyl)-4-oxo-5-(trifluoromethyl)-1,4-dihydroquinoline-3-carboxamide (Compound 1 Form A) as a white crystalline solid. LC/MS m/z 496.0 $[M+H]^+$, retention time 1.48 min (RP-$C_{18}$, 10-99% $CH_3CN$/0.05% TFA over 3 min). $^1H$ NMR (400.0 MHz, DMSO-$d_6$) δ 13.08 (s, 1H), 12.16 (s, 1H), 8.88 (s, 1H), 8.04 (dd, J=2.1, 7.4 Hz, 1H), 7.95-7.88 (m, 3H), 7.22 (dd, 2.5, 8.9 Hz, 1H), 7.16 (d, J=2.5 Hz, 1H), 4.33 (s, 2H), 1.67 (d, J=6.9 Hz, 4H), 1.44 (d, J=6.9 Hz, 4H).

The powder diffractogram of Compound 1 Form A is shown in FIG. 1.

Table 1 provides a list of XRPD peaks representative of Compound 1 Form A.

TABLE 1

Representative XRPD peaks of Compound 1 Form A.

| 2-Theta (degrees) | Relative Intensity (%) |
|---|---|
| 7.9 | 100.0 |
| 9.3 | 10.8 |
| 11.9 | 12.8 |
| 14.4 | 35.2 |
| 15.1 | 12.6 |
| 15.8 | 34.1 |
| 17.0 | 25.2 |
| 17.7 | 13.8 |
| 19.3 | 39.4 |
| 20.1 | 20.2 |
| 21.4 | 14.5 |
| 21.8 | 94.2 |

TABLE 1-continued

Representative XRPD peaks of Compound 1 Form A.

| 2-Theta (degrees) | Relative Intensity (%) |
|---|---|
| 23.4 | 30.0 |
| 23.8 | 92.0 |
| 25.6 | 8.9 |
| 26.8 | 6.4 |
| 29.4 | 8.1 |
| 29.7 | 18.1 |
| 30.1 | 14.2 |
| 31.2 | 9.9 |

Figure 2:
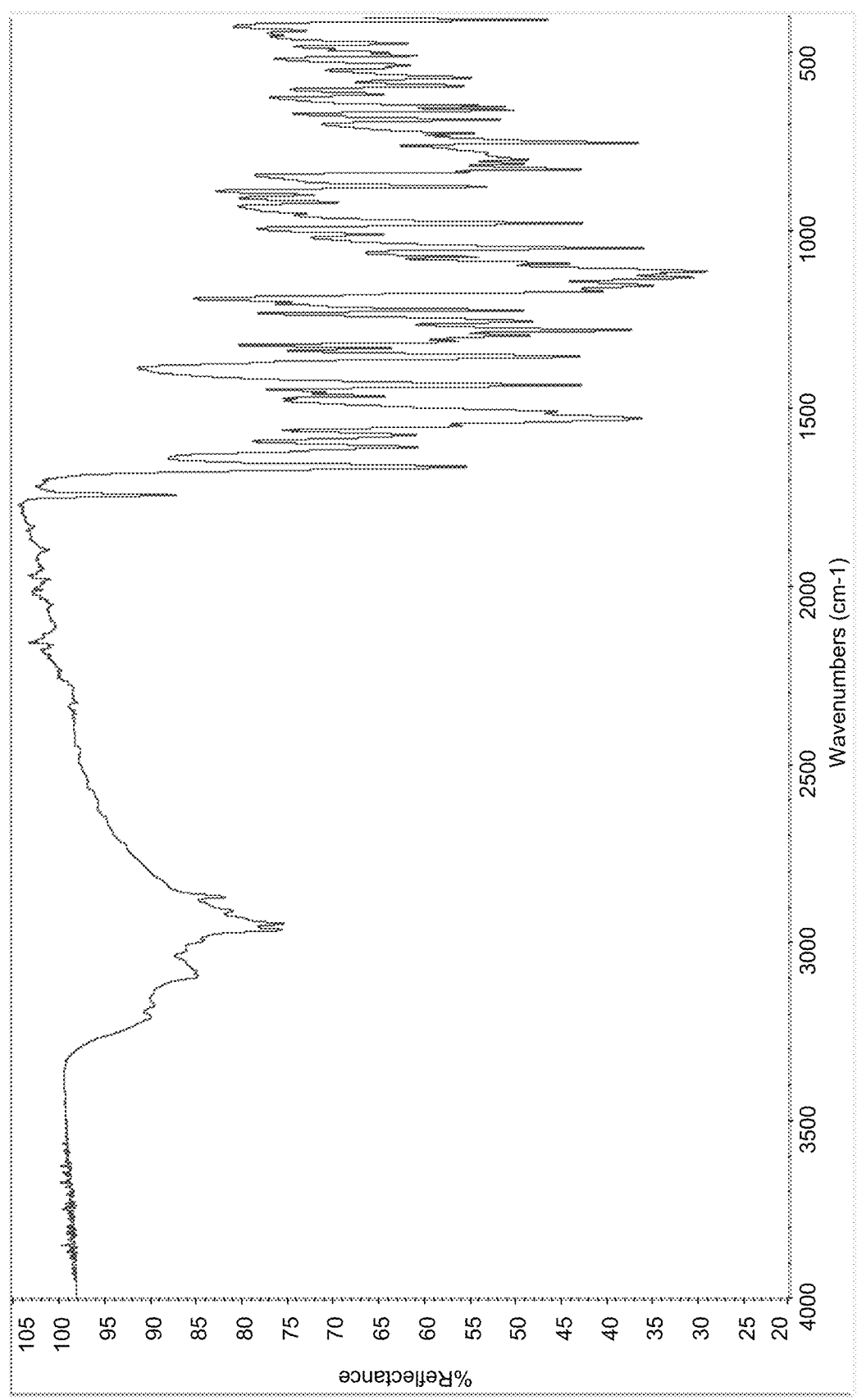
FIG. 2 is an FTIR spectrum of a representative sample of Compound 1 Form A.

A representative sample of Compound 1 Form A gave the FTIR spectrum provided in FIG. 2.

Figure 3:
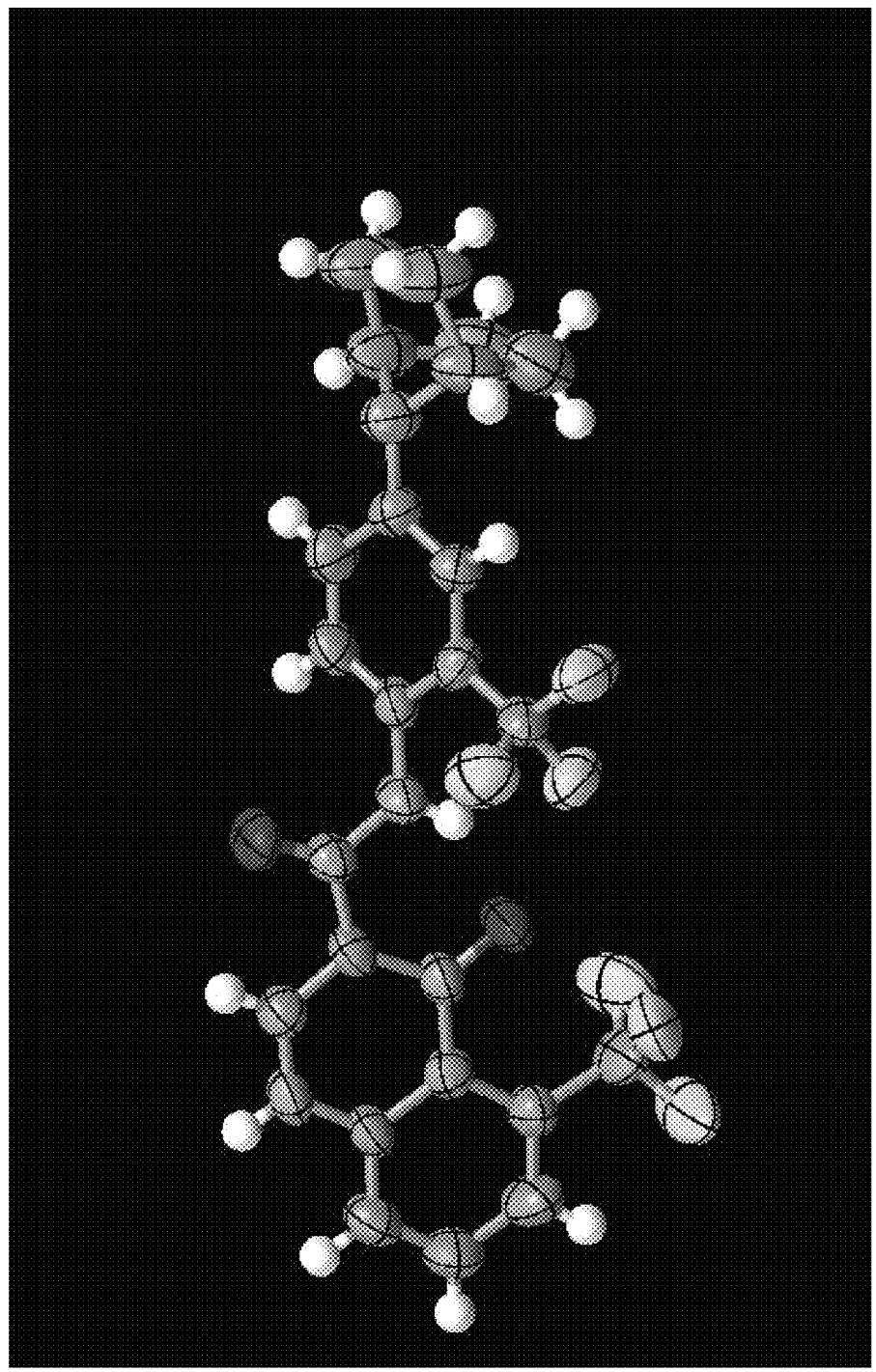
FIG. 3 is an illustration of the conformational structure of Compound 1 Form A based on single X-ray analysis.

Conformational pictures of Compound 1 Form A based on single X-ray analysis are shown in FIG. 3. Diffraction data were acquired on a Bruker Apex II Diffractometer equipped with sealed tube CuK-alpha source and an Apex II CCD detector. The structure was solved and refined using SHELX program (Sheldrick, G. M., Acta Cryst. A64, pp. 112-122 (2008)). Based on intensities, statistics and symmetry, the structure was solved and refined in a trigonal crystal system and an R-3 space group. Compound 1 Form A has the following unit cell dimensions: a=19.1670(4) Å, b=19.1670(4) Å, c=33.6572(12) Å, α=90°, β=90°, and γ=120°.

Example 3B

Preparation of N-(4-(7-azabicyclo[2.2.1]heptan-7-yl)-2-(trifluoromethyl)phenyl)-4-oxo-5-(trifluoromethyl)-1,4-dihydroquinoline-3-carboxamide as Form A-HCl (Compound 1 Form A-HCl)

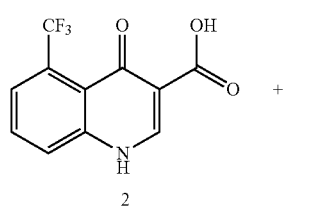

2

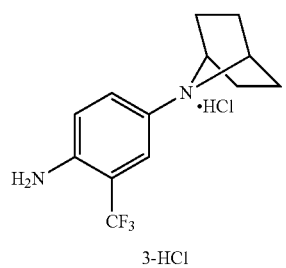

3-HCl

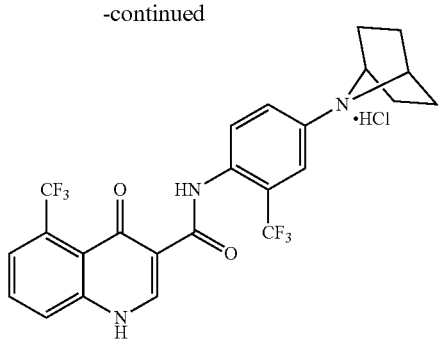

1 (Form A-HCl)

2-methyltetrahydrofuran (0.57 L, 1.0 vol) was charged into a 30 L jacketed reactor vessel, followed by the addition of the hydrochloride salt of 4-(7-azabicyclo[2.2.1]heptan-7-yl)-2-(trifluoromethyl)aniline (3-HCl) (791 g, 2.674 mol) and 4-oxo-5-(trifluoromethyl)-1,4-dihydroquinoline-3-carboxylic acid (2) (573 g, 2.2278 mol) and an additional 5.2 L (9.0 vol) of 2-methyltetrahydrofuran. Stirring commenced and T3P in 2-methyltetrahydrofuran (2.836 kg, 4.456 mol) was added to the reaction mixture over 15 min. Then, pyridine (534.0 g, 546.0 mL, 6.684 mol) was added via an addition funnel dropwise over 30 min. The mixture was warmed to 45° C. over about 30 min and stirred for 12-15 h. HPLC analysis indicated that that 4-oxo-5-(trifluoromethyl)-1,4-dihydroquinoline-3-carboxylic acid was present in an amount less than 2%. The mixture was then cooled to room temperature. 2-methyltetrahydrofuran (4 vol, 2.292 L) was added followed by water (6.9 vol, 4 L), while the temperature was maintained below 30° C. The water layer was removed and the organic layer was carefully washed twice with NaHCO$_3$ saturated aqueous solution. The organic layer was then washed with 10% w/w citric acid (5 vol) and finally with water (7 vol). The mixture was polished filtered and transferred into another dry vessel. Seed crystals of Form A-HCl of N-(4-(7-azabicyclo[2.2.1]heptan-7-yl)-2-(trifluoromethyl)phenyl)-4-oxo-5-(trifluoromethyl)-1,4-dihydroquinoline-3-carboxamide hydrochloride (Compound 1 Form A-HCl) (3.281 g, 5.570 mmol) were added. HCl (g) (10 eq) was bubbled over 2 h and the mixture was stirred overnight. The resulting suspension was filtered, washed with 2-methyltetrahydrofuran (4 vol), suction dried and oven dried at 60° C. until constant weight to provide Compound 1 Form A-HCl.

Figure 4:
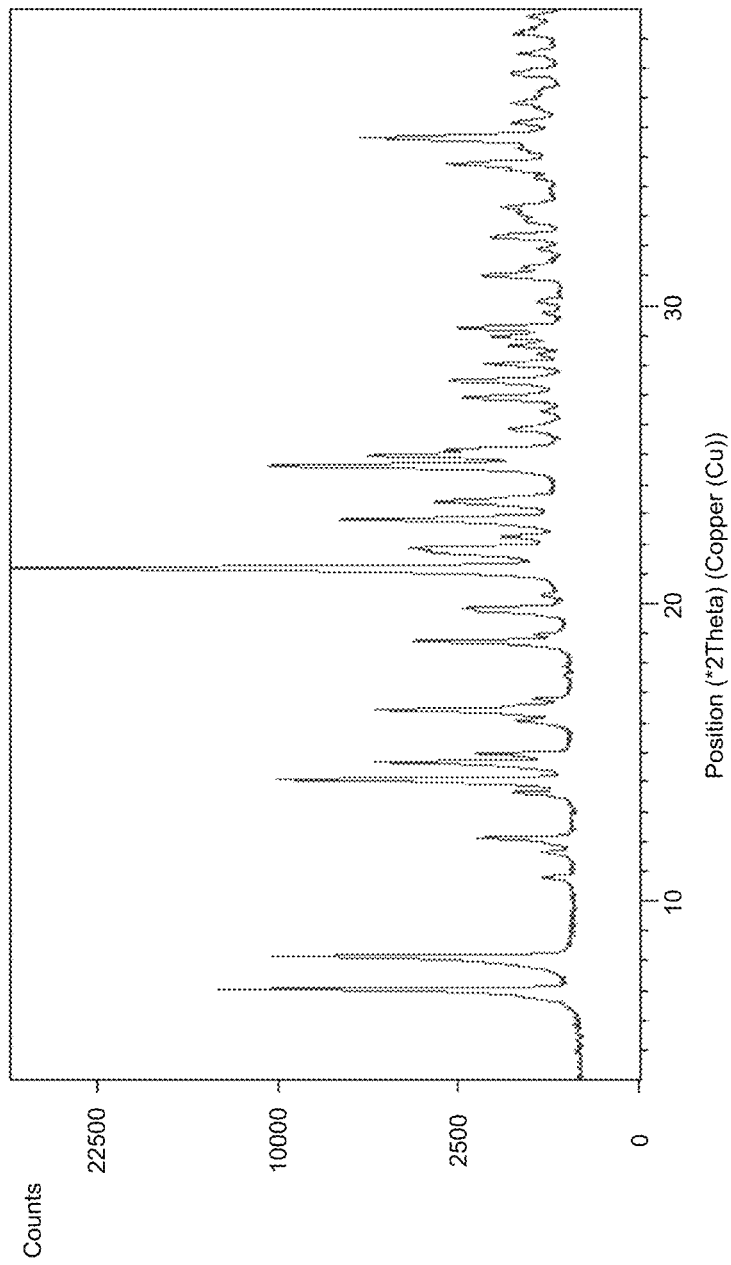
FIG. 4 is an X-ray powder diffraction pattern of an exemplary sample of Compound 1 Form A-HCl.

The powder diffractogram of Compound 1 Form A-HCl is shown in FIG. 4.

Table 2 provides representative XRPD peaks of Compound 1 Form A-HCl.

TABLE 2

Representative XRPD Peaks of Compound 1 Form A-HCl.

| 2-Theta (degrees) | Relative Intensity (%) |
|---|---|
| 7.1 | 44.3 |
| 8.2 | 33.3 |
| 10.8 | 1.5 |
| 11.7 | 1.5 |
| 12.1 | 5.8 |
| 13.7 | 3.3 |
| 14.1 | 32.1 |
| 14.7 | 16.9 |
| 15.0 | 5.7 |
| 16.1 | 3.0 |
| 16.4 | 16.9 |

TABLE 2-continued

Representative XRPD Peaks of Compound 1 Form A-HCl.

| 2-Theta (degrees) | Relative Intensity (%) |
|---|---|
| 16.6 | 3.7 |
| 16.8 | 1.9 |
| 17.6 | 0.6 |
| 18.7 | 12.4 |
| 18.9 | 1.9 |
| 19.7 | 5.4 |
| 19.8 | 6.9 |
| 20.3 | 1.5 |
| 21.2 | 100.0 |
| 21.7 | 10.6 |
| 21.9 | 12.3 |
| 22.2 | 4.0 |
| 22.8 | 21.9 |
| 23.4 | 9.8 |
| 24.6 | 34.3 |
| 25.0 | 17.9 |
| 25.2 | 8.6 |
| 25.9 | 3.6 |
| 26.5 | 1.5 |
| 26.9 | 7.0 |
| 27.5 | 8.3 |
| 28.0 | 5.3 |
| 28.3 | 1.6 |
| 28.7 | 3.5 |
| 29.0 | 4.8 |
| 29.2 | 7.5 |
| 29.8 | 1.40 |
| 30.1 | 1.8 |
| 31.0 | 5.4 |
| 31.3 | 2.6 |
| 31.9 | 1.7 |
| 32.3 | 4.6 |
| 32.4 | 3.7 |
| 32.8 | 2.3 |
| 33.3 | 3.9 |
| 34.3 | 1.8 |
| 34.5 | 3.6 |
| 34.7 | 8.7 |
| 35.3 | 3.0 |
| 35.6 | 12.7 |
| 35.6 | 18.9 |
| 36.1 | 3.2 |
| 36.8 | 3.3 |
| 37.2 | 1.7 |
| 37.8 | 3.1 |
| 38.5 | 2.8 |
| 39.1 | 3.1 |
| 39.7 | 2.3 |

A single crystal of Compound 1 Form A-HCl was determined to possess a monoclinic crystal system, a $P2_1/c$ space group, and the following unit cell dimensions: a=13.6175(4) Å, b=21.614(3) Å, c=8.3941(4) Å, α=90°, β=112.303°, and γ=90°.

A sample of Compound 1 Form A-HCl was also evaluated using microscopy.

Figure 5:
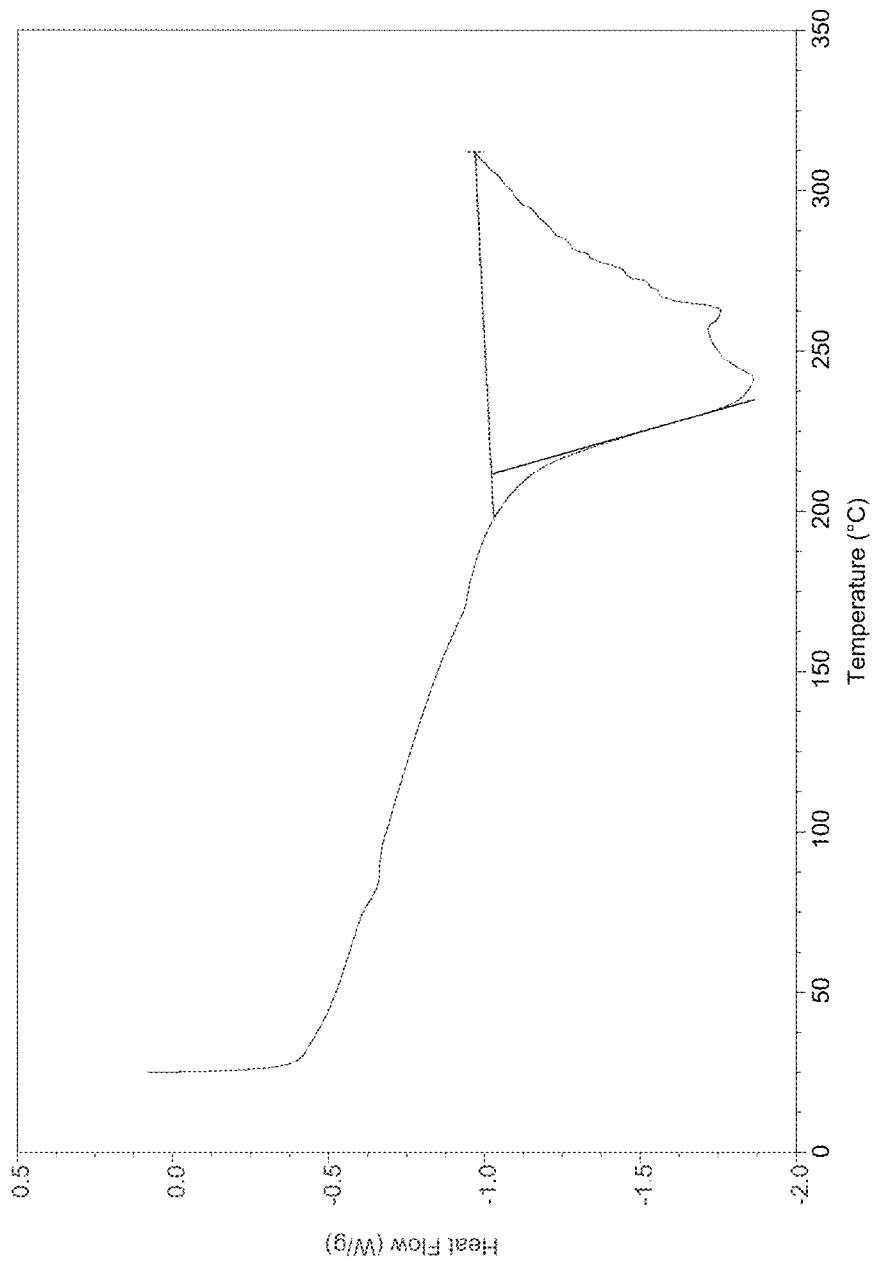
FIG. 5 is the DSC curve for a representative sample of Compound 1 Form A-HCl.
Figure 6:
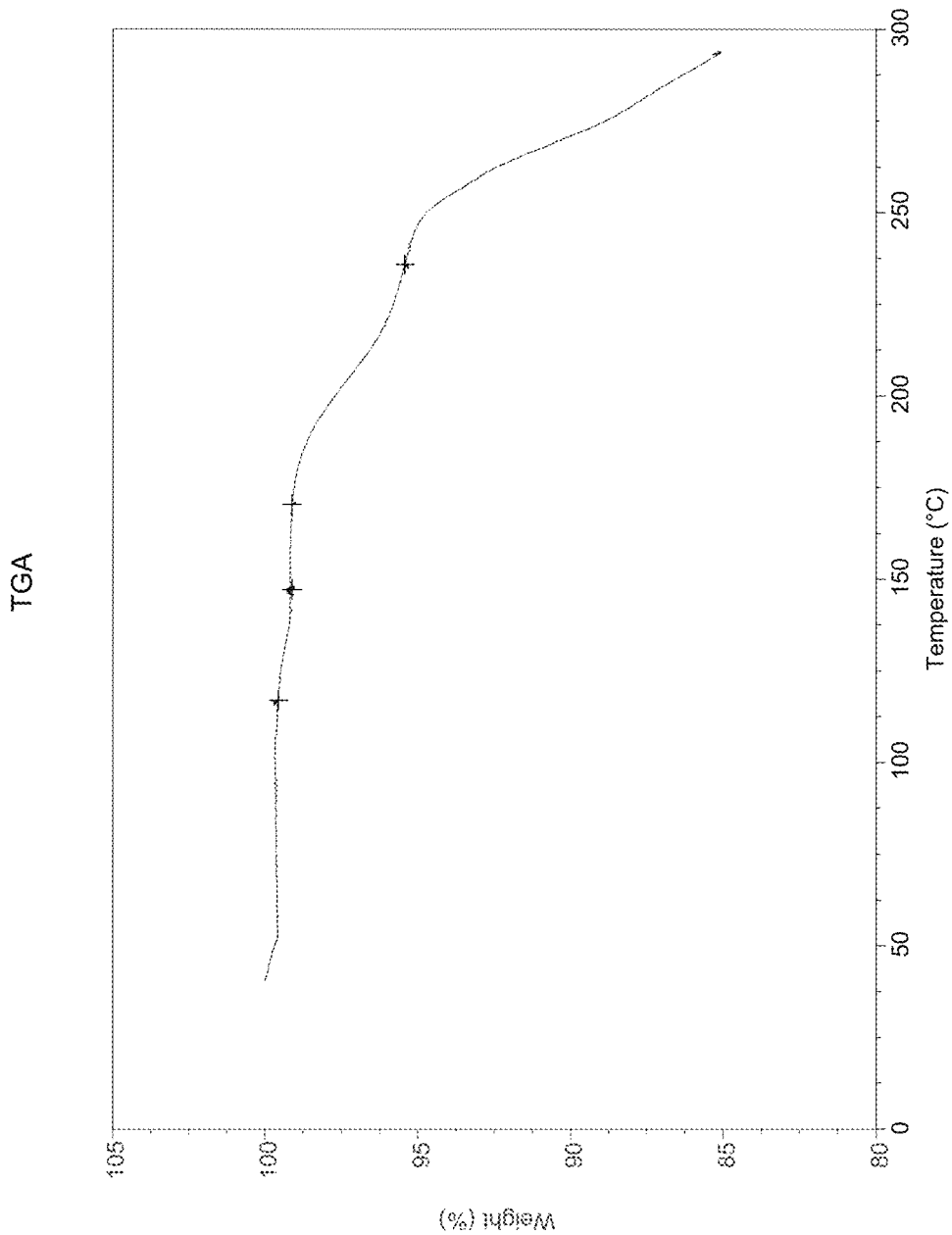
FIG. 6 is a curve generated by thermogravimetric analysis of a representative sample of Compound 1 Form A-HCl that presents sample weight as a function of temperature.

A DSC curve for a sample of Compound 1 Form A-HCl is provided at FIG. 5 and a TGA curve of a representative sample of Compound 1 Form A-HCl is provided in FIG. 6.

Figure 7:
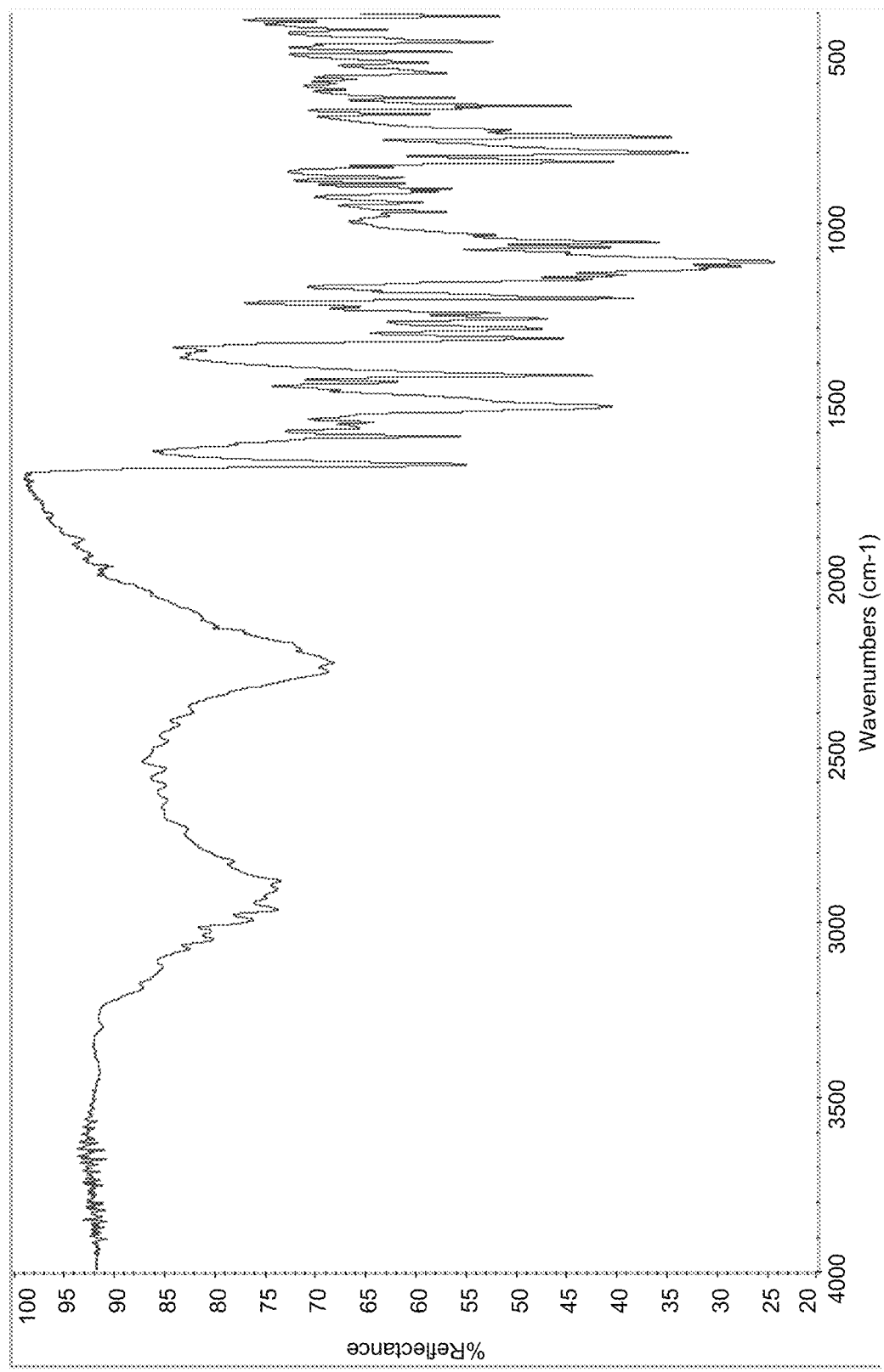
FIG. 7 is an FTIR spectrum of a representative sample of Compound 1 Form A-HCl.

A representative sample of Compound 1 Form A-HCl presented the FTIR spectrum provided in FIG. 7.

Figure 8:
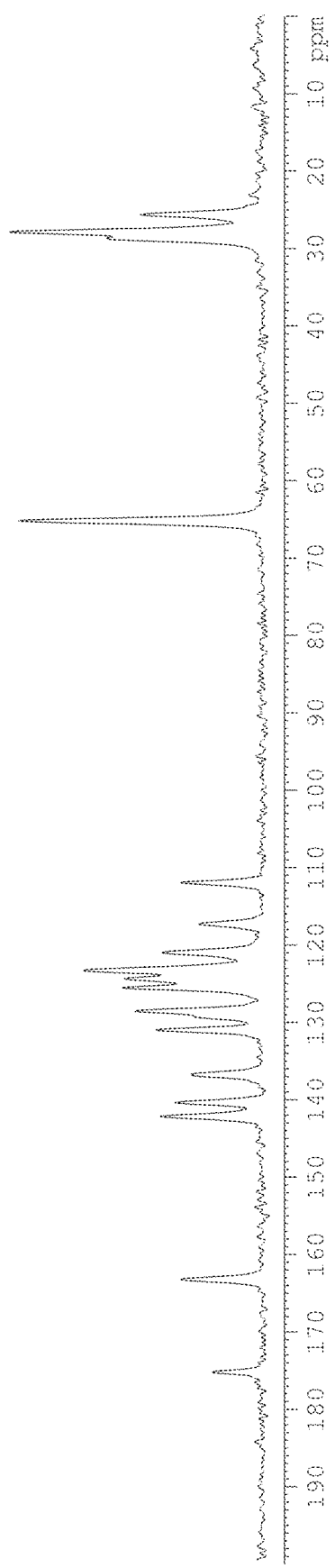
FIG. 8 is a solid phase $^{13}$C NMR spectrum of a representative sample of Compound 1 Form A-HCl.
Figure 9:
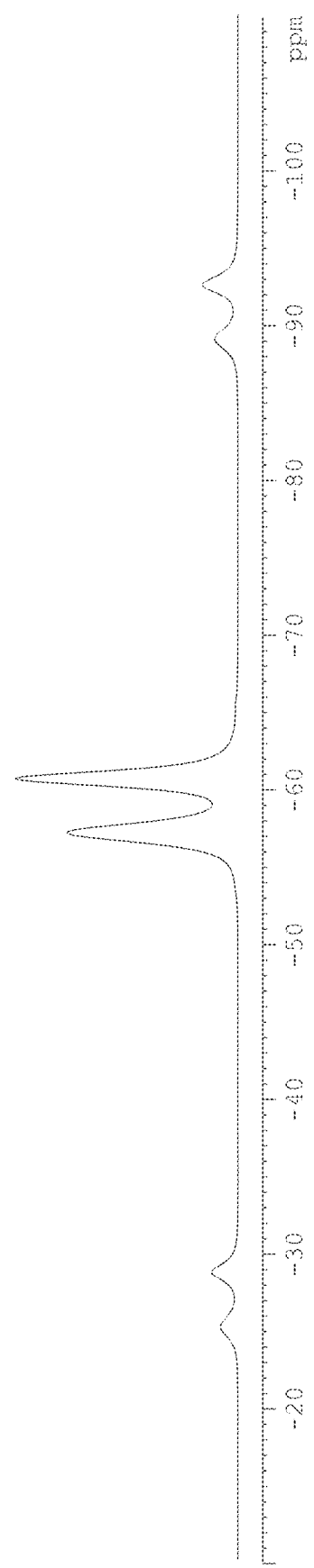
FIG. 9 is solid phase $^{19}$F NMR spectrum of a representative sample of Compound 1 Form A-HCl.

Compound 1 Form A-HCl was also analyzed using solid state $^{13}C$ and $^{19}F$ NMR. The respective NMR spectra are provided in FIGS. 8 and 9. Several peaks found in the $^{13}C$ SSNMR and $^{19}F$ SSNMR spectra are described in Tables 3 and 4.

TABLE 3

$^{13}C$ SSNMR Peaks for Compound 1 Form A-HCl.

| Peak No. | F1 (ppm) |
|---|---|
| 1 | 175.7 |
| 2 | 163.7 |
| 3 | 142.6 |
| 4 | 140.8 |
| 5 | 137.2 |
| 6 | 131.5 |
| 7 | 129.0 |
| 8 | 126.0 |
| 9 | 124.8 |
| 10 | 123.8 |
| 11 | 121.5 |
| 12 | 117.8 |
| 13 | 112.4 |
| 14 | 65.7 |
| 15 | 29.2 |
| 16 | 28.3 |
| 17 | 26.1 |

TABLE 4

$^{19}F$ SSNMR Peaks for Compound 1 Form A-HCl.

| Peak No. | F1 (ppm) |
|---|---|
| 1 | −57.0 |
| 2 | −60.5 |

Example 4A

Preparation of N-(4-(7-azabicyclo[2.2.1]heptan-7-yl)-2-(trifluoromethyl)phenyl)-4-oxo-5-(trifluoromethyl)-1,4-dihydroquinoline-3-carboxamide as Form B (Compound 1 Form

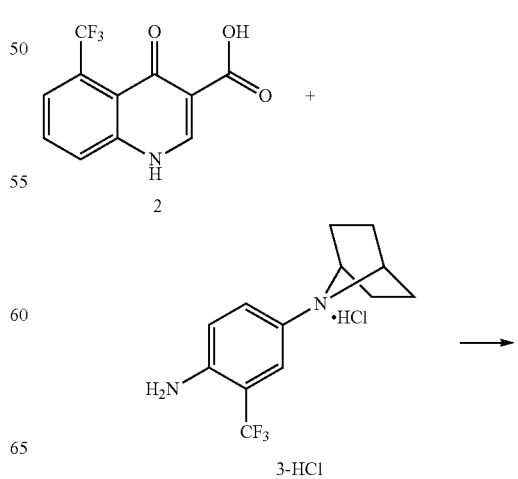

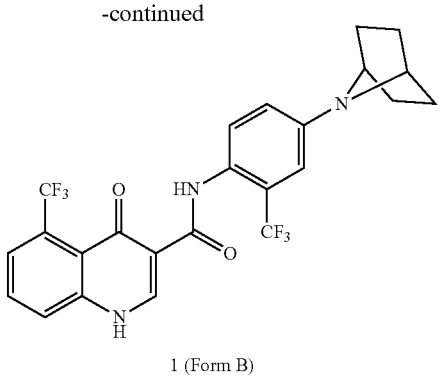

1 (Form B)

2-Methyltetrahydrofuran (1 vol) was charged into a 30 L jacketed reactor vessel followed by the addition of the hydrochloride salt of 4-(7-azabicyclo[2.2.1]heptan-7-yl)-2-(trifluoromethyl)aniline (3-HCl) (1.2 eq) and 4-oxo-5-(trifluoromethyl)-1,4-dihydroquinoline-3-carboxylic acid (2) (573 g, 2.228 mol). Additional 2-methyltetrahydrofuran (9 vol) was charged into the vessel and stirring commenced. T3P in 2-methyltetrahydrofuran (2 eq) was added to the reaction mixture over a period of 15 min. Pyridine (3 eq) was added rapidly in a dropwise fashion using an addition funnel. Under stirring, the mixture was then heated to 45° C. over a period of about 30 min and this temperature was maintained for about 5 h. The mixture was cooled to room temperature. 2-methyltetrahydrofuran (4 vol) was added followed by the slow addition of water (6.9 vol), and the temperature of the reaction was kept below 30° C. The water layer was removed and the organic layer was washed twice with $NaHCO_3$ saturated aqueous solution. The organic layer was then carefully washed with 10% w/w citric acid (5 vol) and washed with water (7 vol), and polished filtered and transferred into another dry vessel. 2-methyltetrahydrofuran (10 vol) was added and stirring commenced. Heptane (10 vol) was rapidly added in a dropwise fashion with stirring. The mixture was stirred for a period of about 12 h, and then vacuum filtered. The solid filter cake was introduced into another vessel. Water (15 vol) was charged into the vessel and the suspension was stirred vigorously for 48 h, then filtered. The solid cake was washed with water (5 vol) and dried at 45° C. to constant weight to produce Compound 1 Form B.

Figure 10A:
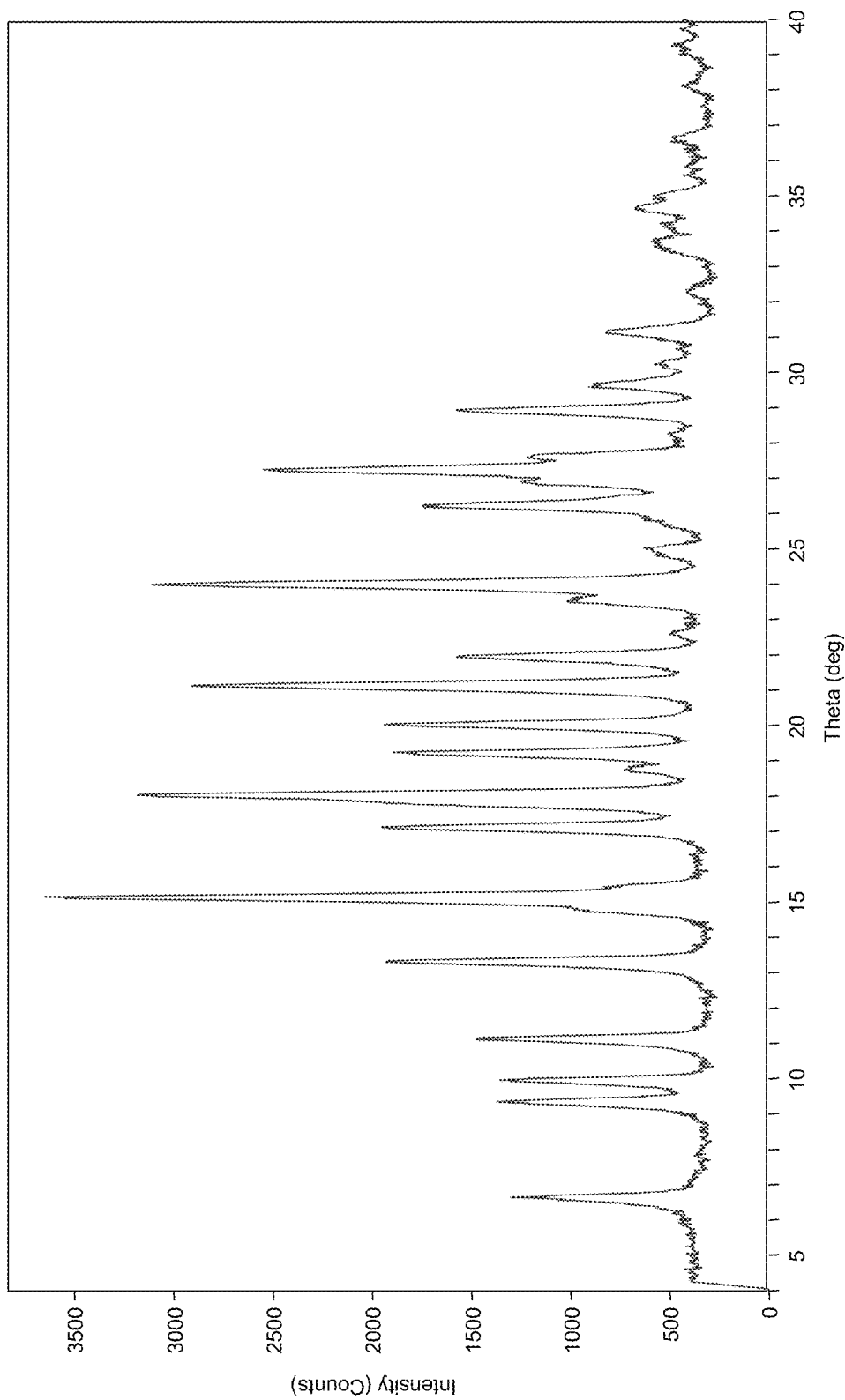
FIG. 10A is an X-ray powder diffraction pattern for a representative sample of Compound 1 Form B, recorded with instrument 1.
Figure 10B:
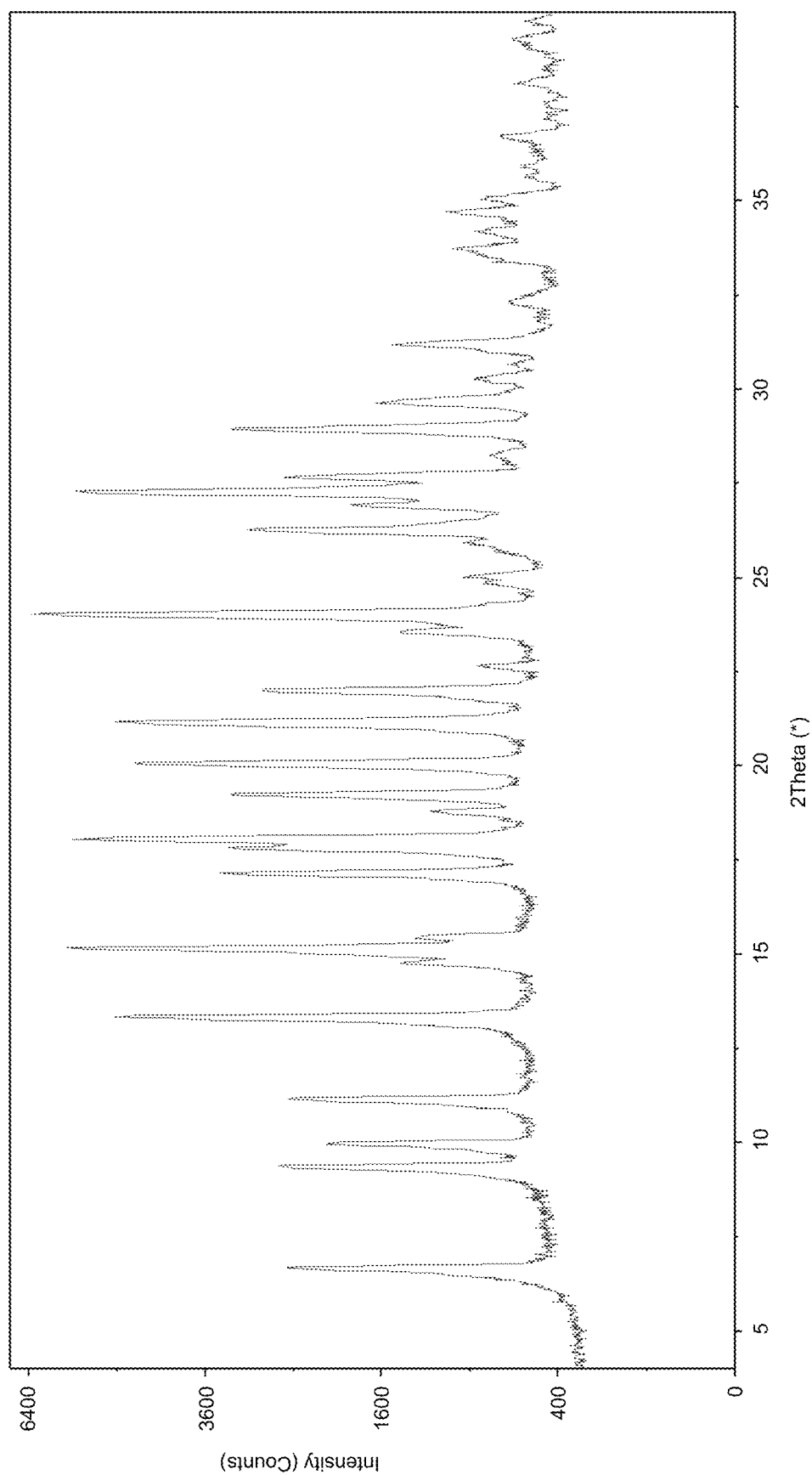
FIG. 10B is an X-ray powder diffraction pattern for a representative sample of Compound 1 Form B, recorded with instrument 2.

The powder diffractograms of Compound 1 Form B recorded using instruments 1 and 2 are shown in FIGS. 10A and 10B respectively.

Table 5 includes the representative XRPD peaks of Compound 1 Form B

TABLE 5

| Representative XRPD Peaks of Compound 1 Form B | |
|---|---|
| 2 Theta (degrees) | Relative Intensity (%) |
| 6.7 | 36.6 |
| 9.4 | 37.2 |
| 10.0 | 29.5 |
| 11.2 | 35.3 |
| 13.4 | 70.6 |
| 14.8 | 18.1 |
| 15.2 | 88.8 |
| 15.4 | 16.6 |
| 17.2 | 49.5 |
| 17.8 | 48.0 |
| 18.1 | 83.8 |
| 18.8 | 13.6 |

TABLE 5-continued

| Representative XRPD Peaks of Compound 1 Form B | |
|---|---|
| 2 Theta (degrees) | Relative Intensity (%) |
| 19.2 | 47.6 |
| 20.1 | 68.9 |
| 21.2 | 71.8 |
| 22.0 | 42.6 |
| 22.6 | 7.6 |
| 23.5 | 18.1 |
| 24.0 | 100.0 |
| 25.0 | 9.6 |
| 25.9 | 9.7 |
| 26.3 | 44.8 |
| 26.9 | 26.3 |
| 27.2 | 86.7 |
| 27.7 | 37.8 |
| 28.2 | 7.4 |
| 28.9 | 49.0 |
| 29.6 | 21.3 |
| 30.3 | 8.6 |
| 30.6 | 5.5 |
| 31.2 | 19.3 |
| 32.3 | 5.5 |
| 33.7 | 11.4 |
| 34.2 | 8.9 |
| 34.7 | 12.4 |
| 35.1 | 8.0 |
| 36.7 | 6.5 |
| 38.1 | 4.7 |
| 39.3 | 5.3 |

Figure 11:
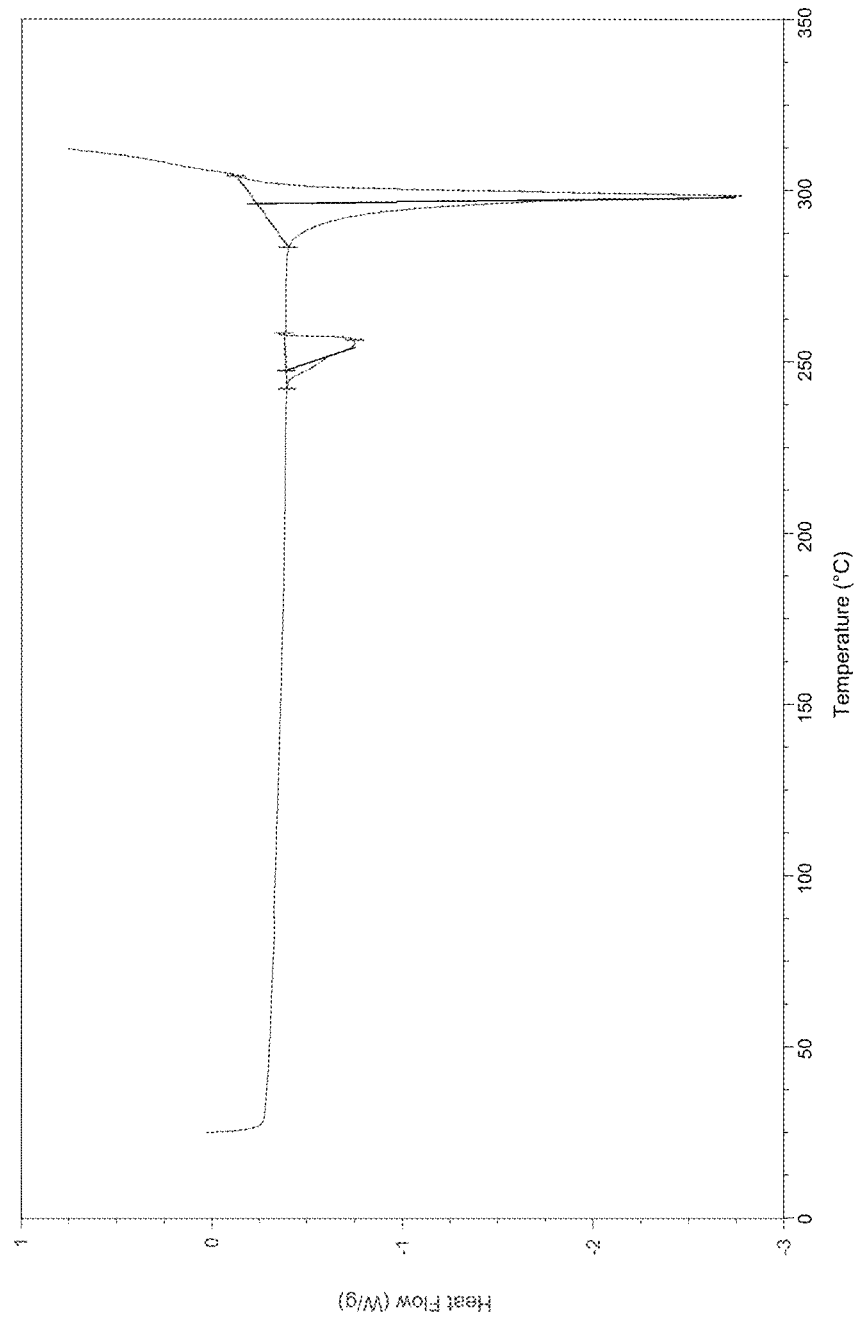
FIG. 11 is the DSC curve for a representative sample of Compound 1 Form B.
Figure 12:
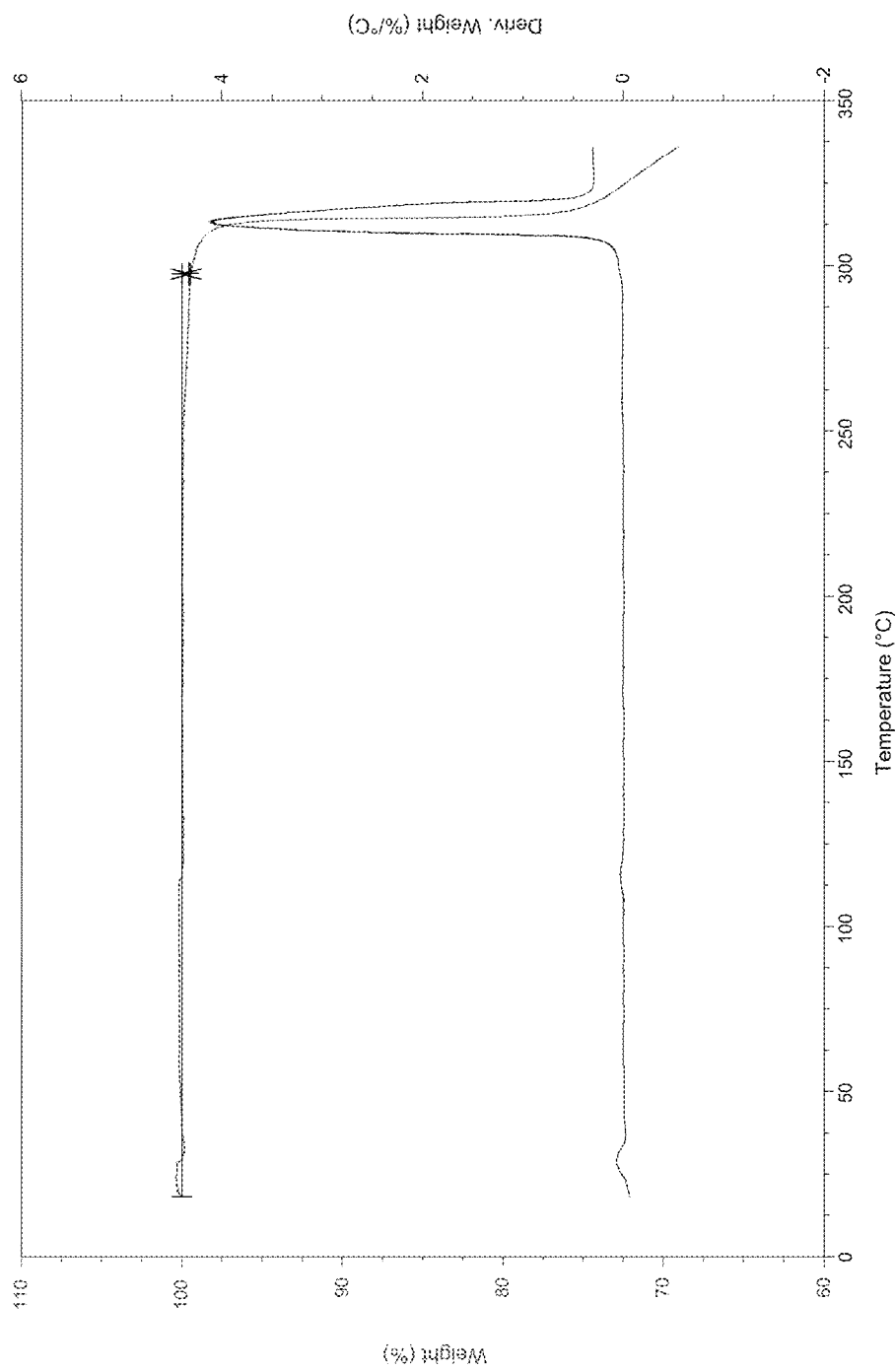
FIG. 12 is a curve generated by thermogravimetric analysis of a representative sample of Compound 1 Form B that presents sample weight as a function of temperature.

A DSC curve for a sample of Compound 1 Form B is provided at FIG. 11, and a TGA curve for a representative sample of Compound 1 Form B is provided in FIG. 12.

Figure 13:
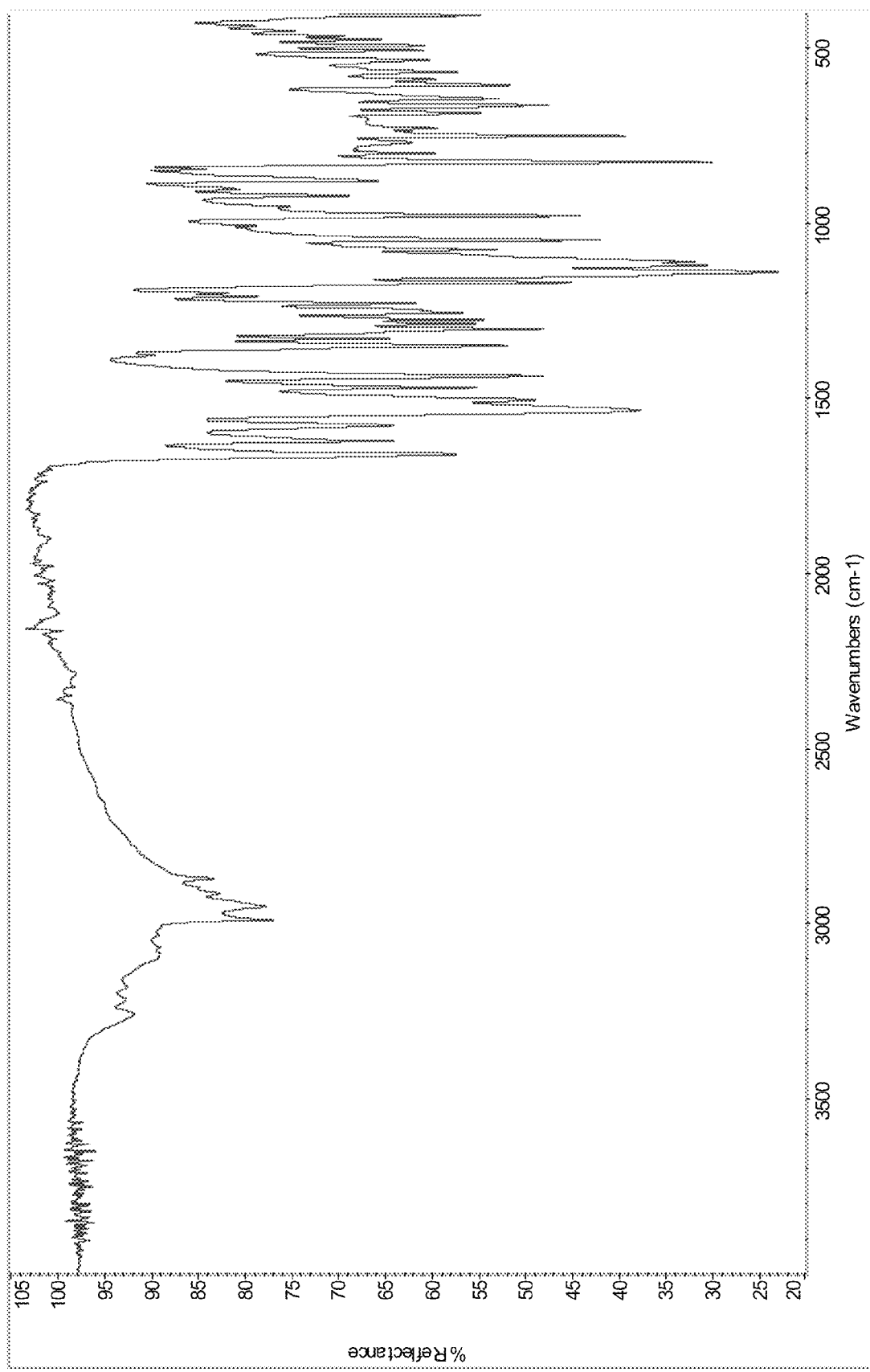
FIG. 13 is an FTIR spectrum of a representative sample of Compound 1 Form B.

A representative sample of Compound 1 Form B presented the FTIR spectrum provided in FIG. 13.

Figure 14:
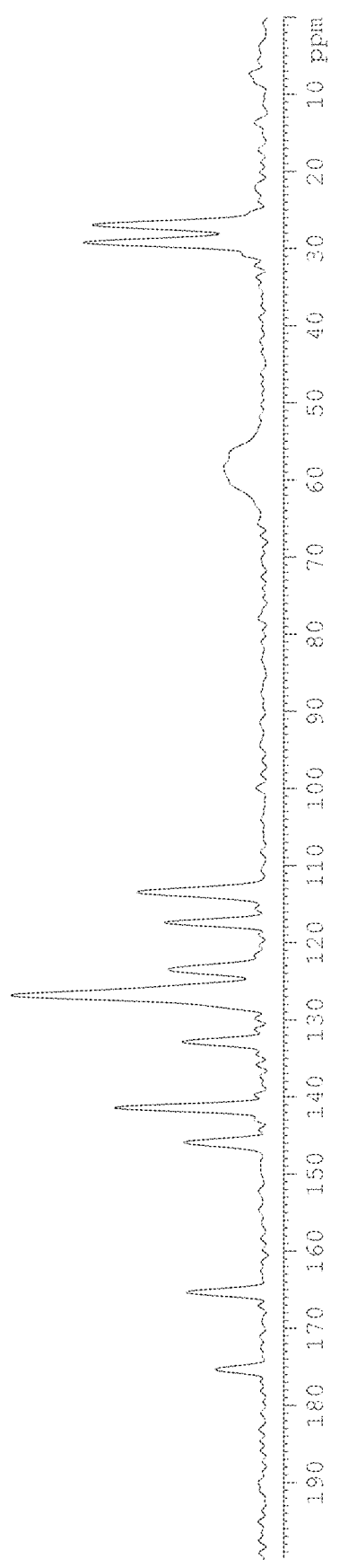
FIG. 14 is a solid phase $^{13}$C NMR spectrum of a representative sample of Compound 1 Form B.
Figure 15:
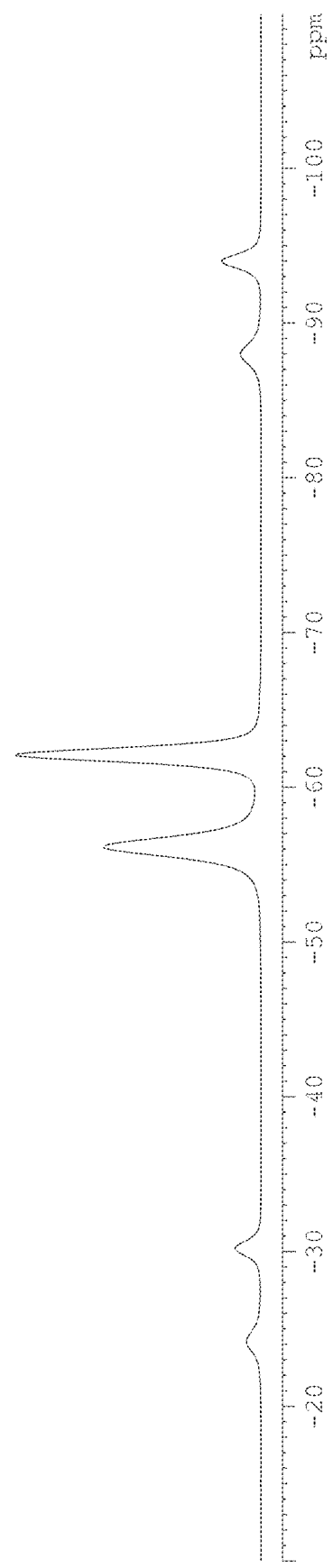
FIG. 15 is solid phase $^{19}$F NMR spectrum of a representative sample of Compound 1 Form B.

Compound 1 Form B was also analyzed using solid state $^{13}C$ and $^{19}F$ NMR. The respective NMR spectra are provided in FIGS. 14 and 15. Several peaks found in the $^{13}C$ SSNMR and $^{19}F$ SSNMR spectra are described in Tables 6 and 7.

TABLE 6

| $^{13}C$ SSNMR Peaks for Compound 1 Form B. | |
|---|---|
| Peak No. | F1 (ppm) |
| 1 | 175.3 |
| 2 | 165.3 |
| 3 | 145.9 |
| 4 | 141.4 |
| 5 | 132.9 |
| 6 | 126.8 |
| 7 | 123.5 |
| 8 | 117.4 |
| 9 | 113.4 |
| 10 | 58.3 |
| 11 | 29.2 |
| 12 | 26.9 |

TABLE 7

| $^{19}F$ SSNMR Peaks for Compound 1 Form B. | |
|---|---|
| Peak No. | F1 (ppm) |
| 1 | −56.1 |
| 2 | −62.1 |

A single crystal of Compound 1 Form B was mounted on a MicroMount loop and centered on a Broker Apex II diffractometer that was equipped with a sealed copper X-ray tube and Apex II CCD detector. Initially, 3 sets of 40 frames were collected to determine a preliminary unit cell. Subsequently a full data set consisting of 15 scans and 6084 frames was acquired. Data collection was performed at room temperature. Data were integrated and scaled using Apex II software from Bruker AXS. Integration and scaling resulted in 6176 reflections, 2250 of which were unique. Structure was solved by direct methods in space group P21/c using SHELXTL software. Refinement was performed with full-matrix least-square method on F2 using SHELXTL software as well. Altogether 392 parameters were used in refinement resulting in reflection to parameter ratio of 5.74. The final refinement index was wR2=0.0962 and R1=0.0682 (wR2=0.0850 and R1=0.0412 for reflections with I>2 sigma(I)).

The single crystal of N-(4-(7-azabicyclo[2.2.1]heptan-7-yl)-2-(trifluoromethyl)phenyl)-4-oxo-5-(trifluoromethyl)-1,4-dihydroquinoline-3-carboxamide in Compound 1 Form B was determined to possess a monoclinic crystal system, a P21/c space group, and the following unit cell dimensions: a=13.5429(4) Å, b=13.4557(4) Å, c=12.0592(4) Å, α=90°, β=101.193°, and γ=90°.

Example 4B

Preparation of N-(4-(7-azabicyclo[2.2.1]heptan-7-yl)-2-(trifluoromethyl)phenyl)-4-oxo-5-(trifluoromethyl)-1,4-dihydroquinoline-3-carboxamide as Form B-HCl (Compound 1 Form B-HCl)

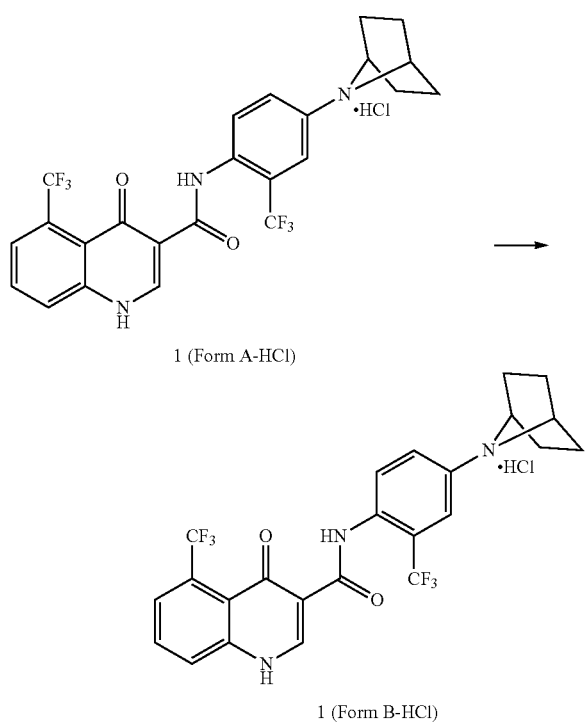

Method 1

100 mL of 2-methyltetrahydrofuran was charged into a 3-necked flask having a nitrogen atmosphere equipped with a stirrer. Compound 1 Form A-HCl (55 g, 0.103 mol) was added to the flask followed by 349 mL of 2-methyltetrahydrofuran, and stirring commenced. 28 mL of water was added into the flask and the flask was warmed to an internal temperature of 60° C. and stirred for 48 h. The flask was cooled to room temperature and stirred for 1 h. The reaction mixture was vacuum filtered until the filter cake was dry. The solid filter cake was washed with 2-methyltetrahydrofuran (4 vol) twice. The solid filter cake remained under vacuum suction for a period of about 30 minutes and was transferred to a drying tray. The filter cake was dried to a constant weight under vacuum at 60° C. This resulted in the generation of Compound 1 Form B-HCl as a white crystalline solid. Method 2.

Compound 1 Form A-HCl (14.638 g, 27.52 mmol) was charged to a 100 mL round bottom flask. EtOH (248.9 mL) and water (27.82 mL) were added. The white slurry was heated to reflux. A clear solution was obtained at 77° C. The reaction was cooled to 45° C., and was allowed to stir for 30 min, and then was cooled to 20° C. The mixture was allowed to stir for an additional 3 h at 20° C. The product was filtered and the cake washed with EtOH. The solid was dried in a vacuum oven at 45° C. with a nitrogen bleed to provide Compound 1 Form B-HCl as a white solid.

As a note, other solvent combination such as MeOH/H$_2$O and IPA/H$_2$O or the like can be used instead of EtOH/H$_2$O as described in this example.

Examples of alternative solvent combinations are provided in Table 8.

TABLE 8

Other Solvents that Can Be Used to Make Form B-HCl.

| Solvent | Solvent Volume | T [° C.] |
|---|---|---|
| MeOH | 10 | 60 |
| MeOH:H$_2$O | 10:0.2 | 60 |
| MeOH:H$_2$O | 10:0.5 | 60 |
| MeOH:H$_2$O | 10:1 | 60 |
| MeOH:H$_2$O | 10:1.5 | 60 |
| IPA:H$_2$O | 10:1 | 75 |
| IPA:H$_2$O | 10:1.5 | 75 |
| MeOH:H$_2$O | 10:1 | 65 |
| EtOH | 10 | 70 |
| EtOH:H$_2$O | 10:0.2 | 70 |
| EtOH:H$_2$O | 10:0.5 | 70 |
| EtOH:H$_2$O | 10:1 | 70 |
| EtOH:H$_2$O | 10:1.5 | 70 |

Figure 16:
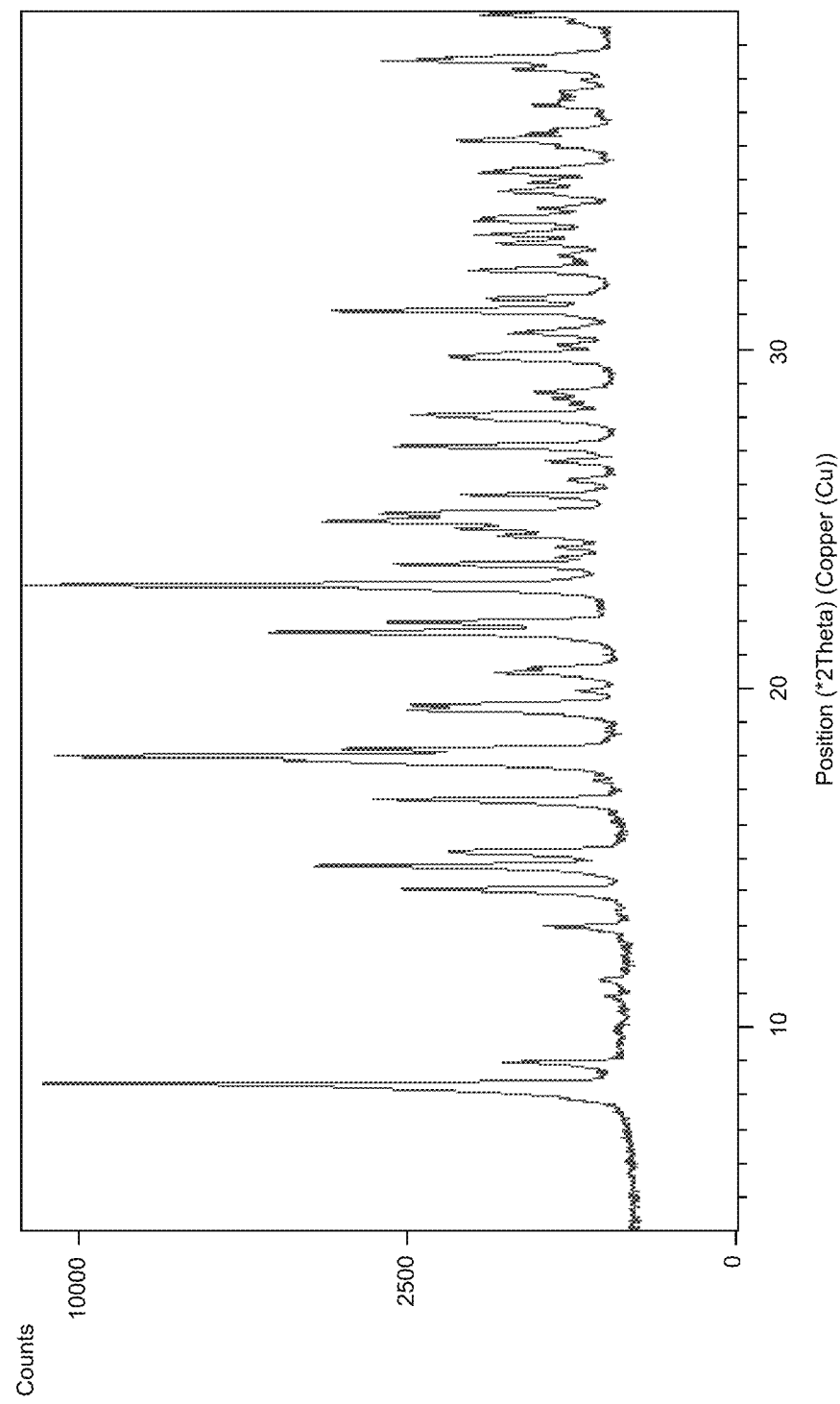
FIG. 16 is an X-ray powder diffraction pattern of Compound 1 Form B-HCl.

The powder diffractogram of Form Compound 1 B-HCl is shown in FIG. 16.

TABLE 9

Representative XRPD peaks of Compound 1 Form B-HCl

| 2-Theta (degrees) | Relative Intensity (%) |
|---|---|
| 8.3 | 93.7 |
| 9.0 | 8.4 |
| 10.9 | 0.8 |
| 11.4 | 1.4 |
| 13.0 | 4.9 |
| 14.1 | 19.8 |
| 14.8 | 32.7 |
| 15.2 | 12.6 |
| 16.7 | 23.8 |
| 17.8 | 37.8 |
| 18.0 | 90.0 |
| 18.2 | 28.6 |
| 19.3 | 19.0 |
| 19.5 | 17.5 |
| 19.9 | 2.7 |
| 20.4 | 9.4 |
| 20.6 | 6.2 |
| 21.7 | 41.2 |
| 22.0 | 22.2 |
| 23.0 | 100.0 |
| 23.6 | 20.5 |

TABLE 9-continued

Representative XRPD peaks of Compound 1 Form B-HCl

| 2-Theta (degrees) | Relative Intensity (%) |
|---|---|
| 23.9 | 4.0 |
| 24.1 | 3.9 |
| 24.5 | 9.2 |
| 24.7 | 13.0 |
| 24.9 | 31.9 |
| 25.2 | 22.6 |
| 25.7 | 12.6 |
| 26.1 | 3.3 |
| 26.7 | 4.5 |
| 27.1 | 21.3 |
| 27.9 | 10.6 |
| 28.1 | 18.7 |
| 28.5 | 4.3 |
| 28.7 | 5.8 |
| 29.7 | 11.1 |
| 29.8 | 14.2 |
| 30.1 | 4.0 |
| 30.5 | 8.2 |
| 31.1 | 30.2 |
| 31.5 | 9.1 |
| 32.3 | 11.4 |
| 32.8 | 3.8 |
| 33.1 | 9.2 |
| 33.4 | 11.3 |
| 33.8 | 11.1 |
| 33.9 | 10.1 |
| 34.1 | 5.6 |
| 34.6 | 8.5 |
| 34.9 | 6.4 |
| 35.2 | 10.8 |
| 36.0 | 4.1 |
| 36.2 | 13.2 |
| 36.4 | 4.7 |
| 37.2 | 5.9 |
| 37.6 | 3.7 |
| 37.9 | 2.2 |
| 38.2 | 7.5 |
| 38.5 | 22.3 |
| 38.6 | 13.8 |
| 39.9 | 10.7 |

A single crystal of Compound 1 Form B-HCl was determined to possess a monoclinic crystal system, a P2$_1$/a space group, and the following unit cell dimensions: a=12.57334(5) Å, b=19.68634(5) Å, c=8.39399(5) Å, α=90°, β=90.0554°, and γ=90°.

A sample of Compound Form B-HCl was also evaluated using microscopy.

Figure 17:
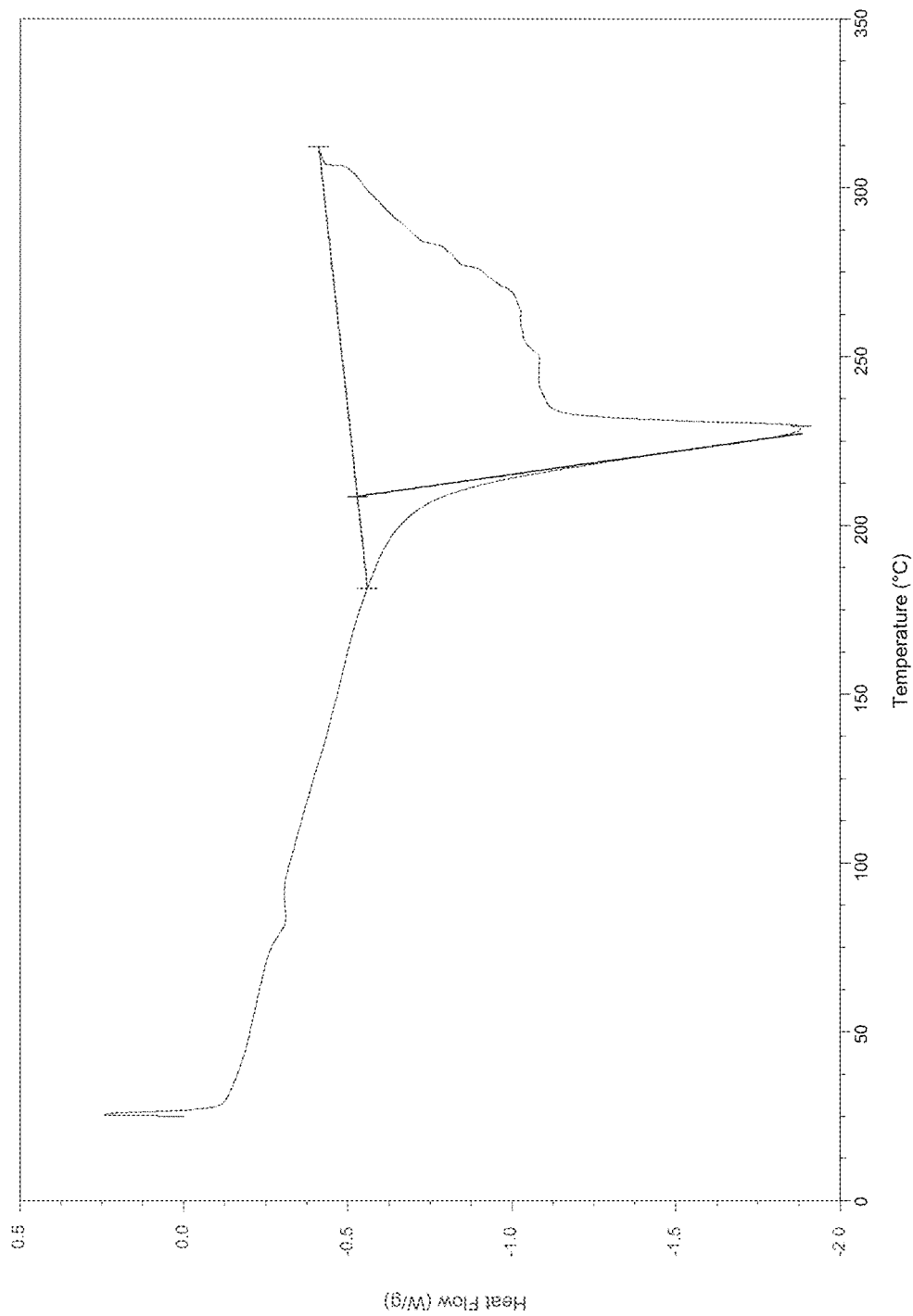
FIG. 17 is the DSC curve for a representative sample of Compound 1 Form B-HCl.
Figure 18:
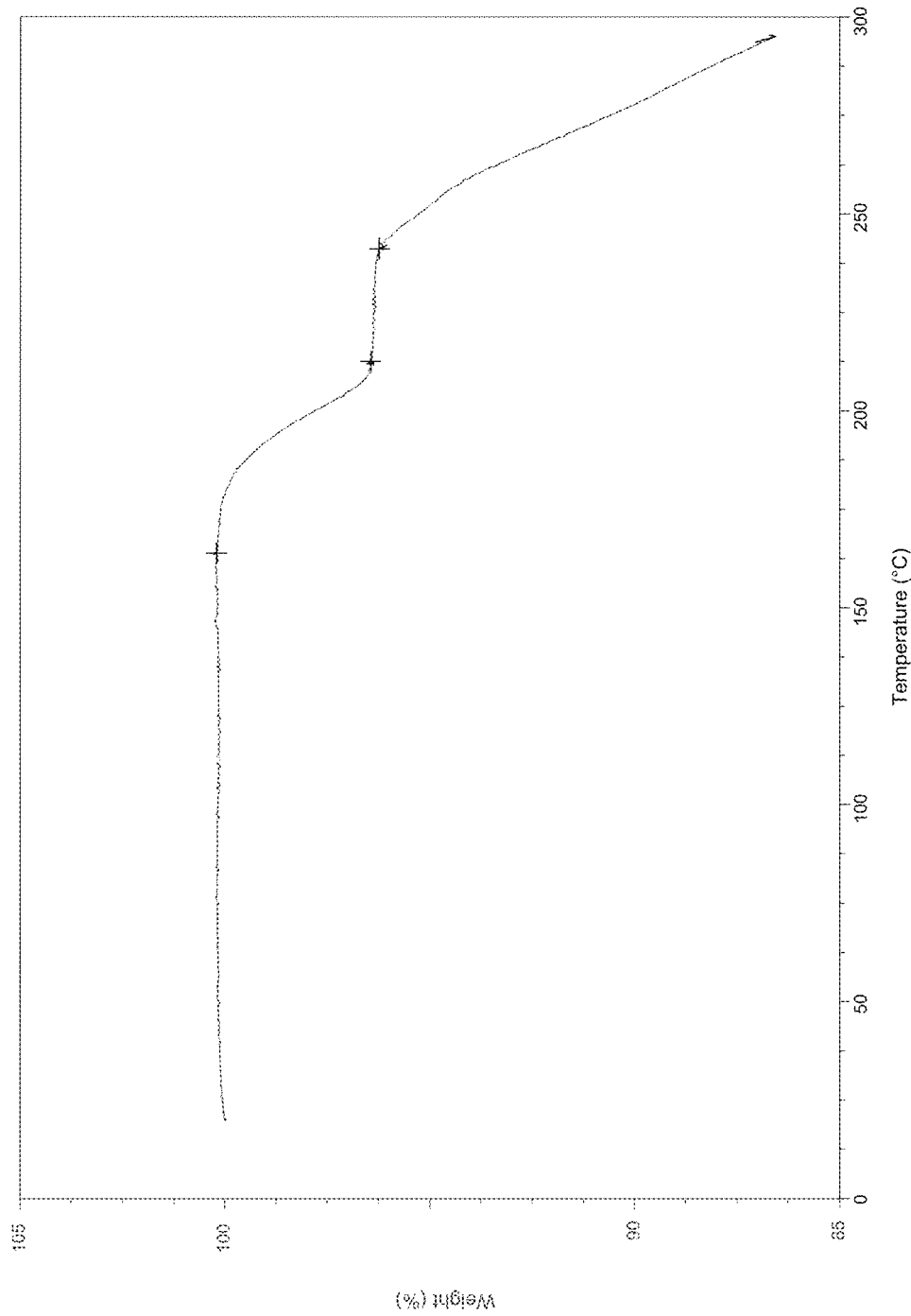
FIG. 18 is a curve generated by thermogravimetric analysis of a representative sample of Compound 1 Form B-HCl that presents sample weight as a function of temperature.

A DSC curve for Compound 1 Form B-HCl is provided in FIG. 17, and a TGA curve for a representative sample of Compound 1 Form B-HCl is provided in FIG. 18.

Figure 19:
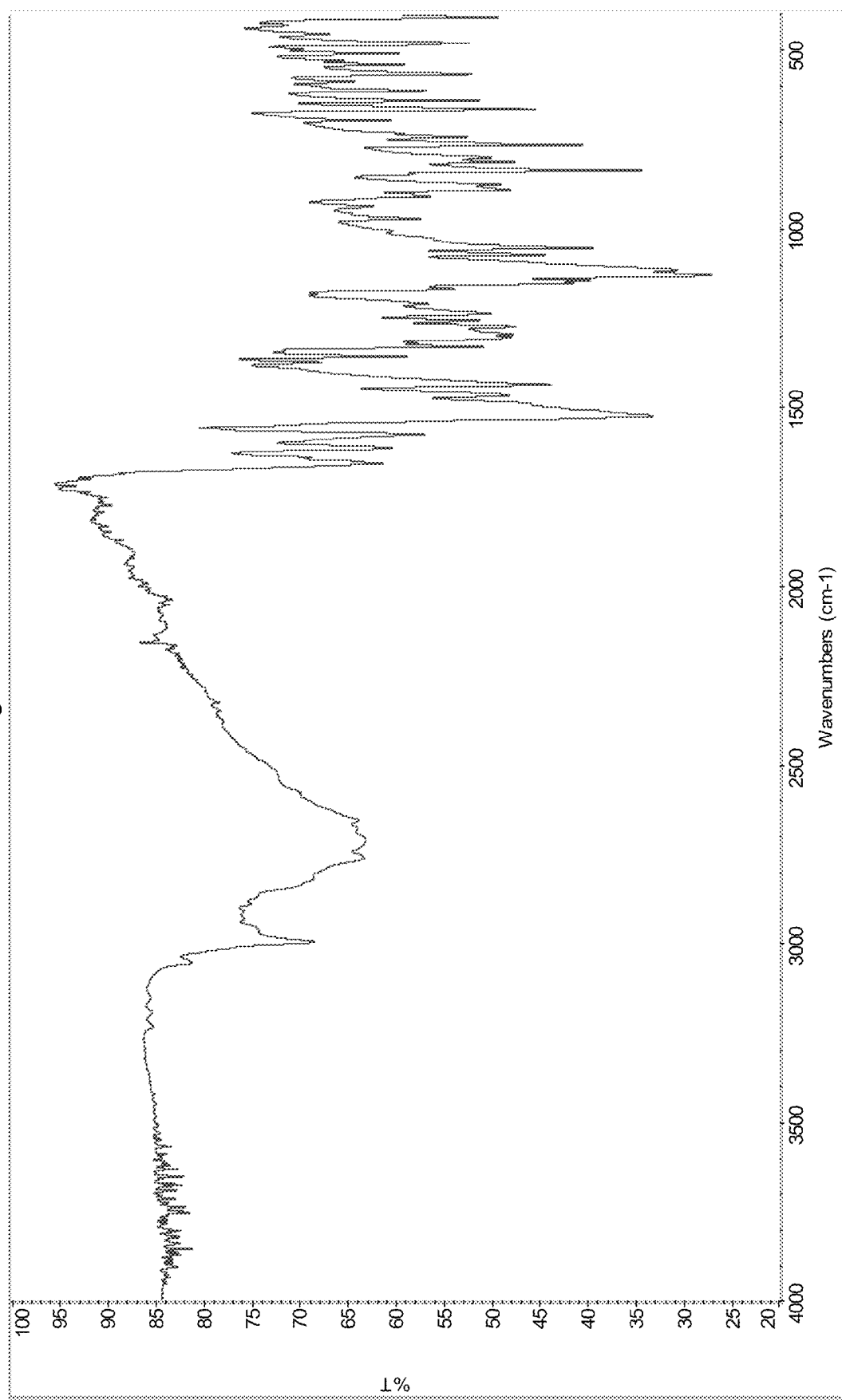
FIG. 19 is an FTIR spectrum of a representative sample of Compound 1 Form B-HCl.

A representative sample of Compound 1 Form B-HCl presented the FTIR spectrum provided in FIG. 19.

Figure 20:
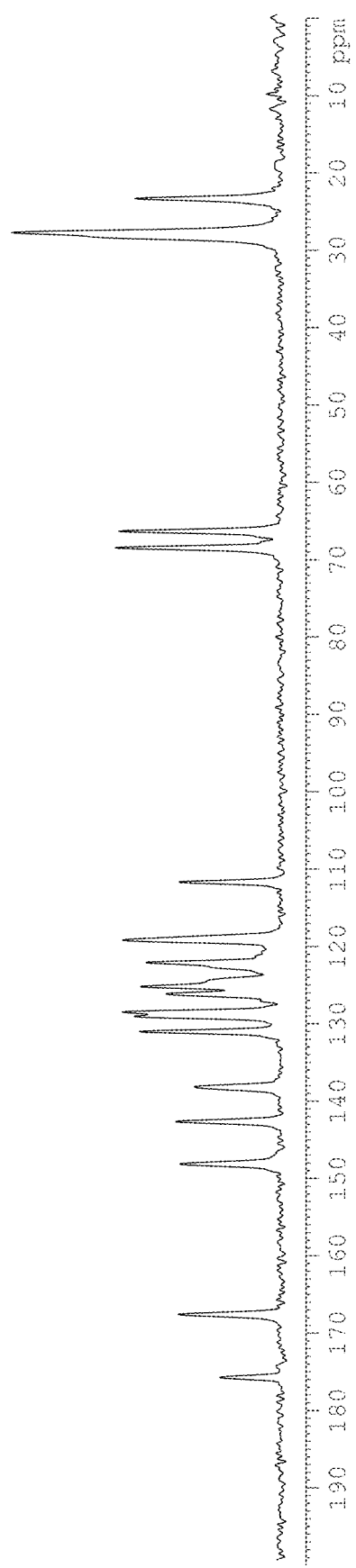
FIG. 20 is a solid phase $^{13}$C NMR spectrum of a representative sample of Compound 1 Form B-HCl.
Figure 21:
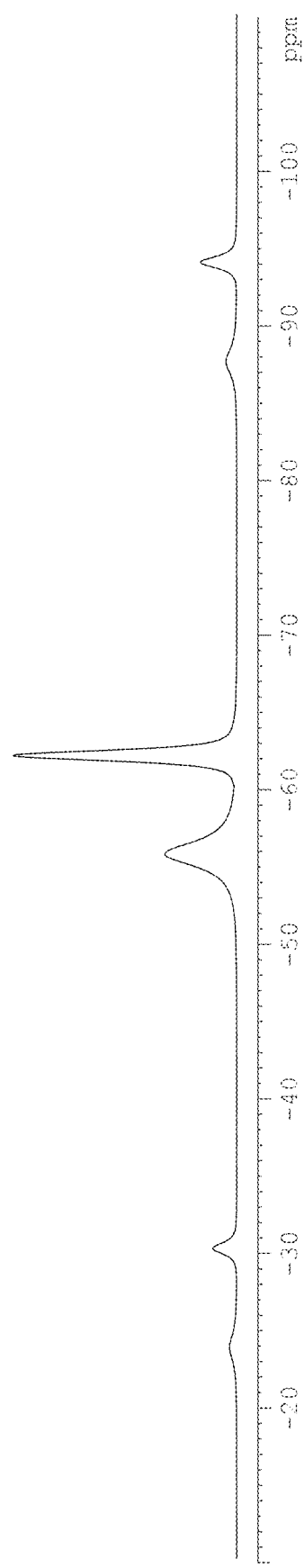
FIG. 21 is solid phase $^{19}$F NMR spectrum of a representative sample of Compound 1 Form B-HCl.

Compound 1 Form B-HCl was also analyzed using solid state $^{13}$C and $^{19}$F NMR. The respective NMR spectra are provided in FIGS. 20 and 21. Several peaks found in the $^{13}$C SSNMR and $^{19}$F SSNMR spectra are described in Tables 10 and 11:

TABLE 9

$^{13}$C SSNMR Peaks for Compound 1 Form B-HCl.

| Peak No. | F1 (ppm) |
|---|---|
| 1 | 176.3 |
| 2 | 168.2 |
| 3 | 148.7 |
| 4 | 143.2 |
| 5 | 138.8 |

TABLE 9-continued $^{13}$C SSNMR Peaks for Compound 1 Form B-HCl.

| Peak No. | F1 (ppm) |
|---|---|
| 6 | 131.6 |
| 7 | 129.6 |
| 8 | 129.1 |
| 9 | 126.7 |
| 10 | 125.8 |
| 11 | 122.7 |
| 12 | 119.8 |
| 13 | 112.3 |
| 14 | 69.0 |
| 15 | 66.9 |
| 16 | 28.3 |
| 17 | 23.9 |

TABLE 10

$^{19}$F SSNMR Peaks for Compound 1 Form B-HCl.

| Peak No. | F1 (ppm) |
|---|---|
| 1 | −55.6 |
| 2 | −62.0 |

As a note, in Examples 3A, 3B, and 4A-4C, EtOAC may be used instead of 2-MeTHF as the solvent.

Assays for Detecting and Measuring ΔF508-CFTR Potentiation Properties of Compounds Membrane Potential Optical Methods for Assaying ΔF508-CFTR Modulation Properties of Compounds The assay utilizes fluorescent voltage sensing dyes to measure changes in membrane potential using a fluorescent plate reader (e.g., FLIPR III, Molecular Devices, Inc.) as a readout for increase in functional ΔF508-CFTR in NIH 3T3 cells. The driving force for the response is the creation of a chloride ion gradient in conjunction with channel activation by a single liquid addition step after the cells have previously been treated with compounds and subsequently loaded with a voltage sensing dye.

Identification of Potentiator Compounds

To identify potentiators of ΔF508-CFTR, a double-addition HTS assay format was developed. This HTS assay utilizes fluorescent voltage sensing dyes to measure changes in membrane potential on the FLIPR III as a measurement for increase in gating (conductance) of ΔF508 CFTR in temperature-corrected ΔF508 CFTR NIH 3T3 cells. The driving force for the response is a Cl⁻ ion gradient in conjunction with channel activation with forskolin in a single liquid addition step using a fluorescent plate reader such as FLIPR III after the cells have previously been treated with potentiator compounds (or DMSO vehicle control) and subsequently loaded with a redistribution dye.

Solutions

Bath Solution #1: (in mM) NaCl 160, KCl 4.5, CaCl$_2$ 2, MgCl$_2$ 1, HEPES 10, pH 7.4 with NaOH.

An alternative to Bath Solution #1 includes a bath solution where the chloride salts are substituted with gluconate salts.

Cell Culture

NIH3T3 mouse fibroblasts stably expressing ΔF508-CFTR are used for optical measurements of membrane potential. The cells are maintained at 37° C. in 5% CO$_2$ and 90% humidity in Dulbecco's modified Eagle's medium supplemented with 2 mM glutamine, 10% fetal bovine serum, 1×NEAA, n-ME, β-ME, 1×pen/strep, and 25 mM HEPES in 175 cm$^2$ culture flasks. For all optical assays, the cells were seeded at ~20,000/well in 384-well matrigel-coated plates and cultured for 2 hrs at 37° C. before culturing at 27° C. for 24 hrs. for the potentiator assay. For the correction assays, the cells are cultured at 27° C. or 37° C. with and without compounds for 16-24 hours.

Electrophysiological Assays for Assaying ΔF508-CFTR Modulation Properties of Compounds.

1. Ussing Chamber Assaying

Ussing chamber experiments were performed on polarized airway epithelial cells expressing ΔF508-CFTR to further characterize the ΔF508-CFTR modulators identified in the optical assays. Non-CF and CF airway epithelia were isolated from bronchial tissue, cultured as previously described (Galietta, L. J. V., Lantero, S., Gazzolo, A., Sacco, O., Romano, L., Rossi, G. A., & Zegarra-Moran, O. (1998) In Vitro Cell. Dev. Biol. 34, 478-481), and plated onto Costar® Snapwell™ filters that were precoated with NIH3T3-conditioned media. After four days the apical media was removed and the cells were grown at an air liquid interface for >14 days prior to use. This resulted in a monolayer of fully differentiated columnar cells that were ciliated, features that are characteristic of airway epithelia. Non-CF HBE were isolated from non-smokers that did not have any known lung disease. CF-HBE were isolated from patients homozygous for ΔF508-CFTR.

HBE grown on Costar® Snapwell™ cell culture inserts were mounted in an Using chamber (Physiologic Instruments, Inc., San Diego, Calif.), and the transepithelial resistance and short-circuit current in the presence of a basolateral to apical gradient ($I_{SC}$) were measured using a voltage-clamp system (Department of Bioengineering, University of Iowa, IA). Briefly, HBE were examined under voltage-clamp recording conditions ($V_{hold}$=0 mV) at 37° C. The basolateral solution contained (in mM) 145 NaCl, 0.83 $K_2HPO_4$, 3.3 $KH_2PO_4$, 1.2 $MgCl_2$, 1.2 $CaCl_2$, 10 Glucose, 10 HEPES (pH adjusted to 7.35 with NaOH) and the apical solution contained (in mM) 145 NaGluconate, 1.2 $MgCl_2$, 1.2 $CaCl_2$, 10 glucose, 10 HEPES (pH adjusted to 7.35 with NaOH).

Identification of Potentiator Compounds

Typical protocol utilized a basolateral to apical membrane Cl⁻ concentration gradient. To set up this gradient, normal ringers was used on the basolateral membrane, whereas apical NaCl was replaced by equimolar sodium gluconate (titrated to pH 7.4 with NaOH) to give a large Cl⁻ concentration gradient across the epithelium. Forskolin (10 μM) and all test compounds were added to the apical side of the cell culture inserts. The efficacy of the putative ΔF508-CFTR potentiators was compared to that of the known potentiator, genistein.

Patch-clamp Recordings

Total Cl⁻ current in ΔF508-NIH3T3 cells was monitored using the perforated-patch recording configuration as previously described (Rae, J., Cooper, K., Gates, P., & Watsky, M. (1991) J. Neurosci. Methods 37, 15-26). Voltage-clamp recordings were performed at 22° C. using an Axopatch 200B patch-clamp amplifier (Axon Instruments Inc., Foster City, Calif.). The pipette solution contained (in mM) 150 N-methyl-D-glucamine (NMDG)-Cl, 2 $MgCl_2$, 2 $CaCl_2$, EGTA, 10 HEPES, and 240 μg/ml amphotericin-B (pH adjusted to 7.35 with HCl). The extracellular medium contained (in mM) 150 NMDG-Cl, 2 $MgCl_2$, 2 $CaCl_2$, 10 HEPES (pH adjusted to 7.35 with HCl). Pulse generation, data acquisition, and analysis were performed using a PC equipped with a Digidata 1320 A/D interface in conjunction with Clampex 8 (Axon Instruments Inc.). To activate ΔF508-CFTR, 10 μM forskolin and 20 μM genistein were added to the bath and the current-voltage relation was monitored every 30 sec.

Identification of Potentiator Compounds

The ability of ΔF508-CFTR potentiators to increase the macroscopic ΔF508-CFTR Cl⁻ current ($I_{\Delta F508}$) in NIH3T3 cells stably expressing ΔF508-CFTR was also investigated using perforated-patch-recording techniques. The potentiators identified from the optical assays evoked a dose-dependent increase in $I_{\Delta F508}$ with similar potency and efficacy observed in the optical assays. In all cells examined, the reversal potential before and during potentiator application was around −30 mV, which is the calculated $E_{Cl}$ (−28 mV).

Cell Culture

NIH3T3 mouse fibroblasts stably expressing ΔF508-CFTR are used for whole-cell recordings. The cells are maintained at 37° C. in 5% $CO_2$ and 90% humidity in Dulbecco's modified Eagle's medium supplemented with 2 mM glutamine, 10% fetal bovine serum, 1×NEAA, β-ME, 1×pen/strep, and 25 mM HEPES in 175 cm² culture flasks. For whole-cell recordings, 2,500-5,000 cells were seeded on poly-L-lysine-coated glass coverslips and cultured for 24-48 hrs at 27° C. before use to test the activity of potentiators; and incubated with or without the correction compound at 37° C. for measuring the activity of correctors.

Single-Channel Recordings

Gating activity of wt-CFTR and temperature-corrected ΔF508-CFTR expressed in NIH3T3 cells was observed using excised inside-out membrane patch recordings as previously described (Dalemans, W., Barbry, P., Champigny, G., Jallat, S., Dott, K., Dreyer, D., Crystal, R. G., Pavirani, A., Lecocq, J-P., Lazdunski, M. (1991) Nature 354, 526-528) using an Axopatch 200B patch-clamp amplifier (Axon Instruments Inc.). The pipette contained (in mM): 150 NMDG, 150 aspartic acid, 5 $CaCl_2$, 2 $MgCl_2$, and 10 HEPES (pH adjusted to 7.35 with Tris base). The bath contained (in mM): 150 NMDG-Cl, 2 $M_gCl_2$, 5 EGTA, 10 TES, and 14 Tris base (pH adjusted to 7.35 with HCl). After excision, both wt- and ΔF508-CFTR were activated by adding 1 mM Mg-ATP, 75 nM of the catalytic subunit of cAMP-dependent protein kinase (PKA; Promega Corp. Madison, Wis.), and 10 mM NaF to inhibit protein phosphatases, which prevented current rundown. The pipette potential was maintained at 80 mV. Channel activity was analyzed from membrane patches containing 2 active channels. The maximum number of simultaneous openings determined the number of active channels during the course of an experiment. To determine the single-channel current amplitude, the data recorded from 120 sec of ΔF508-CFTR activity was filtered "off-line" at 100 Hz and then used to construct all-point amplitude histograms that were fitted with multigaussian functions using Bio-Patch Analysis software (Bio-Logic Comp. France). The total microscopic current and open probability ($P_o$) were determined from 120 sec of channel activity. The P. was determined using the Bio-Patch software or from the relationship $P_o=I/i(N)$, where I=mean current, i=single-channel current amplitude, and N=number of active channels in patch.

Cell Culture

NIH3T3 mouse fibroblasts stably expressing ΔF508-CFTR are used for excised-membrane patch-clamp recordings. The cells are maintained at 37° C. in 5% $CO_2$ and 90% humidity in Dulbecco's modified Eagle's medium supplemented with 2 mM glutamine, 10% fetal bovine serum, 1×NEAA, n-ME, 1×pen/strep, and 25 mM HEPES in 175 cm² culture flasks. For single channel recordings, 2,500-5,000 cells were seeded on poly-L-lysine-coated glass coverslips and cultured for 24-48 hrs at 27° C. before use.

Compound 1 is useful as modulators of ATP binding cassette transporters. The $EC_{50}$ (μm) of Compound 1 Form A was measured to be less than 2.0 μM. The efficacy of Compound 1 Form A was calculated to be from 100% to 25%. It should be noted that 100% efficacy is the maximum response obtained with 4-methyl-2-(5-phenyl-1H-pyrazol-3-yl)phenol.

Other Embodiments

All publications and patents referred to in this disclosure are incorporated herein by reference to the same extent as if each individual publication or patent application were specifically and individually indicated to be incorporated by reference. Should the meaning of the terms in any of the patents or publications incorporated by reference conflict with the meaning of the terms used in this disclosure, the meaning of the terms in this disclosure are intended to be controlling. Furthermore, the foregoing discussion discloses and describes merely exemplary embodiments of the present invention. One skilled in the art will readily recognize from such discussion and from the accompanying drawings and claims, that various changes, modifications and variations can be made therein without departing from the spirit and scope of the invention as defined in the following claims.

What is claimed is:

1. A process for producing a hydrochloride salt of Compound 1 having the solid Form B-HCl

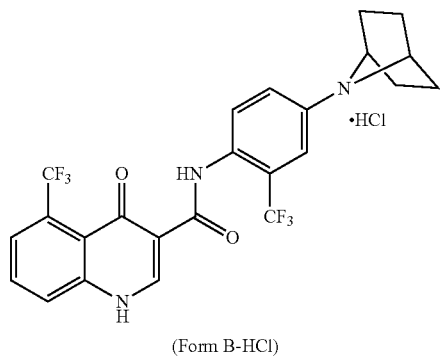

(Form B-HCl)

comprising:
(a) mixing a hydrochloride salt of Compound 1 Form A-HCl with an organic solvent and water to generate a mixture;

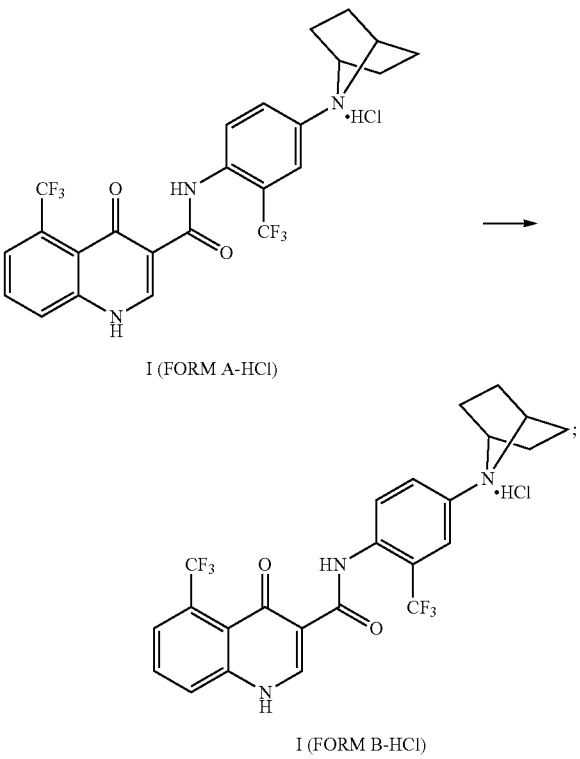

I (FORM A-HCl)

I (FORM B-HCl)

and
(b) heating the mixture.

2. The process of claim 1, wherein the organic solvent comprises dimethyl sulfoxide, dimethylformamide, dioxane, hexamethylphosphorotriamide, tetrahydrofuran, EtOAc, IPAc, THF, MEK, NMP, acetonitrile, DMF, EtOH, MeOH, isopropyl alcohol, or 2-methyltetrahydrofuran.

3. The process of claim 2, wherein the organic solvent comprises 2-methyltetrahydrofuran.

4. The process of claim 1, wherein the mixture is maintained at a temperature from about 30° C. to about 80° C.

5. The process of claim 4, wherein the mixture is maintained at a temperature from about 30° C. to about 80° C. for a period of from about 12 hours to about 72 hours.

6. The process of claim 1, wherein the mixture is filtered to generate a filter cake.

7. The process of claim 6, wherein filtering is followed by washing the filter cake with an aprotic solvent.

* * * * *